(12) United States Patent
Ghaffari et al.

(10) Patent No.: US 9,629,586 B2
(45) Date of Patent: *Apr. 25, 2017

(54) SYSTEMS, METHODS, AND DEVICES USING STRETCHABLE OR FLEXIBLE ELECTRONICS FOR MEDICAL APPLICATIONS

(71) Applicant: MC10 Inc., Cambridge, MA (US)

(72) Inventors: Roozbeh Ghaffari, Cambridge, MA (US); Bassel de Graff, San Juan (TT); Gilman Callsen, Malden, MA (US); William J. Arora, Boston, MA (US); Benjamin Schlatka, Lexington, MA (US); Eugene Kuznetsov, Cambridge, MA (US)

(73) Assignee: MC10, Inc., Lexington, MA (US)

( * ) Notice: Subject to any disclaimer, the term of this patent is extended or adjusted under 35 U.S.C. 154(b) by 134 days.

This patent is subject to a terminal disclaimer.

(21) Appl. No.: 14/518,856

(22) Filed: Oct. 20, 2014

(65) Prior Publication Data

US 2015/0099976 A1 Apr. 9, 2015

Related U.S. Application Data

(60) Division of application No. 12/636,071, filed on Dec. 11, 2009, now Pat. No. 8,886,334, which is a
(Continued)

(51) Int. Cl.
*A61N 1/04* (2006.01)
*A61B 5/00* (2006.01)
(Continued)

(52) U.S. Cl.
CPC ........ *A61B 5/6879* (2013.01); *A61B 1/00082* (2013.01); *A61B 1/01* (2013.01);
(Continued)

(58) Field of Classification Search
CPC ..... A61B 5/01; A61B 5/6853; A61B 18/1492; A61B 2018/0016; A61B 2018/0022; A61B 2018/0577; A61B 2018/00839
(Continued)

(56) References Cited

U.S. PATENT DOCUMENTS 4,058,418 A 11/1977 Lindmayer
4,416,288 A 11/1983 Freeman
(Continued)

FOREIGN PATENT DOCUMENTS

CN 1864095 11/2006
JP 2001332383 11/2001
(Continued)

OTHER PUBLICATIONS

Office Action in Japanese Patent Application No. 2015-021181, dated Feb. 9, 2016. (8 pages with English Translation).
(Continued)

*Primary Examiner* — Allen Porter, Jr.
(74) *Attorney, Agent, or Firm* — Nixon Peabody LLP

(57) ABSTRACT

System, devices and methods are presented that integrate stretchable or flexible circuitry, including arrays of active devices for enhanced sensing, diagnostic, and therapeutic capabilities. The invention enables conformal sensing contact with tissues of interest, such as the inner wall of a lumen, a nerve bundle, or the surface of the heart. Such direct, conformal contact increases accuracy of measurement and delivery of therapy.

74 Claims, 22 Drawing Sheets

Related U.S. Application Data continuation-in-part of application No. 12/616,922, filed on Nov. 12, 2009, now Pat. No. 8,389,862, which is a continuation-in-part of application No. 12/575,008, filed on Oct. 7, 2009, now Pat. No. 9,289,132.

(60) Provisional application No. 61/121,568, filed on Dec. 11, 2008, provisional application No. 61/121,541, filed on Dec. 11, 2008, provisional application No. 61/140,169, filed on Dec. 23, 2008, provisional application No. 61/113,622, filed on Nov. 12, 2008, provisional application No. 61/103,361, filed on Oct. 7, 2008, provisional application No. 61/113,007, filed on Nov. 10, 2008.

(51) Int. Cl.

| | | |
|---|---|---|
| *A61B 1/00* | (2006.01) | |
| *A61B 5/04* | (2006.01) | |
| *A61B 1/01* | (2006.01) | |
| *A61B 5/02* | (2006.01) | |
| *A61B 5/0205* | (2006.01) | |
| *A61B 8/14* | (2006.01) | |
| *A61B 18/02* | (2006.01) | |
| *A61B 18/14* | (2006.01) | |
| *A61B 18/20* | (2006.01) | |
| *A61M 5/172* | (2006.01) | |
| *A61B 5/01* | (2006.01) | |
| *A61B 5/145* | (2006.01) | |
| *H01L 27/146* | (2006.01) | |
| *A61B 18/00* | (2006.01) | |

(52) U.S. Cl.
CPC .............. *A61B 5/00* (2013.01); *A61B 5/0059* (2013.01); *A61B 5/02028* (2013.01); *A61B 5/02055* (2013.01); *A61B 5/04001* (2013.01); *A61B 8/14* (2013.01); *A61B 18/02* (2013.01); *A61B 18/14* (2013.01); *A61B 18/20* (2013.01); *A61M 5/1723* (2013.01); *A61N 1/04* (2013.01); *A61B 5/01* (2013.01); *A61B 5/145* (2013.01); *A61B 5/14532* (2013.01); *A61B 5/14539* (2013.01); *A61B 5/14546* (2013.01); *A61B 2018/0022* (2013.01); *A61B 2018/00577* (2013.01); *A61B 2562/02* (2013.01); *A61B 2562/0204* (2013.01); *A61B 2562/0209* (2013.01); *A61B 2562/0233* (2013.01); *A61B 2562/0247* (2013.01); *A61B 2562/046* (2013.01); *A61B 2562/164* (2013.01); *H01L 27/14609* (2013.01)

(58) Field of Classification Search
USPC ................. 600/374, 393, 547, 549; 606/192
See application file for complete search history.

(56) References Cited

U.S. PATENT DOCUMENTS

| | | |
|---|---|---|
| 4,658,153 A | 4/1987 | Brosh |
| 5,108,819 A | 4/1992 | Heller |
| 5,147,519 A | 9/1992 | Legge |
| 5,306,917 A | 4/1994 | Black |
| 5,360,987 A | 11/1994 | Shibib |
| 5,439,575 A | 8/1995 | Thornton |
| 5,455,430 A | 10/1995 | Noguchi |
| 5,477,088 A | 12/1995 | Rockett |
| 5,567,975 A | 10/1996 | Walsh |
| 5,811,790 A | 9/1998 | Endo |
| 5,837,546 A | 11/1998 | Allen |
| 5,968,839 A | 10/1999 | Blatt |
| 6,009,632 A | 1/2000 | Douglas |
| 6,148,127 A | 11/2000 | Adams |
| 6,150,602 A | 11/2000 | Campbell |
| 6,282,960 B1 | 9/2001 | Samuels |
| 6,301,500 B1 | 10/2001 | Van Herk |
| 6,309,351 B1 | 10/2001 | Kurnik |
| 6,322,963 B1 | 11/2001 | Bauer |
| 6,344,616 B1 | 2/2002 | Yokokawa |
| 6,403,944 B1 | 6/2002 | MacKenzie |
| 6,518,168 B1 | 2/2003 | Clem |
| 6,567,158 B1 | 5/2003 | Falciai |
| 6,743,982 B2 | 6/2004 | Biegelsen |
| 6,787,052 B1 | 9/2004 | Vaganov |
| 6,805,809 B2 | 10/2004 | Nuzzo |
| 6,836,744 B1 | 12/2004 | Asphahani |
| 6,885,030 B2 | 4/2005 | Onozuka |
| 7,081,642 B2 | 7/2006 | Onozuka |
| 7,265,298 B2 | 9/2007 | Maghribi |
| 7,291,146 B2 | 11/2007 | Steinke |
| 7,293,353 B2 | 11/2007 | Matsuda |
| 7,337,012 B2 | 2/2008 | Maghribi |
| 7,487,587 B2 | 2/2009 | Vanfleteren |
| 7,491,892 B2 | 2/2009 | Wagner |
| 7,521,292 B2 | 4/2009 | Rogers |
| 7,525,304 B1 | 4/2009 | Feng |
| 7,552,031 B2 | 6/2009 | Vock |
| 7,557,367 B2 | 7/2009 | Rodgers |
| 7,593,086 B2 | 9/2009 | Jeong |
| 7,622,367 B1 | 11/2009 | Nuzzo |
| 7,633,761 B2 | 12/2009 | Kim |
| 7,732,012 B2 | 6/2010 | Hongu |
| 7,742,795 B2 | 6/2010 | Stone |
| 7,759,167 B2 | 7/2010 | Vanfleteren |
| 7,769,472 B2 | 8/2010 | Gerber |
| 7,838,964 B2 | 11/2010 | Carobolante |
| 7,871,661 B2 | 1/2011 | Maghribi |
| 7,884,540 B2 | 2/2011 | Sung |
| 7,909,971 B2 | 3/2011 | Nuzzo |
| 7,935,056 B2 | 5/2011 | Zbdefick |
| 7,960,246 B2 | 6/2011 | Flamand |
| 7,982,296 B2 | 7/2011 | Nuzzo |
| 8,008,575 B2 | 8/2011 | De Ceuster |
| 8,097,926 B2 | 1/2012 | De Graff |
| 8,107,248 B2 | 1/2012 | Shin |
| 8,198,621 B2 | 6/2012 | Rogers |
| 8,207,473 B2 | 6/2012 | Axisa |
| 8,217,381 B2 | 7/2012 | Rodgers |
| 8,252,191 B2 | 8/2012 | Heejoon |
| 8,367,035 B2 | 2/2013 | Rogers |
| 8,372,726 B2 | 2/2013 | De Graff |
| 8,389,862 B2 | 3/2013 | Arora |
| 8,394,706 B2 | 3/2013 | Nuzzo |
| 8,431,828 B2 | 4/2013 | Vanfleteren |
| 8,440,546 B2 | 5/2013 | Nuzzo |
| 8,536,667 B2 | 9/2013 | De Graff |
| 8,552,299 B2 | 10/2013 | Rodgers |
| 8,664,699 B2 | 3/2014 | Nuzzo |
| 8,679,888 B2 | 3/2014 | Rodgers |
| 8,729,524 B2 | 5/2014 | Rodgers |
| 8,754,396 B2 | 6/2014 | Rogers |
| 8,865,489 B2 | 10/2014 | Rodgers |
| 8,886,334 B2 | 11/2014 | Ghaffari |
| 8,905,772 B2 | 12/2014 | Rodgers |
| 2001/0012918 A1 | 8/2001 | Swanson |
| 2001/0021867 A1 | 9/2001 | Kordis |
| 2002/0026127 A1 | 2/2002 | Balbierz |
| 2002/0082515 A1* | 6/2002 | Campbell ................ A61B 5/01 600/549 |
| 2002/0095087 A1 | 7/2002 | Mourad |
| 2002/0128700 A1 | 9/2002 | Cross, Jr. |
| 2002/0151934 A1 | 10/2002 | Levine |
| 2003/0097165 A1 | 5/2003 | Krulevitch |
| 2003/0120271 A1 | 6/2003 | Burnside |
| 2003/0214408 A1 | 11/2003 | Grajales |
| 2003/0236455 A1 | 12/2003 | Swanson |
| 2004/0006264 A1 | 1/2004 | Mojarradi |
| 2004/0061543 A1 | 4/2004 | Nam |
| 2004/0085469 A1 | 5/2004 | Johnson |
| 2004/0092806 A1 | 5/2004 | Sagon |

(56) References Cited

U.S. PATENT DOCUMENTS

| | | |
|---|---|---|
| 2004/0106334 A1 | 6/2004 | Suzuki |
| 2004/0135094 A1 | 7/2004 | Niigaki |
| 2004/0138558 A1 | 7/2004 | Dunki-Jacobs |
| 2004/0149921 A1 | 8/2004 | Smyk |
| 2004/0178466 A1 | 9/2004 | Merrill |
| 2004/0243204 A1 | 12/2004 | Maghribi |
| 2005/0021103 A1 | 1/2005 | DiLorenzo |
| 2005/0037511 A1 | 2/2005 | Sharrock |
| 2005/0054939 A1 | 3/2005 | Ben-Ari |
| 2005/0107716 A1 | 5/2005 | Eaton |
| 2005/0113744 A1 | 5/2005 | Donoghue |
| 2005/0115308 A1 | 6/2005 | Koram |
| 2005/0136501 A1 | 6/2005 | Kuriger |
| 2005/0165303 A1 | 7/2005 | Kleen |
| 2005/0203366 A1 | 9/2005 | Donoghue |
| 2006/0038182 A1 | 2/2006 | Rodgers |
| 2006/0056161 A1 | 3/2006 | Shin |
| 2006/0068576 A1 | 3/2006 | Burdick, Jr. |
| 2006/0076561 A1 | 4/2006 | Hicki |
| 2006/0154398 A1 | 7/2006 | Qing |
| 2006/0286785 A1 | 12/2006 | Rogers |
| 2007/0027514 A1 | 2/2007 | Gerber |
| 2007/0104944 A1 | 5/2007 | Laude |
| 2007/0108389 A1 | 5/2007 | Makela |
| 2007/0122819 A1 | 5/2007 | Wu |
| 2007/0254468 A1 | 11/2007 | Burdick, Jr. |
| 2008/0041617 A1 | 2/2008 | Chen |
| 2008/0046080 A1 | 2/2008 | Vanden Bulcke |
| 2008/0157235 A1 | 7/2008 | Rodgers |
| 2008/0188912 A1 | 8/2008 | Stone |
| 2008/0193749 A1 | 8/2008 | Thompson |
| 2008/0204021 A1 | 8/2008 | Leussler et al. |
| 2008/0257586 A1 | 10/2008 | Chen |
| 2009/0001550 A1 | 1/2009 | Li |
| 2009/0088750 A1 | 4/2009 | Hushka |
| 2009/0105605 A1 | 4/2009 | Abreau |
| 2009/0107704 A1 | 4/2009 | Vanfleteren |
| 2009/0183986 A1 | 7/2009 | Johnson |
| 2009/0184254 A1 | 7/2009 | Miura |
| 2009/0204168 A1 | 8/2009 | Kallmyer |
| 2009/0215385 A1 | 8/2009 | Waters |
| 2009/0247909 A1 | 10/2009 | Mukumoto |
| 2009/0261828 A1 | 10/2009 | Nordmeyer-Massner |
| 2009/0273909 A1 | 11/2009 | Shin |
| 2009/0294803 A1 | 12/2009 | Nuzzo |
| 2009/0308455 A1 | 12/2009 | Kirscht |
| 2009/0317639 A1 | 12/2009 | Axisa |
| 2010/0002402 A1 | 1/2010 | Rodgers |
| 2010/0059863 A1 | 3/2010 | Rogers |
| 2010/0072577 A1 | 3/2010 | Nuzzo |
| 2010/0073669 A1 | 3/2010 | Colvin, Jr. |
| 2010/0087782 A1 | 4/2010 | Ghaffari |
| 2010/0116526 A1 | 5/2010 | Arora |
| 2010/0117660 A1 | 5/2010 | Douglas |
| 2010/0152619 A1 | 6/2010 | Kalpaxis |
| 2010/0176705 A1 | 7/2010 | Van Herpen |
| 2010/0178722 A1 | 7/2010 | De Graff |
| 2010/0188799 A1 | 7/2010 | Galvagni |
| 2010/0252840 A1 | 10/2010 | Ibbetson |
| 2010/0271191 A1 | 10/2010 | De Graff |
| 2010/0298895 A1 | 11/2010 | Ghaffari |
| 2010/0317132 A1 | 12/2010 | Rodgers |
| 2010/0321161 A1 | 12/2010 | Isabell |
| 2010/0324455 A1 | 12/2010 | Rangel |
| 2010/0327387 A1 | 12/2010 | Kasai |
| 2011/0011179 A1 | 1/2011 | Gustafsoon |
| 2011/0018838 A1 | 1/2011 | Lee |
| 2011/0034912 A1 | 2/2011 | De Graff |
| 2011/0054583 A1 | 3/2011 | Litt |
| 2011/0068672 A1 | 3/2011 | Hasnain |
| 2011/0114894 A1 | 5/2011 | Choi |
| 2011/0177332 A1 | 7/2011 | Park |
| 2011/0184320 A1 | 7/2011 | Shipps |
| 2011/0215931 A1 | 9/2011 | Callsen |
| 2011/0218756 A1 | 9/2011 | Callsen |
| 2011/0218757 A1 | 9/2011 | Callsen |
| 2011/0220890 A1 | 9/2011 | Nuzzo |
| 2011/0266561 A1 | 11/2011 | Rogers |
| 2011/0272181 A1 | 11/2011 | Koo |
| 2011/0277813 A1 | 11/2011 | Rodgers |
| 2011/0316120 A1 | 12/2011 | Rogers |
| 2012/0051005 A1 | 3/2012 | Vanfleteren |
| 2012/0052268 A1 | 3/2012 | Axisa |
| 2012/0065937 A1 | 3/2012 | De Graff |
| 2012/0083099 A1 | 4/2012 | Nuzzo |
| 2012/0092178 A1 | 4/2012 | Callsen |
| 2012/0105528 A1 | 5/2012 | Alleyne |
| 2012/0157804 A1 | 6/2012 | Rodgers |
| 2012/0157986 A1 | 6/2012 | Stone |
| 2012/0157987 A1 | 6/2012 | Steinke |
| 2012/0157988 A1 | 6/2012 | Stone |
| 2012/0157989 A1 | 6/2012 | Stone |
| 2012/0158101 A1 | 6/2012 | Stone |
| 2012/0165759 A1 | 6/2012 | Rogers |
| 2012/0172697 A1 | 7/2012 | Urman |
| 2012/0226130 A1 | 9/2012 | De Graff |
| 2012/0244848 A1 | 9/2012 | Ghaffari |
| 2012/0251824 A1 | 10/2012 | Hur |
| 2012/0256308 A1 | 10/2012 | Helin |
| 2012/0261551 A1 | 10/2012 | Rogers |
| 2012/0279762 A1 | 11/2012 | Hur |
| 2012/0320581 A1 | 12/2012 | Rogers |
| 2012/0327608 A1 | 12/2012 | Rodgers |
| 2013/0036928 A1 | 2/2013 | Rogers |
| 2013/0041235 A1 | 2/2013 | Rodgers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0225965 A1 | 8/2013 | Ghaffari |
| 2013/0245388 A1 | 9/2013 | Rafferty |
| 2013/0274562 A1 | 10/2013 | Ghaffari |
| 2013/0313713 A1 | 11/2013 | Arora |
| 2013/0316487 A1 | 11/2013 | De Graff |
| 2013/0320503 A1 | 12/2013 | Nuzzo |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 2/2014 | De Graff |
| 2014/0097944 A1 | 4/2014 | Fastert |
| 2014/0110859 A1 | 4/2014 | Rafferty |
| 2014/0140020 A1 | 5/2014 | Rodgers |
| 2014/0188426 A1 | 7/2014 | Fastert |
| 2014/0191236 A1 | 7/2014 | Nuzzo |
| 2014/0216524 A1 | 8/2014 | Rodgers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rodgers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |

FOREIGN PATENT DOCUMENTS

| | | |
|---|---|---|
| JP | 2003289136 | 10/2003 |
| JP | 2003297974 | 10/2003 |
| JP | 2005515795 | 6/2005 |
| JP | 2005177477 | 7/2005 |
| JP | 2005195495 | 7/2005 |
| JP | 2006507082 | 3/2006 |
| MY | P-020607 | 8/2012 |
| WO | WO 96/21245 | 7/1996 |
| WO | WO 01/66833 | 9/2001 |
| WO | WO 01/95787 | 12/2001 |
| WO | WO 01/98838 | 12/2001 |
| WO | WO 02/45100 | 6/2002 |
| WO | WO 02/45160 | 6/2002 |

(56) References Cited

FOREIGN PATENT DOCUMENTS

| | | |
|---|---|---|
| WO | WO 02/071137 | 9/2002 |
| WO | WO 02/073699 | 9/2002 |
| WO | WO 02/092778 | 11/2002 |
| WO | WO 03/030194 | 4/2003 |
| WO | WO 2004/000915 | 12/2003 |
| WO | WO 2004/001103 | 12/2003 |
| WO | WO 2004/047907 | 6/2004 |
| WO | WO 2004/062697 | 7/2004 |
| WO | WO 2004/107973 | 12/2004 |
| WO | WO 2005/000483 | 1/2005 |
| WO | WO 2005/012606 | 2/2005 |
| WO | WO 2005/029578 | 3/2005 |
| WO | WO 2005/033786 | 4/2005 |
| WO | WO 2005/033787 | 4/2005 |
| WO | WO 2005/054119 | 6/2005 |
| WO | WO 2005/099310 | 10/2005 |
| WO | WO 2005/104756 | 11/2005 |
| WO | WO 2005/106934 | 11/2005 |
| WO | WO 2005/122285 A2 | 12/2005 |
| WO | WO 2005/123114 | 12/2005 |
| WO | WO 2006/028996 | 3/2006 |
| WO | WO 2006/042287 | 4/2006 |
| WO | WO 2006/069323 | 6/2006 |
| WO | WO 2006/076711 | 7/2006 |
| WO | WO 2006/104069 | 10/2006 |
| WO | WO 2006/130558 | 12/2006 |
| WO | WO 2006/130721 | 12/2006 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/030960 A2 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO2010/046883 | 4/2010 |
| WO | WO 2010/056857 A2 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/002931 | 1/2011 |
| WO | WO2011/041507 | 4/2011 |
| WO | WO 2011/041727 A1 | 4/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/097163 | 7/2012 |
| WO | WO 2012/125494 A2 | 9/2012 |
| WO | WO 2012/158709 | 11/2012 |
| WO | WO 2012/166686 A2 | 12/2012 |
| WO | WO 2012/167096 | 12/2012 |
| WO | WO 2013/010113 | 1/2013 |
| WO | WO 2013/010171 A1 | 1/2013 |
| WO | WO 2013/022853 A1 | 2/2013 |
| WO | WO 2013/033724 A1 | 3/2013 |
| WO | WO 2013/049716 A1 | 4/2013 |
| WO | WO 2013/052919 A2 | 4/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006).

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

Ahn, H. et al., "Additive Soft Lithographic Patterning of Submicron and Nanometer-Scale Large Area Resists on Electronic Materials," *Nano Letters*, 5, 2533-2537 (2005).

Baca, A.J. et al., "Compact monocrystalline silicon solar modules with high voltage outputs and mechanically flexible designs," Energy Environ. Sci., 2010, 3, 208-211.

Baca, A.J. et al., "Printable single-crystal silicon micro/nanoscale ribbons, platelets and bars generated from bulk wafers," Adv. Func. Mater. 17, 3051-3062 (2007).

Bagnall, D.M. et al., "Photovoltaic Technologies," Energy Policy, 2008, 36, 4390.

Bergmann, R.B., "Crystalline Si thin-film solar cells: a review," AppL Phys. A 69, 187-194 (1999).

Biancardo, M. et al., "Characterization of microspherical semi-transparent solar cells and modules," Sol. Energy 81, 711-716 (2007).

Bossert, R.H. et al., "Thin Film Solar Cells: Technology Evaluation and Perspectives," ECN, May 2000.

Brendel, R., "Review of layer transfer processes for crystalline thin-film silicon solar cells," Jpn. J. Appl. Phys. 40, 4431-4439 (2001).

Brendel, R. et al., "Ultrathin crystalline silicon solar cells on glass substrates," Appl. Phys. Left. 70, 390-392 (1997).

Burgelman, M., et al., "Modeling Thin-Film PV Devices," Progress in Photovoltaics 12, 143-153 (2004).

Cahill, D.G. et al., "Thermal conductivity of epitaxial layers of dilute SiGe alloys," Phys. Rev. B, 71:23, 235202-1-4 (2005).

(56) References Cited

OTHER PUBLICATIONS

Campbell, P. et al., "Light Trapping Properties of Pyramidally Textured Surfaces," J. Appl. Phys. 62, 243-249 (1987).
Clugston, D.A. et al., "Modeling Free-Carrier Absorption in Solar Cells," Progress in Phoovoftaics 5, 229-236 (1997).
Clugston, D.A. et al., "PC1D version 5: 32-bit solar cell modeling on personal computers," Photovoltaic Specialist Conference, 1997, Conference Record of the Twenty-Sixth IEEE, 207-210.
Ebong, A. et al., "Rapid Thermal Processing of High Efficiency N-Type Silicon Solar Cells With Al back Junction," 14th World Conference on Photovoltaic Energy Conversion, Hawaii, USA; May 7-12, 2006.
Examination and Search Report. Corresponding to Malaysian Patent Application No. PI 20090622, Mailed Sep. 28, 2012.
Examination Report, Corresponding to European Application No. 07 841 968.6, dated Apr. 27, 2012, 6 pages.
Feng, N.-N. et al., "Design of Highly Efficient Light-Trapping Structures for Thin-Film Crystalline Silocon Solar Cells," IEEE Trans. Elect. Dev. 54, 1926-1933 (2007).
Final Office Action mailed Nov. 21, 2012 corresponding to U.S. Appl. No. 12/921,808.
First Office Action dated Mar. 5, 2013 from Chinese Patent Application No. 200980116128.1—includes English translation.
Green, M.A., "Crystalline and thin-film silicon solar cells: state of the art and future potential," Sol. Energy 74, 181-192 (2003).
Heine, C. et al., "Submicrometer Gratings for Solar-Energy Applications," Appl. Opt. 34, 24762482 (1995).
International Preliminary Report on Patentability for PCT Application No. PCT/US2010/060425, mailed Jun. 28, 2012.
International Search Report and Written Opinion corresponding to International Application No. PCT/US2012/058114 mailed Feb. 1, 2013.
International Search Report and Written Opinion dated Jul. 30, 2012, corresponding to International Patent Application No. PCT/US12/37973.
International Search Report and Written Opinion, Corresponding to International Application No. PCT/US12/59131, mailed Apr. 8, 2013.
International Search Report and Written Opinion, Corresponding to International Application No. PCT/US2012/039779, mailed Feb. 1, 2013.
International search report and written opinion, corresponding to International Application No. PCT/US12/46930, mailed Dec. 10, 2012.
International search report and written opinion, corresponding to International Application No. PCT/US2012/053701, mailed Jan. 15, 2013.
International Search Report corresponding to International Application No. PCT/US2012/028590, mailed Jun. 13, 2012.
J. Wang et al., "Binding and Diffusion of a Si Adatom Around the Type-A Step on Si(01) c4x2," Appl. Phys. Lett., 66:15, 1954 (1995).
J. Yoon et al., "Arrays of Monocrystalline Silicon Solar Micro-cells for Modules with Ultra-thin, Mechanically Flexible, Semi-transparent and Micro-optic Concentrator Designs," Materials Research Society (MRS) Symposium P: Photovoltaic Materials and Manufacturing Issues, Fall Meeting, Dec. 3, 2008—Abstract provided.
J. Yoon et al., "Ultrathin silicon solar microcells for semitransparent, mechanically flexible and microconcentrator module designs," Nat. Mater., 2008, 7, 907.
Jeon, S. et al., "Fabricating three dimensional nanostnictures using two photon lithography in a single exposure step," Optics Express, 14:6, 2300-23208 (2006).
Jeon, S. et al., "Optically fabricated three dimensional nanofluidic mixers for microfluidic systems," Nano Letters, 5:7, 1351-1356 (2005).
K. J. Weber et al., "A Novel Silicon Texturization Method Based on Etching Through a Silicon Nitride Mask," Progress in Photovoltaics: Research and Applications 13, 691-695 (2005).

Kazmerski, L.L. et al., "Solar photovoltaics R&D at the tipping point: A 2005 technology overview." J. Elect. Spec. Rel. Phenom. 150, 105-135 (2006).
Kerschaver, E. V. et al., "Back-contact Solar Cells: A Review," Prog. Photovolt. 14, 107-123 (2006).
Kunnavakkam, M.V. et al., "Low-cost, low-loss microlens arrays fabricated by soft-lithography replication process," Appl. Phys. Lett. 82, 1152-1154 (2003).
Lee, H.H. et al., "Fabrication of Large Area Stamps, Moulds, and Conformable Photomasks for Soft Lithography," Journal of Nanoengineering and Nanosystems 218, 105 (2005).
Lee, K.J. et al., "Bendable GaN High Electron Mobility Transistors on Plastic Substrates," Journal of Applied Physics 100, 124507 (2006).
Lei, C. et al., "Grain Boundary Compositions in Cu(InGa)Se2," J. Appl. Phys., 101:2, 24909-1-7 (2007).
Lei, C. et al., "Void formation and surface energies in Cu(InGa)Se2," J. Appl. Phys. 100:7, 073518 (2006).
Liao, D. et al., "Cu depletion at the CuInSe2 Surface," Appl. Phys. Lett., 82:17, 2829-2831 (2003).
Liu, Z.X. et al., "A concentrator module of spherical Si solar cell," Sol. Energy Mater. Sol. Cells 91, 1805-1810 (2007).
Love, J.C. et al., "Self-Assembled Monolayers of Thiolates on metals as a Form of Nanotechnology," Chem. Rev., 105, 1103-1169 (2005).
M.E. Stewart et al., "Quantitative Multispectral Miosensing and 1-D Imaging Using Quasi-3D Plasmonic Crystals," Proc. Nat. Acad. Sci., 103, 17143-17148 (2006).
Mack, S. et al., "Mechanically flexible thin-film transistors that use ultrathin ribbons of silicon derived from bulk wafers," Appl. Phys. Lett., 88, 213101 (2006).
Malyarchuk, V. et al., "High performance plasmonic crystal sensor formed by soft nanoimprint lithography," Optics Express, 13:15, 5669-5675 (2005).
Mercaldo, L.V. et al., "Thin film silicon photovoltaics: Architectural perspectives and technological issues," App. Energy, 2009, 86, 1836.
Minemoto, T. et al., "Fabrication of spherical silicon crystals by dropping method and their application to solar cells," Jpn. J. Appl. Phys. 46, 4016-4020 (2007).
Nelson, B. et al., "Amorphous and Thin-Film Silicon," NCPV and Solar Program Review, NREL/CD-520-33586, 583-585, 2003.
Nelson, B. et al., "Project Summary of the NREL Amorphous Silicon Team," NCPV and Solar Program Review, NREL/CD-520-33586, 825-828, 2003.
Niggemann, M. et al., "Realization of Ultrahigh Photovoltaics with Organic Photovoltaic Nanomodules," Adv. Mater. 2008, 20, 4055.
Notice of Allowance corresponding to Korean Patent Application No. 10-20102-7010094, dated Feb. 25, 2013—includes English translation.
Notice of Allowance, U.S. Appl. No. 12/398,811 mailed May 24, 2013.
Notice of Final Rejection for Japanese Patent Application No. 2006-16159, dated Apr. 16, 2013.
Notice of final rejection for Japanese Patent Application No. 2007-515549, dated Sep. 19, 2012.
Notice of Preliminary Rejection corresponding to Korean Patent Application No. 10-2007-7000216, dated Feb. 21, 2013—includes English translation.
Notice of Preliminary Rejection corresponding to Korean Patent Application No. 10-2012-7030789, dated Feb. 25, 2013—includes English translation.
Notice of reason for rejection, corresponding to Japanese Patent Application No. P2009-546361, Dispatched Jul. 3, 2012—includes English translation.
Notice of reasons for rejection, corresponding to Japanese Patent Application No. P2006-165159, dispatched Apr. 24, 2012—includes English translation.
Notice of Reasons of Rejection corresponding to Japanese Patent Application No. 2009-527564, mailed Jan. 29, 2013.
Notification of Grant of Patent Right and Notice of Registration corresponding to Chinese Patent App. No. 200780041127.6 issued Dec. 26, 2012.

(56) References Cited

OTHER PUBLICATIONS

Office Action for U.S. Appl. No. 13/441,598 mailed Jan. 14, 2013.
Office Action, Corresponding to Chinese Patent Application No. 2009801161280.1, mailed Mar. 5, 2013.
Office action, corresponding to U.S. Appl. No. 12/686,076, mail date Jun. 6, 2012.
Office Action, Corresponding to U.S. Appl. No. 13/441,618, mailed May 23, 2013.
Office Action, corresponding to U.S. Appl. No. 12/398,811, mailed Nov. 26, 2012.
Office Action, Corresponding to U.S. Appl. No. 12/778,588 mailed Jan. 8, 2013.
Office Action, Corresponding to U.S. Appl. No. 13/120,486, mailed Apr. 12, 2013.
Orega, P. et al., "High Voltage Photovoltaic Mini-modules," Progr. Photovolt.: Res. Appl., 2008, 16, 369.
Pizzini, S., "Bulk solar grade silicon: how chemistry and physics play to get a benevolent microstructured material," Appl. Phys. A: Mater. Sci. Process., 2009, 96, 171.
R. Rockett et al., "Prediction of dopant ionization energies in silicon: The importance of strain," Physical Review B, 6823:23, 3208 (2003).
Rockett, A. et al., "The effect of Na in polycrystalline and single crystal CuIn1-xGAXSe2," Thing Solid films, 480-1, 2-7 (2005).
Rockett, A. et al., "A Monte Carlo simulation of the growth of Si(001)2x1: adatom/SA step interactions and growth mechanisms," Surf. Sci., 312, 201-212 (1994).
Rockett, A. et al., "Near-surface Defect Distributions in Cu(In,Ga)Se2," Thin Solid Films, 431-2, 301-306 (2003).
Roedern, B., "Status of Amorphous and Crystalline Thin-Film Silicon Solar Cell Activities," NCPV and Solar Program Review, NREL/CD-520-33586, 552-555, 2003.
Ruby, D.S. et al., "Rie-texturing of multicrystalline silicon solar cells," Solar Energy Materials & Solar Cells 74, 133-137 (2002).
Second substantive office action, corresponding to Chinese Patent Application No. 20100519400.5, issued on Oct. 30, 2012.
Sha, A. et al., "Recent progress on microcrystalline solar cells.," Photovoltaic Specialists Conference, Conference Record of the Twenty-Sixth IEEE, 569-574 (1997).
Sinton, R.A. et al., "27.5-Percent Silicon Concentrator Solar-Cells," IEEE Elect. Dev. Lett. 7, 567-569 (1986).
Sobajima et al., "Microstructures of high-growth-rate (up to 8.3 nm/s) microcrystalline silicon photovoltaic layers and their influence on the photovoltaic performance of thin-film solar cells," J. Non-Cryst. Solids, 2008, 354, 2407.
Sun, Y. et al., "Gigahertz Operation in Mechanically Flexible Transistors on Plastic Substrates," Applied Physics Letters 88, 183509 (2006).
Sun, Y. et al., "Printed Arrays of Aligned GaAs Wires for Flexible Transistors, Diodes and Circuits on Plastic Substrates," Small 2(11), 1330-1334 (2006).
Sun, Y. et al., "Top Down Fabrication of Semiconductor Nanowires With Alternating Structures Along Their Transverse and Longitudinal Axes," Small 1(11), 1052-1057 (2005).
Supplementary European Search Report, dated Jun. 15, 2012, corresponding to European Patent Application No. 09 71 6695.
Taguchi, M. et al., "HIT TM cells—High efficiency crystalline Si cells with novel structure," Prog. Photovolt. 8, 503-513 (2000).
Verlinden, P.J. et al., "Silver (R) solar cells: A new thin-crystalline silicon photovoltaic technology," Sol. Energy Mater. Sol. Cells 90, 3422-3430 (2006).
Weber, K.J. et al., "A Novel-Low Cost, High Efficiency Micromachined Silicon Solar Cell," IEEE Electron Device Letters, vol. 25, No. 1, 37-39 (2004).
Wenham, S.R. et al., "Buried contact silicon solar cells," Solar Energy Materials and Solar Cells, 34, 101-110 (1994).
Yamamoto, K. et al., "Thin-film poly-Si solar cells on glass substrate fabricated at low temperature," Applied Physics A: Materials Science & Processing 69, 179-185 (1999).
Zhao et al., "24.5% efficiency silicon PERT cells on MCZ substrates and 24.7% efficiency PERL cells on FZ substrates," Prog. Photovolt. 7, 471-474 (1999).
U.S. Appl. No. 12/921,808, filed Mar. 12, 2009, B. Litt, Flexible and Scalable Sensor Arrays for Recording and Modulating Physiologic Activity.
U.S. Appl. No. 12/968,637, filed Dec. 15, 2010, J. Rodgers, High-Speed, High-Resolution Electrophysiology In-Vivo Using Conformal Electronics.
U.S. Appl. No. 13/492,636, filed Jun. 8, 2012, J. Rodgers, Flexible and Stretchable Electronic Systems for Epidermal Electronics.
U.S. Appl. No. 14/155,010, filed Jan. 14, 2014, R. Nuzzo, Methods and Devices for Fabricating and Assembling Printable Semiconductor Elements.
U.S. Appl. No. 14/173,525, filed Feb. 5, 2014, J. Rodgers, Arrays of Ultrathin Silicon Solar Microcells.
U.S. Appl. No. 14/220,910, filed Mar. 20, 2014, J. Rodgers, Controlled Buckling Structures in Semiconductor Interconnnects and Nanomembranes for Stretchable Electronics.
U.S. Appl. No. 14/220,923, filed Mar. 20, 2014, J. Rogers, Stretchable Form of Single Crystal Silicon for High Performance Electronics on Rubber Substrates.
U.S. Appl. No. 14/479,100, filed Sep. 5, 2014, J. Rodgers, Printed Assemblies of Ultrathin, Microscale Inorganic Light Emitting Diodes for Deformable and Semitransparent Displays.
U.S. Appl. No. 14/521,319, filed Oct. 22, 2014, J. Rodgers, Stretchable and Foldable Electronic Devices.
U.S. Appl. No. 12/575,008, filed Oct. 7, 2009, R. Ghaffari et al., Catheter Balloon Having Stretchable Circuitry and Sensor Array.
U.S. Appl. No. 12/972,073, filed Dec. 17, 2010, G. Callsen et al., Methods and Apparatus for Conformal Sensing of Force and/or Acceleration At a Person's Head.
U.S. Appl. No. 12/976,607, filed Dec. 22, 2010, G. Callsen et al., Methods and Apparatus for Conformal Sensing of Change in Motion At an Arbitrarily-Shaped Surface.
U.S. Appl. No. 12/976,814, filed Dec. 22, 2010, G. Callsen et al., Methods and Apparatus Having Power Control Features for Conformal Sensing of Change in Motion of a Body Part.
U.S. Appl. No. 12/973,833, filed Dec. 22, 2010, G. Callsen et al., Methods and Apparatus for Assessing Head Trauma Based on Conformal Sensing of Force and/or Change in Motion of a Person's Head.
U.S. Appl. No. 13/082,388, filed Apr. 7, 2011, B. De Graff et al., Methods and Apparatus for Measuring Technical Parameters of Equipment, Tools and Components Via Conformal Electronics.
U.S. Appl. No. 14/004,408, filed Mar. 9, 2012, R. Ghaffari et al., Integrated Devices to Facilitate Quantitative Assays and Diagnostics.
U.S. Appl. No. 13/481,843, filed May 27, 2012, B. Elolampi et al., Electronic, Optical and/or Mechanical Apparatus and Systems and Methods for Fabricating Same.
U.S. Appl. No. 13/499,626, filed Jun. 12, 2012, R. Ghaffari et al., Protective Cases With Integrated Electronics.
U.S. Appl. No. 13/550,254, filed Jul. 16, 2012, J. Carbeck et al., Detection of a Force on a Foot or Footwear.
U.S. Appl. No. 13/568,022, filed Aug. 6, 2012, R. D'angelo et al., Catheter Balloon Methods and Apparatus Employing Sensing Elements.
U.S. Appl. No. 13/603,290, filed Sep. 4, 2012, C. Rafferty et al., Electronics for Detection of a Condition of Tissue.
U.S. Appl. No. 13/631,739, filed Sep. 28, 2012, C. Rafferty et al., Electronics for Detection of a Property of a Surface.
U.S. Appl. No. 13/646,613, filed Oct. 5, 2012, R. Ghaffari et al., Cardiac Catheter Employing Conformal Electronics for Mapping.
U.S. Appl. No. 13/747,826, filed Jan. 23, 2013, B. De Graff et al., Methods and Applications of Non-Planar Imaging Arrays.
U.S. Appl. No. 13/767,262, filed Feb. 14, 2013, W. Arora et al., Extremely Stretchable Electronics.
U.S. Appl. No. 13/640,280, filed Feb. 25, 2013, B. De Graff et al., Methods and Apparatus for Measuring Technical Parameters of Equipment, Tools and Components Via Conformal Electronics.
U.S. Appl. No. 13/843,873, filed Mar. 15, 2013, Y. Hsu, Strain Isolation Structures for Stretchable Electronics.

(56) References Cited

OTHER PUBLICATIONS

U.S. Appl. No. 13/844,399, filed Mar. 15, 2013, Y. Hsu, Strain Relief Structures for Stretchable Interconnects.
U.S. Appl. No. 13/844,399, filed Mar. 15, 2013, S. Fastert et al., Conformal Electronics Integrated With Apparel.
U.S. Appl. No. 13/844,508, filed Mar. 15, 2013, S. Fastert et al., Monitoring Hit Count for Impact Events.
U.S. Appl. No. 13/844,635, filed Mar. 15, 2013, R. Ghaffari et al., Catheter Balloon Having Stretchable Integrated Circuitry and Sensor Array.
U.S. Appl. No. 13/844,638, filed Mar. 15, 2013, C. Rafferty et al., Embedding Thin Chips in Polymer.
U.S. Appl. No. 13/844,677, filed Mar. 15, 2013, S. Lee et al., Catheter Device Including Flow Sensing.
U.S. Appl. No. 13/844,767, filed Mar. 15, 2013, R. Ghaffari et al., Catheter Balloon Employing Force Sensing Elements.
U.S. Appl. No. 13/963,778, filed Aug. 9, 2013, B. De Graff et al., Systems, Methods and Devices Having Stretchable Integrated Circuitry for Sensing and Delivering Therapy.
U.S. Appl. No. 14/093,329, filed Nov. 29, 2013, R. Ghaffari, Systems, Methods, and Devices Having Stretchable Integrated Circuitry for Sensing and Delivering Therapy.
U.S. Appl. No. 14/147,347, filed Jan. 3, 2014, R. Ghaffari et al., Catheter or Guidewire Device Including Flow Sensing and Use Thereof.
U.S. Appl. No. 14/276,413, filed May 13, 2014, Y. Hsu et al., Conformal Electronics Including Nested Serpentine Interconnects.
U.S. Appl. No. 14/294,808, filed Jun. 3, 2014, I. Kacyvenski et al., Motion Sensor and Analysis.
U.S. Appl. No. 14/311,686, filed Jun. 23, 2014, J. Fenuccio et al., Band With Conformable Electronics.
U.S. Appl. No. 14/451,981, filed Aug. 5, 2014, X. Li et al., Flexible Temperature Sensor Including Conformable Electronics.
U.S. Appl. No. 14/488,544, filed Sep. 17, 2014, W. Arora et al., Extremely Stretchable Electronics.
U.S. Appl. No. 14/510,868, filed Oct. 9, 2014, B. Ives, Utility Gear Including Conformal Sensors.
U.S. Appl. No. 29/506,439, filed Oct. 15, 2014, X. Li et al., Electronic Device Having Antenna.
U.S. Appl. No. 14/524,817, filed Oct. 27, 2014, X. Li et al., Conformal Electronic Devices.
U.S. Appl. No. 14/588,765, filed Jan. 2, 2015, S. Lee et al., Integrated Devices for Low Power Quantitative Measurements.

* cited by examiner

SYSTEMS, METHODS, AND DEVICES USING STRETCHABLE OR FLEXIBLE ELECTRONICS FOR MEDICAL APPLICATIONS

CROSS REFERENCE TO RELATED APPLICATIONS

This application is a division of U.S. patent application Ser. No. 12/636,071, filed Dec. 11, 2009, now U.S. Pat. No. 8,886,334, issued Nov. 11, 2014, which claims the benefit of the following U.S. Provisional Application Ser. No. 61/121,568 entitled "Endoscopy Device" filed Dec. 11, 2008; Ser. No. 61/121,541 entitled "Nerve Bundle Prosthesis" filed Dec. 11, 2008; and Ser. No. 61/140,169 entitled "Body Tissue Screener" filed Dec. 23, 2008, the entirety of each of which is incorporated herein by reference. Further, U.S. patent application Ser. No. 12/636,071 is a continuation-in-part of and claims the benefit of U.S. Nonprovisional patent application Ser. No. 12/616,922 entitled "Extremely Stretchable Electronics" filed Nov. 12, 2009, now U.S. Pat. No. 8,389,862, issued Mar. 5, 2013, the entirety of which is incorporated herein by reference. Nonprovisional patent application Ser. No. 12/616,922 claims the benefit of U.S. Provisional Application No. 61/113,622 entitled "Extremely Stretchable Interconnects" filed on Nov. 12, 2008, the entirety of which is incorporated herein by reference. Also, Nonprovisional patent application Ser. No. 12/616,922 is a continuation-in-part of, and claims the benefit of copending U.S. Nonprovisional application Ser. No. 12/575,008 entitled "Catheter Balloon Having Stretchable Integrated Circuitry and Sensor Array" filed on Oct. 7, 2009, the entirety of which is incorporated herein by reference. Nonprovisional application Ser. No. 12/575,008 claims priority to U.S. Provisional Application No. 61/103,361 entitled "Catheter Balloon Sensor and Imaging Arrays", filed Oct. 7, 2008, the entirety of which is incorporated herein by reference; and U.S. Provisional Application No. 61/113,007 entitled "Catheter Balloon with Sensor and Imaging Array", filed Nov. 10, 2008 the entirety of which is incorporated herein by reference.

FIELD OF THE INVENTION

The present invention relates to systems, apparatuses, and methods utilizing expandable or stretchable integrated circuitry and sensor arrays on expandable, flexible or stretchable substrates in or on medical devices.

BACKGROUND OF THE INVENTION

High quality medical sensing and imaging data has become important in the diagnoses and treatment of a variety of medical conditions include those related to conditions associated with the digestive system, conditions related to the cardiocirculatory system, injuries to the nervous system, cancer, and the like. Current sensing and therapeutic devices suffer from various disadvantages due to a lack of sophistication related to the sensing, imaging, and therapeutic functions. One of these disadvantages is that such devices are unable to achieve direct or conformal contact with the part of the body being measured or treated. The inability to achieve direct or conformal contact of such devices is partially attributable to the rigid nature of the devices and accompanying circuitry. This rigidity prevents devices from coming into confirming and/or direct contact with human tissue, which as readily apparent may change shape and size, and may be soft, pliable, curved, and/or irregularly shaped. Such rigidity thus compromises accuracy of measurements and effectiveness of treatment. Thus, devices, systems and methods, which employ flexible and/or stretchable systems would be desirable.

Examples of areas that are amenable to such flexible and/or stretchable approaches include, endoscopy, vascular examination and treatment, neurological treatment and examination, and tissue screening.

As an example, endoscopic imaging of the gastrointestinal (GI) tract is essential for effective diagnosis and treatment of a variety of GI disorders, including inflammations, ulcers, abscesses, and cancer detection. By way of elaboration, endoscopic imaging capsules may offer certain advantages over traditional endoscopes for a variety reasons: they involve minimal patient discomfort and can image regions along the GI tract that are inaccessible with traditional endoscopes. All components are encapsulated within an ellipsoid body whose volume must be small enough to be swallowed and ingested. Consequently, there is an added benefit to minimizing the volume of these ingestible capsules. There also are a variety of features, including power storage and imaging quality that can be significantly improved if the spatial layout of the components within the capsule could be optimized. Additionally, optical imagers in current endoscopic capsules generally have a planar geometry, with the imager aligned with the optical center of the lens. This geometry is subject to intrinsic limitations such as aberrations, peripheral distortion and illumination inhomogeneity. Stretchable and/or flexible circuitry could mitigate some of the disadvantages described above with respect to capsule endoscopy, as well as traditional endoscopic devices.

Spinal cord and other complex brain or nerve injury is a major cause of disability, death and suffering, and to date there are few effective treatments. As an example, the complexity of the spinal cord, consisting of thousands of nerve fibers and both dark and gray matter, makes surgical repair extremely difficult, with a high degree of additional irreversible injury. Therefore, much attention has been focused on reducing scarring and stimulating regeneration with pharmaceuticals or stem cells. Bionic solutions have also gained some interest. Experiments have been conducted on electrical sensing and stimulation of ascending and descending bundles, demonstrating that electrical impulses can be used to provide some level of function. Separately, there are devices in clinical use which perform electrical stimulation of nerves in and near the spine to treat chronic pain, but these are not intended to restore nerve function. Combining the benefits of these existing devices may not go far enough toward dramatically improving spinal cord therapies due to some of the limitation mentioned above. Accordingly, there is a need for dynamically configurable and conformable devices, systems, and methods that minimize the risk of further injury while providing increased function to the damaged nerves.

Another example where the benefits of flexible/and or stretchable devices are needed involves tissue screening. While tissue screening procedures are of paramount important for early detection, evaluation, and subsequent treatment of cancer, clinical diagnostic methods, such as mammography and ultrasound imaging are expensive and require trained personnel. Thus, almost two-thirds of cancers are initially detected by palpatory (i.e. tactile sense of touch) self-examination. Palpatory examination is a qualitative technique taught to women, for example, as a preclinical test for breast cancer to be conducted at the home. It is well known that cancerous tissue undergoes significant changes in mechanical properties with respect to healthy tissue. Local lesions in breast cancer tissue are stiffer by up to 2-fold. Although self-examinations of breast tissue have facilitated early detection of hardened legions, indicative of tumor growth, the qualitative nature of these tests makes it difficult to ascertain any quantitative data important to clinicians or to analyze trends over time. Because the self-examination approach generally involves manually detecting the location, size, shape, and density of lesions by conforming fingertips around the lesion, a device capable of achieving conformal contact with the tissue of interest that can quantify and record the intrinsic mechanical properties of tissue can have a significant impact on the way breast cancer screening is currently performed at the home and in the clinical setting as a supplement to mammography and ultrasound.

Finally, detection and treatment of conditions in the cardiovascular system would greatly benefit from approaches that increase the quality of data generated by sensing devices, techniques, and methods. Currently, such sensing techniques devices and methods are greatly limited by their inability to achieve close, direct, and or conformal contact with the area of interest. Therefore, gathering data relating to the electrical, chemical, and other physical activity or condition of the tissue is compromised.

Stretchable and/or flexible electronics can mitigate or resolve many of the shortcomings described above. Such techniques can be applied to the areas above, or to any area of physiological sensing, medical detection, or medical diagnostics that would be improved by enhanced contact with sensing or therapeutic devices.

SUMMARY OF THE INVENTION

Methods, systems, and devices are disclosed herein which employ stretchable/and or flexible circuitry for physiological sensing, detection of health-related parameters, and delivery of therapeutic measures. In embodiments, the circuitry is disposed on a stretchable, flexible, expandable, and/or inflatable substrate. In embodiments, circuitry comprises electronic devices, which may be active devices, in electronic communication with one another and programmed or configured to generate output and cause an output facility to display such output, deliver therapeutic measures, generate data regarding physiological parameters and/or make determinations of a health-related condition. Embodiments of the invention may include a storage facility in communication with the processing facility. The processing facility may cause at least one of data generated by the active devices and the output data to be stored in the storage facility and may generate output data related to the stored data. The processing facility may cause at least one of data generated by the active devices and the output data to be aggregated and may generate output data related to the aggregated data.

In embodiments, the methods and systems herein may comprise a neural prosthesis device. Thus, in an aspect of the invention, methods, devices and systems include an apparatus that may include a substrate on which is disposed circuitry that may include an array of recording electrodes for receiving signals from a plurality of nerve sources when a portion of the electrodes is in electrical contact with the plurality of nerve sources and an array of stimulating electrodes; and a processing facility in electronic communication with the arrays of electrodes, and being configured to receive signals from the recording electrodes and determine a pattern of stimulation signals to be effected by the stimulating electrodes.

In the aspect mentioned above and in other embodiments, the electrical contact may comprise physical contact. Further in embodiments, the apparatus may include a multiplexer configured to match the signals from the nerve sources and cause the stimulating electrodes to dispatch a corresponding signal to a second plurality of nerves. The apparatus may include a user interface to adjust the pattern of stimulation signals, which may be dynamically configurable.

In embodiments, the substrate is an inflatable body which may be a disk or a balloon.

In the aspect mentioned above, the processing facility is further configured to generate data related to the electrical conductivity of the nerve sources. The processing facility may be in electronic communication with an output facility and may cause the output facility to generate a map based on the data related to the electrical conductivity of the nerve sources.

In the aspect mentioned above and in other embodiments, the circuitry may be encapsulated with a thin polymer layer. The circuitry may be stretchable up to 300%. The electrodes may located discretely from one another. The circuitry may comprise stretchable electrical interconnects which may electrically connect the electrodes.

In embodiments, the circuitry may include sensors that may include any of temperature sensors, contact sensors, light or photo detectors, ultra sound emitters and transceivers, pressure sensors, or the like.

In this aspect mentioned in conjunction with the neural prosthesis and with respect to other embodiments disclosed herein, the substrate may include a reservoir in communication with the surface of the substrate, and the circuitry may be configured to open valves operable to release a drug contained within the reservoir where the circuitry may cause the valves to release the drug in a controlled manner.

In other embodiments, the methods and systems herein may comprise an inflatable device for sensing tissues.

Thus, in another aspect of the invention, methods and systems include an apparatus that may include an inflatable substrate on which may be disposed circuitry that remains functional upon inflation of the substrate and may include an array of active devices that may include sensing devices for detecting data indicative of a parameter associated with a tissue; and a processing facility in electronic communication with the circuitry, receiving data indicative of a parameter associated with the tissue; and an output facility in electronic communication with the processing facility, where the processing facility may be configured to generate output data associated with the tissue and to cause the output facility to generate output data.

In the aspect mentioned above for sensing tissues and in other embodiments, the processing facility may receive data generated by the sensing devices and produce an image of the tissue. In embodiments, the sensing devices are configured to be in an active matrix which may be operated by circuitry which may include at least one of an amplifier and a logic circuit. Further, the apparatus may include a multiplexer which may be located at the base of a catheter guide wire coupled to the substrate which may be a balloon.

In embodiments, the processing facility may be within the circuitry. In other embodiments, the processing facility may be separate from the circuitry.

In this aspect mentioned above with respect to sensing tissue parameters, the output data related to the tissue may be a map which may include a map of electrical activity of the tissue. The output data may comprise data related to temperature heterogeneity present in arterial plaque. Further, the output data may comprise an indication of plaque type.

In aspects mentioned above and in other embodiments, the circuitry may comprise a therapeutic facility which may be configured to ablate the tissue. The circuitry may comprise light emitting electronics. The circuitry may comprise an array of photodetectors in communication with the processing facility where the processing facility may be configured to generate image of the tissue and to cause the output facility to output an image which may be high resolution. Where the circuitry is delivered via a catheter having a guide wire, the guide wire may include a light source, which may be an optical fiber, to provide light to the photodetectors.

In embodiments, the tissue of interest may include any of a pulmonary vein, a septal wall of a heart, an atrial surface of a heart, and a ventricular surface of a heart.

In another aspect of the invention, methods and systems include a method of detecting parameters associated with a lumen in the body of an individual. The method may include inserting an un-inflated balloon catheter into the lumen, the balloon catheter having a stretchable balloon having stretchable circuitry applied thereto, the stretchable circuitry comprising sensing devices; directing the sensing devices to be in an area of interest within the lumen; and inflating the balloon and causing the sensing devices to come into conformal contact with surface of the area of interest within the lumen.

With respect to embodiments mentioned above and others disclosed herein, the invention may comprise sensing devices to generate data indicative of a parameter of the area of interest when the sensing devices are in conformal contact with the area of interest. Like other embodiments, the generated data may be used to produce any of an image of the area of interest and a map of the area of interest where the map may include data indicative of the electrical activity of the area of interest.

In another aspect of the invention, methods and systems include a method of detecting parameters associated with a lumen in the body of an individual. The method may include inserting an un-inflated balloon catheter into the lumen, the balloon catheter having a stretchable balloon having stretchable circuitry applied thereto, the stretchable circuitry comprising sensing devices; directing the sensing devices to be in an area of interest within the lumen; and inflating the balloon and causing the sensing devices to come into partial sensing contact with surface of the area of interest within the lumen.

In yet an aspect of the invention, methods and systems include a method of detecting a parameter of a tissue. The method may include placing an array of active sensing devices in conformal contact with the tissue, the array comprising stretchable circuitry; generating data with the sensing devices; and determining the parameter from the generated data.

The methods and systems herein may comprise a tissue screening device.

Thus, in still yet another aspect of the invention, methods and systems include a tissue screening device, including a stretchable substrate conformable to the contour of an area of interest on a body on which may be affixed stretchable circuitry which may include an array of active devices; a processing facility in electronic communication with the array of active devices; and an output facility in electronic communication with the processing facility, wherein the processing facility may be programmed to generate output data based on data generated by the array of active devices and to cause the output facility to display the output data.

In this aspect, as with others the substrate may be inflatable. The substrate may be affixed to a bra.

In embodiments, the sensor devices include pressure sensors, which may include an on-off switch coupled to the pressure sensor to indicate whether the pressure sensor has been activated.

In the tissue screening embodiments and in others mentioned above, the processing facility may receive data generated by the ultrasound emitters and receivers and may produce an image of the tissue.

In embodiments of the invention, the output data comprises a contour map of the area of interest.

In an aspect of the invention, methods and systems include a method of examination for cancerous or suspicious tissue which may include providing a subject with a wearable device conforming to an area of interest on subject's body, the wearable device comprising a stretchable array of pressure sensors; exerting a manual force on the wearable device sufficient to activate the array of pressure sensors; receiving data from the pressure sensors; and characterizing the tissue in the area of interest based on the received data. Further in this aspect, instructing the subject to exert the manual force. In this aspect, the wearable device may be inflatable. In this aspect, the wearable device may be affixed to a bra. In embodiments, the wearable device may be a sheet.

The methods and systems herein may comprise an endoscopy device.

Thus, in another aspect of the invention, methods and systems include an endoscopic device, including a housing to and within which may be mounted curvilinear circuitry which may include a focal plane array generating visual data; a transmission facility in electronic communication with the circuitry configured to wirelessly transmit the visual data; and an output facility receiving and displaying the visual data.

In this aspect, the housing may be a capsule. The circuitry, transmission facility, and the output facility may be mounted within the capsule. In this aspect, the housing may be located at a tip of the endoscopic device. In this aspect, the circuitry further comprises light emitting electronics. In this aspect, the circuitry may be configured to illuminate select portions of the light emitting electronics. the circuitry may be affixed to an exterior surface of the housing, or the circuitry may be affixed to an interior surface of the housing.

Further in embodiments related to endoscopy and with respect to other embodiments herein, the circuitry may include sensing devices which may be capable of generating any of data related to enzymatic activity and data related to chemical activity.

In this embodiment and others herein, the circuitry comprises sensing devices and a processing facility receiving data from the sensing devices, the processing facility in electronic communication with the output facility. The processing facility may cause the output facility to display information related to data generated by the sensing devices.

Further in this aspect and others, including a processing facility within the circuitry. Further in this aspect, including a processing facility separate from the circuitry.

In this aspect, the visual data is an image. In this aspect, the visual data may be a map.

The methods and systems herein may comprise a dynamically configurable sheet of electronic devices.

Thus, in another aspect of the invention, methods and systems include a configurable sheet of electronic devices, a substantially flat substrate on which may be disposed stretchable circuitry containing an array of electronic devices in electronic communication with one another; and a processing facility capable of polling the array of electronic devices to determine a first set of information related to the identity and location of each electronic device in the array, the processing facility configured to adjust the operation of the array based upon information related to a second set of information related to the identity and location of each electronic device in the array. In this aspect, the second set of information is received after the circuitry is reshaped, where the reshaping may be caused by cutting the circuitry.

In embodiments, circuitry may include an array of electronic devices may include sensor devices which may generate data of a tissue of interest when the sheet is at least one of partial electrical contact and partial conformal contact with the tissue of interest.

BRIEF DESCRIPTION OF THE DRAWINGS

The present invention will become more fully apparent from the following description and appended claims, taken in conjunction with the accompanying figures. Understanding that these figures merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying figures in which:

DETAILED DESCRIPTION OF THE INVENTION

Figure 1:
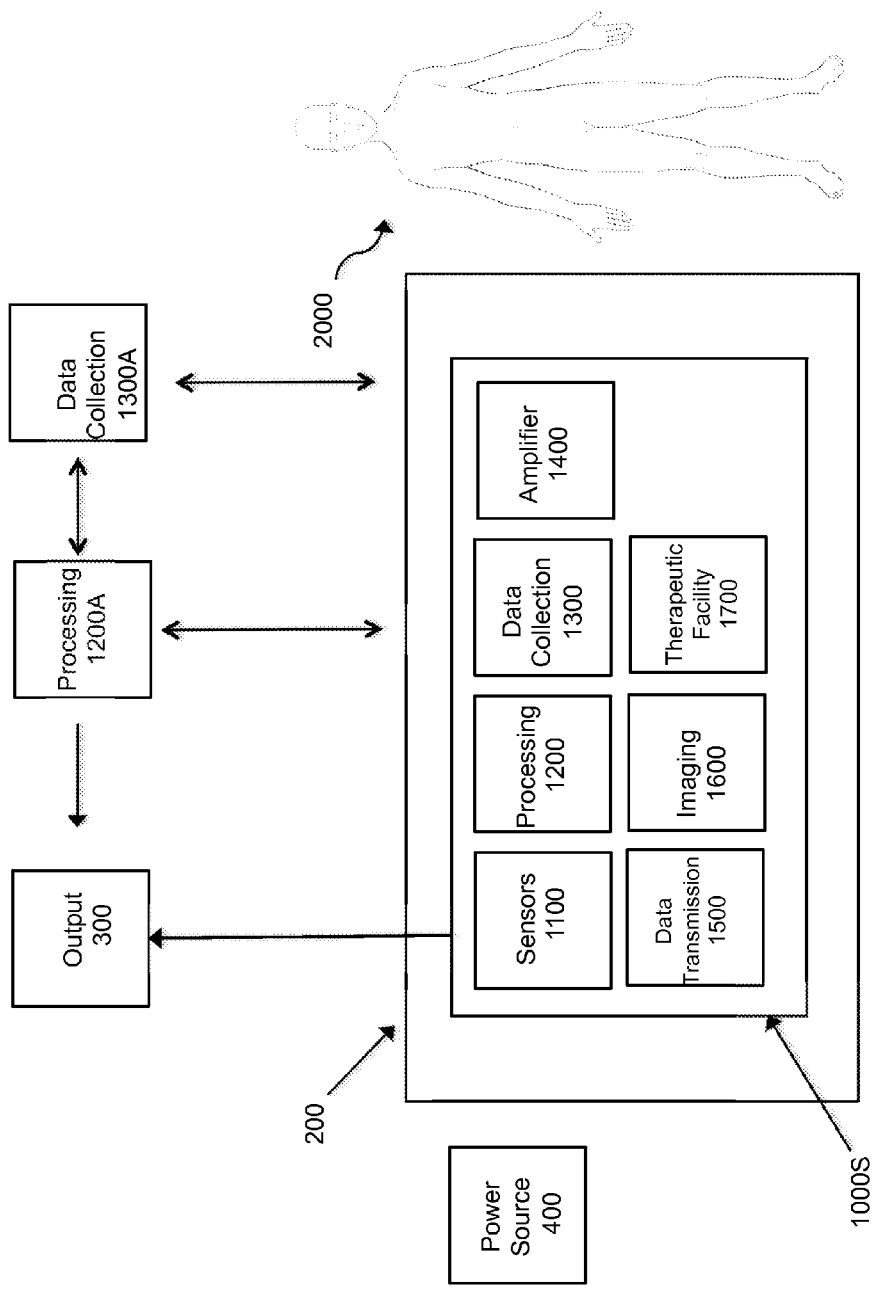
FIG. 1 is a schematic depiction of embodiments of the invention.

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting but merely as a basis for the claims and as a representative basis for teaching one skilled in the art to variously employ the present invention in virtually any appropriately detailed structure. Further, the terms and phrases used herein are not intended to be limiting but rather to provide an understandable description of the invention.

The terms "a" or "an," as used herein, are defined as one or more than one. The term "another," as used herein, is defined as at least a second or more. The terms "including" and/or "having" as used herein, are defined as comprising (i.e., open transition). The term "coupled" or "operatively coupled," as used herein, is defined as connected, although not necessarily directly and not necessarily mechanically or physically. "Electronic communication" is the state of being able to convey or otherwise transmit data either through a physical connection, wireless connection, or combinations thereof.

As described herein, the present invention comprises devices, systems, and methods utilizing flexible and/or stretchable electronic circuits on flexible, expandable, or inflatable surfaces. With reference to the present invention, the term "stretchable", and roots and derivations thereof, when used to modify circuitry or components thereof describes circuitry and/or components thereof having soft or elastic properties capable of being made longer or wider without tearing or breaking, and it is also meant to encompass circuitry having components (whether or not the components themselves are individually stretchable as stated above) that are configured in such a way so as to accommodate a stretchable, inflatable, or expandable surface and remain functional when applied to a stretchable, inflatable, or otherwise expandable surface that is stretched, inflated, or otherwise expanded respectively. The term "expandable", and roots and derivations thereof, when used to modify circuitry or components thereof is also meant to have the meaning ascribed above. Thus, "stretch" and "expand", and all derivations thereof, may be used interchangeably when referring to the present invention. The term "flexible", and roots and derivations thereof, when used to modify circuitry or components thereof describes circuitry and/or components thereof capable of bending without breaking, and it is also meant to encompass circuitry having components (whether or not the components themselves are individually flexible as stated above) that are configured in such a way so as to accommodate a flexible surface and remain functional when applied to a flexible surface that is flexed or otherwise bent. In embodiments, at the low end of 'stretchable', this may translate into material stains greater than 0.5% without fracturing, and at the high end to structures that may stretch 100,000% without a degradation of electrical performance. "Bendable" and roots and derivations thereof, when used to modify circuitry or components thereof describes circuitry and/or components thereof able to be shaped (at least in part) into a curve or angle, and may sometimes be used synonymously herein with "flexible".

FIG. 1 is a schematic depiction of embodiments of the invention. Further description of each of the components of FIG. 1 will be included throughout the specification. Circuitry 1000S is applied, secured, or otherwise affixed to substrate 200. In embodiments, substrate 200 is stretchable and or expandable as described herein. As such the substrate 200 can be made of a plastic material or can be made of an elastomeric material, or combinations thereof. Note that the term "plastic" may refer to any synthetic or naturally occurring material or combination of materials that can be molded or shaped, generally when heated, and hardened into a desired shape. The term "elastomer" may refer a naturally occurring material or a synthetic material, and also to a polymeric material which can be stretched or deformed and return to its original shape without substantial permanent deformation. Such elastomers may withstand substantial elastic deformations. Examples of elastomers used in substrate material include polymeric organosilicon compounds (commonly referred to as "silicones") including Polydimethylsiloxane (PDMS).

Other materials suitable for the substrate include polyimide; photopatternable silicone; SU8 polymer; PDS polydustrene; parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil Al®, PTG Bionate®, PTG Carbosil); silicones/siloxanes (RTV 615®, Sylgard 184®); polytetrafluoroethylene (PTFE, Teflon®); polyamic acid; polymethyl acrylate; stainless steel; titanium and its alloys; platinum and its alloys; and gold. In embodiments, the substrate is made of a stretchable or flexible biocompatible material having properties which may allow for certain devices to be left in the body 2000 for a period of time without having to be retrieved.

Some of the materials mentioned above, specifically parylene and its derivatives and copolymers (parylene-N); ultrahigh molecular weight polyethylene; poly ether ether ketones (PEEK); polyurethanes (PTG Elasthane®, Dow Pellethane®); polylactic acid; polyglycolic acid; polymer composites (PTG Purisil Al®, PTG Bionate®, PTG Carbosil); silicones/siloxanes (RTV 615®, Sylgard 184®); polytetrafluoroethylene (PTFE, Teflon®); polyamic acid; polymethyl acrylate; stainless steel; titanium and its alloys; platinum and its alloys; and gold, are biocompatible. Coatings for the substrate to increase its biocompatibility may include, PTFE, polylactic acid, polyglycolic acid, and poly (lactic-co-glycolic acid).

The materials disclosed for substrate 200 herein may be understood to apply to any of the embodiments disclosed herein that require substrate. It should also be noted that materials can be chosen based on their properties which include degree of stiffness, degree of flexibility, degree of elasticity, or such properties related to the material's elastic moduli including Young's modulus, tensile modulus, bulk modulus, shear modulus, etc., and or their biodegradability.

The substrate 200 can be one of any possible number of shapes or configurations. In embodiments, the substrate 200 is substantially flat and in some embodiments configured to be a sheet or strip. Yet it should be noted that such flat configurations of substrate 200 can be any number of geometric shapes. Other embodiments of flat substrates will be described below including substrates having a tape-like or sheet configuration. Flexible and/or stretchable substrate 200 having a sheet or otherwise substantially flat configuration may be configured such that substrate 200 can be folded, furled, bunched, wrapped or otherwise contained. In embodiments, a substrate 200 configured as such can be folded, furled, bunched, collapsed (such as in an umbrella-like configuration), wrapped, or otherwise contained during delivery through narrow passageways in the subject's body 2000 and then deployed into an unfolded, unfurled, etc. state once in position for deployment. As a non-limiting example, a furled substrate 200 carrying circuitry 100S comprising sensing device 1100 could be delivered via a catheter, then unfurled at such point when it is desired for the sensing device to contact the tissue of interest, such as the surface of the heart, or the inner surface of a lumen such as the pulmonary vein. In embodiments, substrates 200 may also be formed into concave and convex shapes, such as lenses. Such convex and concave substrates can be made of material suitable for contact with the eye, such as a contact lens or implantation into the eye, such a retinal or corneal implant.

Substrate 200 may also be three-dimensional. The three-dimensional substrate 200 can be any number of shapes. Such three-dimensional substrates may be a solid or substantially solid. In embodiments, the three-dimensional substrate may be pliable, flexible and stretchable while still comprising homogeneous or substantially homogenous material throughout its form, such as a foam or a flexible/stretchable polymeric sphere, ovoid, cylinder, disc, or other three-dimensional object. In embodiments, the three-dimensional substrate 200 may be made from several materials. In the presently preferred embodiment for the three-dimensional substrate 200, the substrate is an inflatable body (also referred to herein as an elastomeric vessel). Inflatable bodies of this type may be stretchable, such as a balloon or the like; however, in other embodiments, the inflatable body inflates without stretching. In embodiments, inflation can be achieved via a gas or liquid. In certain embodiments, inflation with a viscous fluid is preferable, but it should be clear that a variety of gases, fluids or gels may be employed for such inflation. Embodiments comprising balloon-like and disc-like inflatable substrates will be discussed in further detail below. The systems to achieve inflation discussed in connection with those embodiments apply to all inflatable embodiments of substrate herein.

In embodiments where the substrate 200 is stretchable, circuitry 1000S is configured in the applicable manners described herein to be stretchable and/or to accommodate such stretching of the substrate 200. Similarly, in embodiments where the substrate 200 is flexible, but not necessarily stretchable, circuitry 1000S is configured in the applicable manners described herein to be flexible and/or accommodate such flexing of the substrate 200. Circuitry 1000S can be applied and/or configured using applicable techniques described below, including those described in connection with exemplary embodiments.

As mentioned above, the present invention may employ one or more of a plurality of flexible and/or stretchable electronics technologies in the implementation thereof. Traditionally, electronics have been fabricated on rigid structures, such as on integrated circuits, hybrid integrated circuits, flexible printed circuit boards, and on printed circuit boards. Integrated circuits, also referred to as ICs, microcircuits, microchips, silicon chips, or simple chips, have been traditionally fabricated on a thin substrate of semiconductor material, and have been constrained to rigid substrates mainly due to the high temperatures required in the step of inorganic semiconductor deposition. Hybrid integrated circuits and printed circuit boards have been the main method for integrating multiple ICs together, such as through mounting the ICs onto a ceramic, epoxy resin, or other rigid non-conducting surface. These interconnecting surfaces have traditionally been rigid in order to ensure that the electrical interconnection methods, such as solder joints to the board and metal traces across the boards, do not break or fracture when flexed. In addition, the ICs themselves may fracture if flexed. Thus, the field of electronics has been largely constrained to rigid electronics structures, which then tend to constrain electronics applications that may require flexibility and or stretchability necessary for the embodiments disclosed herein. For example, high-quality sensing can be achieved by enabling the electronic devices, such as sensor device, into intimate or direct contact with tissues of interest. The rigidity of devices described above has prevented such direct contact. Embodiments described below achieve such direct contact (in some cases described as "conformal contact").

Advancements in flexible and bendable electronics technologies have emerged that enable flexible electronics applications, such as with organic and inorganic semiconductors on flexible plastic substrates, and other technologies described herein. Further, stretchable electronics technologies have emerged that enable applications that require the electronics to be stretchable, such as through the use of mounting ICs on flexible substrates and interconnected through some method of stretchable electrical interconnect, and other technologies as described herein. The present invention may utilize one or more of these flexible, bendable, stretchable, and like technologies, in applications that require the electronics to operate in configurations that may not be, or remain, rigid and planar, such as applications that require electronics to flex, bend, expand, stretch and the like.

In embodiments, the circuitry of the invention may be made in part or in full by utilizing the techniques and processes described below. Note that the below description of the various ways to achieve stretchable and/or flexible electronics is not meant to be limiting, and encompasses suitable variants and or modifications within the ambit of one skilled in the art. As such, this application will refer to the following United States patents and patent applications, each of which is incorporated by reference herein in its entirety: U.S. Pat. No. 7,557,367 entitled "Stretchable Semiconductor Elements and Stretchable Electrical Circuits", issued Jul. 7, 2009 (the "'367 patent"); U.S. Pat. No. 7,521,292 entitled "Stretchable Form of Single Crystal Silicon for High Performance Electronics on Rubber Substrates", issued Apr. 29, 2009 (the "'292 patent"); United States Published Patent Application No. 20080157235 entitled "Controlled Buckling Structures in Semiconductor Interconnects and Nan membranes for Stretchable Electronics", filed Sep. 6, 2007 (the "'235 application"); U.S. patent application having Ser. No. 12/398,811 entitled "Stretchable and Foldable Electronics", filed Mar. 5, 2009 (the "'811 application"); United States Published Patent Application No. 20040192082 entitled "Stretchable and Elastic Interconnects" filed Mar. 28, 2003 (the "'082 application"); United States Published Patent Application No. 20070134849 entitled "Method For Embedding Dies", filed Nov. 21, 2006 (the "'849 application"); United States Published Patent Application No. 20080064125 entitled "Extendable Connector and Network, filed Sep. 12, 2007 (the "'125 application"); U.S. Provisional Patent Application having Ser. No. 61/240,262 (the '262 application") "Stretchable Electronics", filed Sep. 7, 2009; U.S. patent application having Ser. No. 12/616,922 entitled "Extremely Stretchable Electronics", filed Nov. 12, 2009 (the "'922 application"); U.S. Provisional Patent Application having Ser. No. 61/120,904 entitled "Transfer Printing", filed Dec. 9, 2008 (the "'904 application"); United States Published Patent Application No. 20060286488 entitled "Methods and Devices for Fabricating Three-Dimensional Nanoscale Structures", filed Dec. 1, 2004; U.S. Pat. No. 7,195,733 entitled "Composite Patterning Devices for Soft Lithography" issued Mar. 27, 2007; United States Published Patent Application No. 20090199960 entitled "Pattern Transfer Printing by Kinetic Control of Adhesion to an Elastomeric Stamp" filed Jun. 9, 2006; United States Published Patent Application. No. 20070032089 entitled "Printable Semiconductor Structures and Related Methods of Making and Assembling" filed Jun. 1, 2006; United States Published Patent Application No. 20080108171 entitled "Release Strategies for Making Transferable Semiconductor Structures, Devices and Device Components" filed Sep. 20, 2007; and United States Published Patent Application No. 20080055581 entitled "Devices and Methods for Pattern Generation by Ink Lithography", filed Feb. 16, 2007.

"Electronic device" is used broadly herein to encompass an integrated circuit(s) having a wide range of functionality. In embodiments, the electronic devices may be devices laid out in a device island arrangement, as described herein including in connection to exemplary embodiments. The devices can be, or their functionality can include, integrated circuits, processors, controllers, microprocessors, diodes, capacitors, power storage elements, antennae, ASICs, sensors, amplifiers, A/D and D/A converters, associated differential amplifiers, buffers, microprocessors, optical collectors, transducer including electro-mechanical transducers, piezo-electric actuators, light emitting electronics which include LEDs, logic, memory, clock, and transistors including active matrix switching transistors, and combinations thereof. The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means. Components within electronic devices or devices are described herein, and include those components described above. A component can be one or more of any of the electronic devices described above and/or may include a photodiode, LED, TUFT, electrode, semiconductor, other light-collecting/detecting components, transistor, contact pad capable of contacting a device component, thin-film devices, circuit elements, control elements, microprocessors, interconnects, contact pads, capacitors, resistors, inductors, memory element, power storage element, antenna, logic element, buffer and/or other passive or active components. A device component may be connected to one or more contact pads as known in the art, such as metal evaporation, wire bonding, application of solids or conductive pastes, and the like.

Components incapable of controlling current by means of another electrical signal are called passive devices. Resistors, capacitors, inductors, transformers, and diodes are all considered passive devices For purposes of the invention, an active device is any type of circuit component with the ability to electrically control electron flow. Active devices include, but are not limited to, vacuum tubes, transistors, amplifiers, logic gates, integrated circuits, silicon-controlled rectifiers (SCRs), and triode for alternating current (TRIACs).

"Ultrathin" refers to devices of thin geometries that exhibit flexibility.

"Functional layer" refers to a device layer that imparts some functionality to the device. For example, the functional layer may be a thin film, such as a semiconductor layer. Alternatively, the functional layer may comprise multiple layers, such as multiple semiconductor layers separated by support layers. The functional layer may comprise a plurality of patterned elements, such as interconnects running between device-receiving pads.

Semiconductor materials which may be used to make circuits may include amorphous silicon, polycrystalline silicon, single crystal silicon, conductive oxides, carbon annotates and organic materials.

In some embodiments of the invention, semiconductors are printed onto flexible plastic substrates, creating bendable macro-electronic, micro-electronic, and/or nano-electronic devices. Such bendable thin film electronics devices on plastic may exhibit field effect performance similar to or exceeding that of thin film electronics devices fabricated by conventional high temperature processing methods. In addition, these flexible semiconductor on plastic structures may provide bendable electronic devices compatible with efficient high throughput processing on large areas of flexible substrates at lower temperatures, such as room temperature processing on plastic substrates. This technology may provide dry transfer contact printing techniques that are capable of assembling bendable thin film electronics devices by depositing a range of high quality semiconductors, including single crystal Si ribbons, GaAs, INP wires, and carbon nano-tubes onto plastic substrates. This high performance printed circuitry on flexible substrates enables an electronics structure that has wide ranging applications. The '367 patent and associated disclosure illustrates an example set of steps for fabricating a bendable thin film electronics device in this manner. (See FIG. 26A of the '367 patent for Example).

In addition to being able to fabricate semiconductor structures on plastic, it has been demonstrated that metal-semiconductor electronics devices may be formed with printable wire arrays, such as GaAs micro-wires, on the plastic substrate. Similarly, other high quality semiconductor materials have been shown to transfer onto plastic substrates, including Si nano-wires, micro-ribbons, platelets, and the like. In addition, transfer printing techniques using elastomeric stamps may be employed. The '367 patent provides an example illustration of the major steps for fabricating, on flexible plastic substrates, electronics devices that use arrays of single wires (in this instance GaAs wires) with epitaxial channel layers, and integrated holmic contacts. (See FIG. 41 of the '367 patent). In an example, a semi-insulating GaAs wafer may provide the source material for generating the micro-wires. Each wire may have multiple ohmic stripes separated by a gap that defines the channel length of the resultant electronic device. Contacting a flat, elastomeric stamp of PDMS to the wires forms a van der Waals bond. This interaction enables removal of all the wires from the wafer to the surface of the PDMS when the stamp is peeled back. The PDMS stamp with the wires is then placed against an uncured plastic sheet. After curing, peeling off the PDMS stamp leaves the wires with exposed ohmic stripes embedded on the surface of the plastic substrate. Further processing on the plastic substrate may define electrodes that connect the ohmic stripes to form the source, drain, and gate electrodes of the electronics devices. The resultant arrays are mechanically flexible due to the bendability of the plastic substrate and the wires.

In embodiments, and in general, stretchable electronics may incorporate electrodes, such as connected to a multiplexing chip and data acquisition system. For example, such an electrode system may be integrated into a medical application, such as in a catheter for neurological or cardiac monitoring and stimulation. In an example, an electrode may be fabricated, designed, transferred, and encapsulated. In an embodiment, the fabrication may utilize and/or include an SI wafer; spin coating an adhesion layer (e.g. an HMDS adhesion layer); spin coating (e.g. PMMA) patterned by shadow mask, such as in oxygen RIE; spin coating Polyimide; depositing PECVD SiO2; spin 1813 Resist, photolithography patterning; metal evaporation (e.g. Ti, Pt, Au, and the like, or combination of the aforementioned); gold etchant, liftoff in hot acetone; spin Polyimide; PECVD SiO2; spin 1813 Resist, photolithography patterning; RIE etch, and the like. In this embodiment, the fabrication step may be complete with the electrodes on the Si wafer. In embodiments, the Si wafer may then be bathed in a hot acetone bath, such as at 100 C for approximately one hour to release adhesion layer while PI posts keep electrode adhered to the surface of the Si wafer. In embodiments, electrodes may be designed in a plurality of shapes and distributed in a plurality of distribution patterns. Electrodes may be interconnected to electronics, multiplexing electronics, interface electronics, a communications facility, interface connections, and the like including any of the facilities/elements described on connection with FIG. 1 and/or the exemplary embodiments herein. In embodiments, the electrodes may be transferred from the Si wafer to a transfer stamp, such as a PDMS stamp, where the material of the transfer stamp may be fully cured, partially cured, and the like. For example, a partially cured PDMS sheet may be ~350 nm, where the PDMS was spun on at 300 rpm for 60 s, cured 65 C for 25 min, and used to lift electrodes off of the PDMS sheet. In addition, the electrodes may be encapsulated, such as wherein the electrodes are sandwiched between a supporting PDMS layer and second PDMS layer while at least one of the PDMS layers is partially cured.

In embodiments, stretchable electronics configurations may incorporate flex PCB design elements, such as flex print, chip flip configurations (such as bonded onto the PCB), and the like, for connections to electrodes and/or devices, and for connections to interface electronics, such as to a data acquisition system (DAQ). For example, a flex PCB may be joined to electrodes by an anisotropic conductive film (ACF) connection, solder joints may connect flex PCB to the data acquisition system via conductive wires, and the like. In embodiments, the electrodes may be connected onto a surface by employing a partially-cured elastomer (e.g. PDMS) as an adhesive.

In embodiments, stretchable electronics may be formed into sheets of stretchable electronics, such as to monitor neural signal activity via stretchable electrode systems as described below. In embodiments, stretchable sheets may be thin, such as approximately 100 μm. Optionally, amplification and multiplexing may be implemented without substantially heating the contact area, such as with micro-fluidic cooling.

In embodiments, a sheet having arrays of electronic devices comprising electrodes may be cut into different shapes and remain functional, such as through communicating electrode islands which determine the shape of the electrode sheet. Electrodes are laid out in a device island arrangement (as described herein) and may contain active circuitry designed to communicate with each other via inter-island stretchable interconnects so that processing facility (described herein) in the circuitry can determine in real-time the identity and location of other such islands. In this way, if one island becomes defective, the islands can still send out coordinated, multiplexed data from the remaining array. Such functionality allows for such arrays to be cut and shaped based on the size constraints of the application. A sheet, and thus circuitry, may be cut to side and the circuitry will poll remaining electrodes and/or devices to determine which are left and will modify the calibration accordingly. An example of a stretchable electronics sheet containing this functionality, may include electrode geometry, such as a 20×20 array of platinum electrodes on 1 mm pitch for a total area of 20×20 mm$^2$; an electrode impedance, such as 5 kohm at 1 khz (adjustable); a configuration in a flexible sheet, such as with a 50 μm total thickness, and polyimide encapsulated; a sampling rate, such as 2 kHz per channel; a voltage dynamic range, such as +/−6 mV; a dc voltage offset range, such as −2.5 to 5 V, with dc rejection; a voltage noise, such as 0.002 mV, a maximum signal-to-noise ratio, such as 3000; a leakage current, such as 0.3 to typical, 10 μA to maximum, as meets IEC standards, and the like; an operating voltage of 5 V; an operating power per channel, such as less than 2 mW (adjustable); a number of interface wires, such as for power, ground, low impedance ground, data lines, and the like; a voltage gain, such as 150; a mechanical bend radius, such as 1 mm; a local heating capability, such as heating local tissue by up to 1° C.; biocompatibility duration, such as 2 weeks; active electronics, such as a differential amplifier, a multiplexer (e.g. 1000 transistors per channel); a data acquisition system, such as with a 16 bit A/D converter with a 500 kHz sampling rate, less than 2 μV noise, data login and real-time screen display; safety compliance, such as to IEC10601; and the like.

In embodiments of the invention, mechanical flexibility may represent an important characteristic of devices, such as on plastic substrates, for many applications. Micro/nanowires with integrated ohmic contacts provide a unique type of material for high performance devices that can be built directly on a wide range of device substrates. Alternatively, other materials may be used to connect electrical components together, such as connecting electrically and/or mechanically by thin polymer bridges with or without metal interconnects lines.

In embodiments, an encapsulation layer may be utilized. An encapsulating layer may refer to coating of the device, or a portion of the device. In embodiments, the encapsulation layer may have a modulus that is inhomogeneous and/or that spatially varies. Encapsulation layers may provide mechanical protection, device isolation, and the like. These layers may have a significant benefit to stretchable electronics. For example, low modulus PDMS structures may increase the range of stretchability significantly (described at length in the '811 application). The encapsulation layer may also be used as a passivation later on top of devices for the protection or electrical isolation. In embodiments, the use of low modulus strain isolation layers may allow integration of high performance electronics. The devices may have an encapsulation layer to provide mechanical protection and protection against the environment. The use of encapsulation layers may have a significant impact at high strain. Encapsulants with low moduli may provide the greatest flexibility and therefore the greatest levels of stretchability. As referred to in the '811 application, low modulus formulations of PDMS may increase the range of stretchability at least from 60%. Encapsulation layers may also relieve strains and stresses on the electronic device, such as on a functional layer of the device that is vulnerable to strain induced failure. In embodiments, a layering of materials with different moduli may be used. In embodiments, these layers may be a polymer, an elastomer, and the like. In embodiments, an encapsulation may serve to create a biocompatible interface between an implanted stretchable electronic system, such as Silk encapsulation of electronic devices in contact with tissue.

Returning to flexible and stretchable electronics technologies that may be utilized in the present invention, it has been shown that buckled and wavy ribbons of semiconductor, such as GaAs or Silicon, may be fabricated as part of electronics on elastomeric substrates. Semiconductor ribbons, such as with thicknesses in the submicron range and well-defined, 'wavy' and/or 'buckled' geometries have been demonstrated. The resulting structures, on the surface of, or embedded in, the elastomeric substrate, have been shown to exhibit reversible stretchability and compressibility to strains greater than 10%. By integrating ohmic contacts on these structured GaAs ribbons, high-performance stretchable electronic devices may be achieved. The '292 patent illustrates steps for fabricating stretchable GaAs ribbons on an elastomeric substrate made of PDMS, where the ribbons are generated from a high-quality bulk wafer of GaAs with multiple epitaxial layers (See FIG. 22). The wafer with released GaAs ribbons is contacted to the surface of a pre-stretched PDMS, with the ribbons aligned along the direction of stretching. Peeling the PDMS from the mother wafer transfers all the ribbons to the surface of the PDMS. Relaxing the prestrain in the PDMS leads to the formation of large scale buckles/wavy structures along the ribbons. The geometry of the ribbons may depend on the prestrain applied to the stamp, the interaction between the PDMS and ribbons, and the flexural rigidity of the ribbons, and the like. In embodiments, buckles and waves may be included in a single ribbon along its length, due for example, to thickness variations associated with device structures. In practical applications, it might be useful to encapsulate the ribbons and devices in a way that maintains their stretchability. The semiconductor ribbons on an elastomeric substrate may be used to fabricate high-performance electronic devices, buckled and wavy ribbons of semiconductor multilayer stacks and devices exhibiting significant compressibility/stretchability. In embodiments, the present invention may utilize a fabrication process for producing an array of devices utilizing semiconductor ribbons, such as an array of CMOS inverters with stretchable, wavy interconnects. Also, a strategy of top layer encapsulation may be used to isolate circuitry from strain, thereby avoiding cracking.

In embodiments, a neutral mechanical plane (NMP) in a multilayer stack may define the position where the strains are zero. For instance, the different layers may include a support layer, a functional layer, a neutral mechanical surface adjusting layer, an encapsulation layer with a resultant neutral mechanical surface such as coincident with the functional layer, and the like. In embodiments, the functional layer may include flexible or elastic device regions and rigid island regions. In embodiments, an NMP may be realized in any application of the stretchable electronics as utilized in the present invention.

In embodiments, semiconductor ribbons (also, micro-ribbons, nano-ribbons, and the like) may be used to implement integrated circuitry, electrical interconnectivity between electrical/electronic components, and even for mechanical support as a part of an electrical/electronic system. As such, semiconductor ribbons may be utilized in a great variety of ways in the configuration/fabrication of flexible and stretchable electronics, such as being used for the electronics or interconnection portion of an assembly leading to a flexible and/or stretchable electronics, as an interconnected array of ribbons forming a flexible and/or stretchable electronics on a flexible substrate, and the like. For example, nano-ribbons may be used to form a flexible array of electronics on a plastic substrate. The array may represent an array of electrode-electronics cells, where the nano-ribbons are pre-fabricated, and then laid down and interconnected through metallization and encapsulation layers. Note that the final structure of this configuration may be similar to electronic device arrays as fabricated directly on the plastic, as described herein, but with the higher electronics integration density enabled with the semiconductor ribbons. In addition, this configuration may include encapsulation layers and fabrication steps which may isolate the structure from a wet environment. This example is not meant to limit the use of semiconductor ribbons in any way, as they may be used in a great variety of applications associated with flexibility and stretchability. For example, the cells of this array may be instead connected by wires, bent interconnections, be mounted on an elastomeric substrate, and the like, in order to improve the flexibility and/or stretchability of the circuitry.

Wavy semiconductor interconnects is only one form of a broader class of flexible and stretchable interconnects that may (in some cases) be referred to as 'bent' interconnects, where the material may be semiconductor, metal, or other conductive material, formed in ribbons, bands, wire, traces, and the like. A bent configuration may refer to a structure having a curved shape resulting from the application of a force, such as having one or more folded regions. These bent interconnections may be formed in a variety of ways, and in embodiments, where the interconnect material is placed on an elastomeric substrate that has been pre-strained, and the bend form created when the strain is released. In embodiments, the pre-strain may be pre-stretched or pre-compressed, provided in one, two, or three axes, provided homogeneously or heterogeneously, and the like. The wavy patterns may be formed along pre-strained wavy patterns, may form as 'pop-up' bridges, may be used with other electrical components mounted on the elastomer, or transfer printed to another structure. Alternately, instead of generating a 'pop-up' or buckled components via force or strain application to an elastomeric substrate, a stretchable and bendable interconnect may be made by application of a component material to a receiving surface. Bent configurations may be constructed from micro-wires, such as transferred onto a substrate, or by fabricating wavy interconnect patterns either in conjunction with electronics components, such as on an elastomeric substrate.

Figure 2:
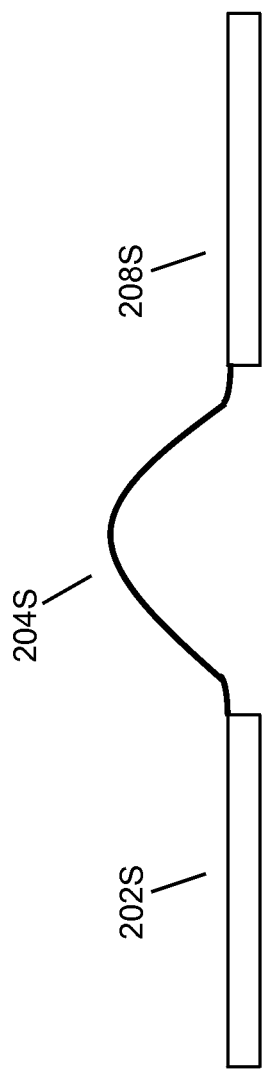
FIG. 2 depicts a buckled interconnection.

Semiconductor nanoribbons, as described herein, may utilize the method of forming wavy 'bent' interconnections through the use of forming the bent interconnection on a pre-strained elastomeric substrate, and this technique may be applied to a plurality of different materials. Another general class of wavy interconnects may utilize controlled buckling of the interconnection material. In this case, a bonding material may be applied in a selected pattern so that there are bonded regions that will remain in physical contact with the substrate (after deformation) and other regions that will not. The pre-strained substrate is removed from the wafer substrate, and upon relaxation of the substrate, the unbounded interconnects buckle (pop-up') in the unbonded (or weakly bonded) regions. Accordingly, buckled interconnects impart stretchability to the structure without breaking electrical contact between components, thereby providing flexibility and/or stretchability. FIG. 2 shows a simplified diagram showing a buckled interconnection 204S between two components 202S and 208S.

In embodiments, any, all, or combinations of each of the interconnection schemes described herein may be applied to make an electronics support structure more flexible or bendable, such as applying bent interconnects to a flexible substrate, such as plastic or elastomeric substrates. However, these bent interconnect structures may provide for a substantially more expandable or stretchable configuration in another general class of stretchable electronic structures, where rigid semiconductor islands are mounted on an elastomeric substrate and interconnected with one of the plurality of bent interconnect technologies. This technology is presented here, and also in the '262 application, which has been incorporated by reference in its entirety. This configuration also uses the neutral mechanical plane designs, as described herein, to reduce the strain on rigid components encapsulated within the system. These component devices may be thinned to the thickness corresponding to the desired application or they may be incorporated exactly as they are obtained. Devices may then be interconnected electronically and encapsulated to protect them from the environment and enhance flexibility and stretchability.

Figure 3:
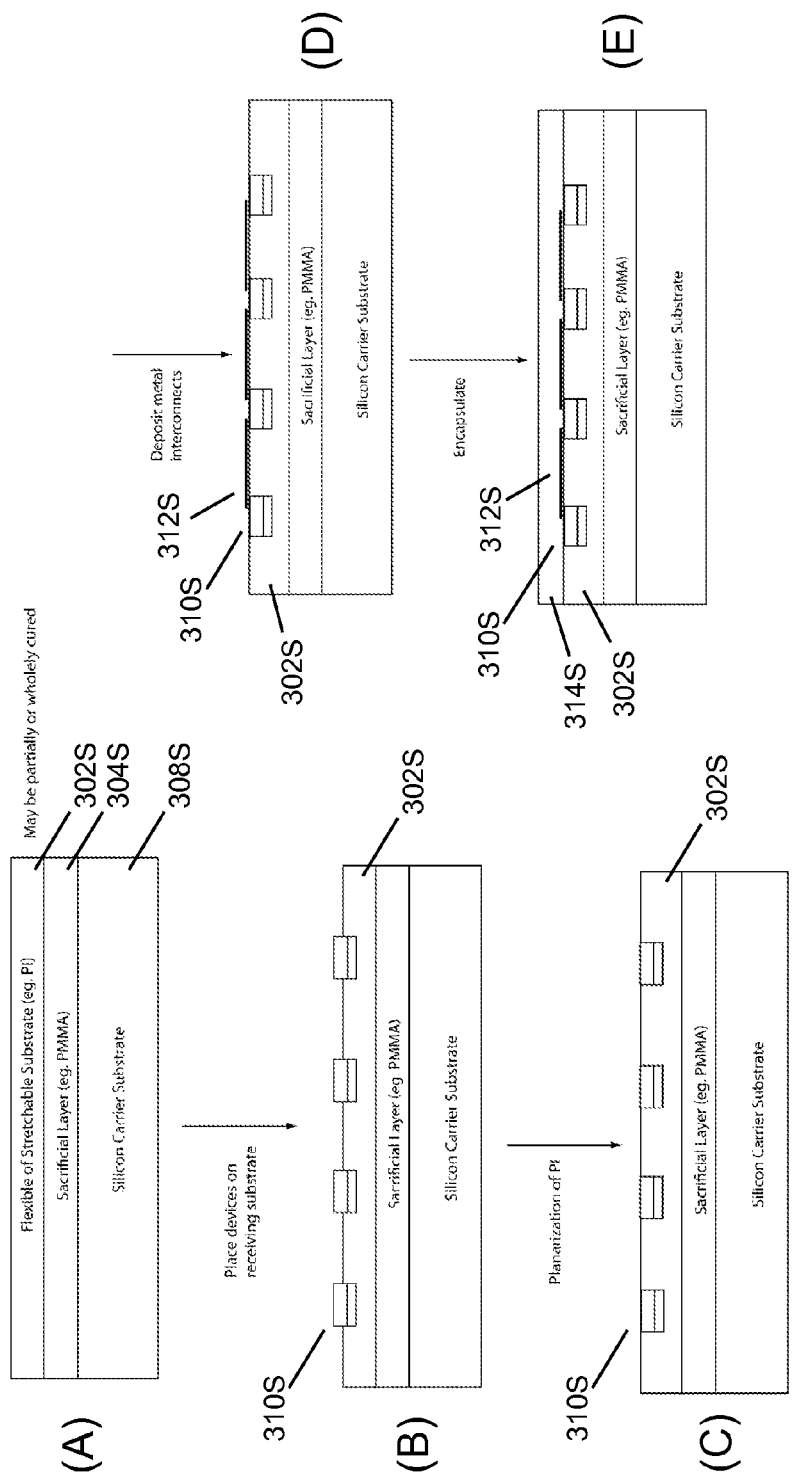
FIG. 3 depicts a stretchable electronics configuration with semiconductor; islands mounted on an elastomeric substrate with stretchable interconnects.

In an embodiment, the first step in a process to create stretchable and flexible electronics as described herein involves obtaining required electronic devices and components and conductive materials for the functional layer. The electronics are then thinned (if necessary) by using a back grinding process. Many processes are available that can reliably take wafers down to 50 microns. Dicing chips via plasma etching before the grinding process allows further reduction in thickness and can deliver chips down to 20 microns in thickness. For thinning, typically a specialized tape is placed over the processed part of the chip. The bottom of the chip is then thinned using both mechanical and/or chemical means. After thinning, the chips may be transferred to a receiving substrate, wherein the receiving substrate may be a flat surface on which stretchable interconnects can be fabricated. FIG. 3 illustrates an example process, which begins by creating a flexible substrate 302S on the carrier 308S coated with a sacrificial layer 304S (FIG. 3A), placing devices 310S on the flexible substrate (FIG. 3B), and performing a planarization step in order to make the top surface of the receiving substrate the same height as that of the die surface (FIG. 3C). The interconnect fabrication process follows. The devices 310S deposited on the receiving substrate are interconnected 312S which join bond pads from one device to another (FIG. 3D). In embodiments, these interconnects 312S may vary from 10 microns to 10 centimeters. A polymeric encapsulating layer 314S may then be used to coat the entire array of interconnected electronic devices and components (FIG. 2E). The interconnected electronic devices are then released from the substrate by etching away sacrificial materials with a solvent. The devices are then ready to undergo stretch processing. They are transferred from the rigid carrier substrate to an elastomeric substrate such as PDMS. Just before the transfer to the new substrate, the arrays are pre-treated such that the device/component islands preferentially adhere to the surface leaving the encapsulated interconnects free to be displaced perpendicular to the receiving substrate.

In embodiments, the interconnect system is a straight metal line connecting two or more bond pads. In this case the electronic array is transferred to a pre-strained elastomeric substrate. Upon relaxation of this substrate the interconnects will be displaced perpendicular to the substrate, thus producing outward buckling. This buckling enables stretching of the system.

In another embodiment, the interconnects are a serpentine pattern of conductive metal. These types of interconnected arrays need not be deposited on a pre-strained elastomeric substrate. The stretchability of the system is enabled by the winding shape of the interconnects.

Stretchable/flexible circuits may be formed on paper, plastic, elastomeric, or other materials with the aid of techniques including but not limited to conventional photolithographic techniques, sputtering, chemical vapor deposition, ink jet printing, or organic material deposition combined with patterning techniques. Semiconductor materials which may be used to make circuits may include amorphous silicon, polycrystalline silicon, single-crystal silicon, conductive oxides, carbon nanotubes and organic materials. In embodiments, the interconnects may be formed of electrically conducting film, stripe, pattern, and the like, such as on an elastomer or plastic material, where the film may be made to buckle, deform, stretch, and the like, as described herein. In embodiments, the interconnect may be made of a plurality of films, such as on or embedded in the flexible and/or a stretchable substrate or plastic.

Figure 4:
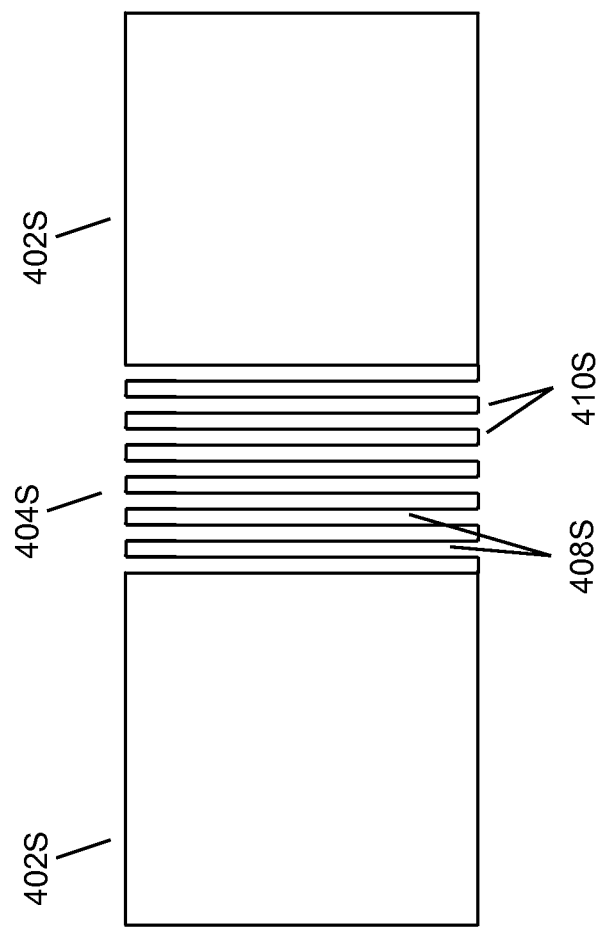
FIG. 4 depicts an extremely stretchable interconnect.

In embodiments, the interconnection of device islands 402S may utilize an extremely stretchable interconnect 404S, such as shown in FIG. 4, and such as the various configurations disclosed in the '922 application. The geometry and the dimension of the interconnects 404S is what makes them extremely compliant. Each interconnect 404S is patterned and etched so that its structural form has width and thickness dimensions that may be of comparable size (such as their ratio or inverse ratio not exceeding about a factor of 10); and may be preferably equal in size. In embodiments, the interconnect may be formed in a boustrophedonic style such that it effectively comprises long bars 408S and short bars 410S. This unique geometry minimizes the stresses that are produced in the interconnect when subsequently stretched because it has the effective form of a wire, and behaves very differently than interconnect form factors having one dimension greatly exceeding the other two (for example plates). Plate type structures primarily relieve stress only about a single axis via buckling, and withstand only a slight amount of shear stress before cracking. This invention may relieve stress about all three axes, including shears and any other stress. In addition, because the interconnect may be formed out of rigid materials, after being stretched it may have a restorative force which helps prevent its wire-like form from getting tangled or knotted when re-compressing to the unstretched state. Another advantage of the boustrophedonic geometry is that it minimizes the initial separation distance between the islands. In embodiments, the interconnects may be formed either monolithically (i.e., out of the same semiconductor material as the device islands) or may be formed out of another material.

Figure 5:
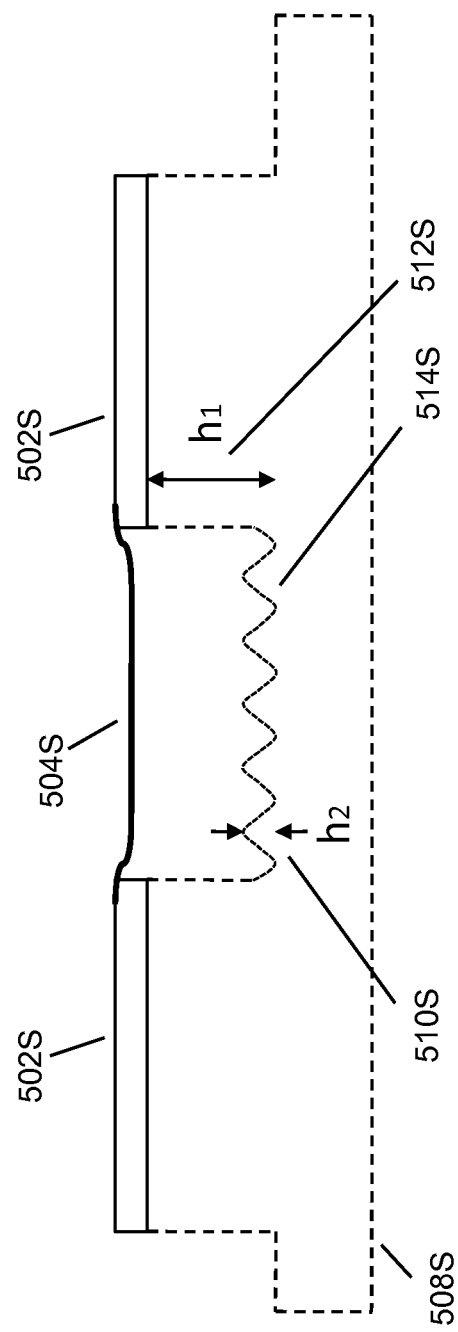
FIG. 5 depicts a raised stretchable interconnect with expandable elastomeric substrate.

In another embodiment the elastomeric substrate may comprise two layers separated by a height 512S, such as shown in FIG. 5. The top "contact" layer contacts the device island 502S, where the device islands 502S are interconnected 504S with one of the interconnection schemes described herein. In addition, the bottom layer may be a "wavy" layer containing ripples 514S or square waves molded into the substrate 508S during elastomer fabrication. These waves enable additional stretching, whose extent may depend on the amplitude 510S and wavelength of the waves pattern-molded in the elastomer.

In embodiments, the device island may be any prefabricated integrated circuit (IC), where the IC may be mounted on, inside, between, and the like, a flexible and/or stretchable substrate. For example, an additional elastomeric layer may be added above the structure as shown in FIG. 5, such as to encapsulate the structure for protection, increased strength, increase flexibility, and the like. Electrical contacts to embedded electrical components may be provided across the embedded layer, through the elastomeric layer(s) from a second electrical interconnection layer, and the like. For example, an IC may be encapsulated in a flexible material where the interconnects are made accessible as described in the '849 application. (See FIG. 1 of the '849 application for example). In this example the embedded IC is fabricated by first placing the IC onto a carrier, such as a rigid carrier, and where the IC may be a thinned IC (either thinned before the mounting on the carrier, or thinned while on the carrier). A second step may involve a coating of the IC with some adhesive, elastomer, or other insulating material that can be flowed onto the IC. A third step may be to gain access to the electrical contacts of the IC, such as by laser drilling or other method known to the art. A fourth step may be to flow electrical conductor into the openings, thus establishing a electrical access to the electrical connections of the IC. Finally, the IC thus encased may be freed from the carrier. Now the structure may be more easily embedded into a flexible substrate while maintaining electrical connectivity. In embodiments, this structure may be a flexible structure, due to the thinness of the IC, the elastic character of the surrounding structure, the elastic configuration of the extended electrical contacts, and the like.

It should be noted that many of the stretchable electronics techniques utilize the process of transfer printing, for example, with a PDMS stamp. In embodiments, the present invention may include a method of dynamically controlling the surface adhesion of a transfer printing stamp, such as described here, and disclosed in the '904 application. Transfer printing stamps have many uses, one of which is to pick up thin films of materials ("targets") from one surface ("initial surface") and deposit them onto another surface ("final surface"). The pickup may be achieved by pressing the transfer printing stamp into contact with the targets, applying some pressure to create Van der Waals bonds between the stamp and the targets, peeling off the stamp with the targets, and then placing the stamp with targets into contact with another surface, applying pressure, and peeling off the stamp without the targets so they remain on the final surface. If the final surface has a higher bonding strength with the targets than the transfer stamp, they will remain on the final surface when the transfer stamp is peeled off. Alternately, the rate of peeling the transfer stamp can be adjusted to vary the target to stamp and target to final surface bonding force ratio. The present invention describes a novel method of depositing the targets, by changing the surface adhesion of the transfer stamp after the targets have been picked up. This may be done while the stamp with targets is in contact with the final surface. In embodiments, the adhesion control can be done by introducing micro-fluidic channels into the transfer stamp, so that water or other fluid can be pumped to the surface of the stamp from within it, thereby changing the surface adhesion from sticky to non-sticky.

In embodiments, the present invention may accomplish transfer printing by using a transfer printing stamp that has been formed with micro-fluidic channels such that a fluid (liquid or gas) can be pumped to the surface of the stamp to wet or chemically functionalize the surface and therefore change the surface adhesion of the stamp surface. The transfer printing stamp may be made out of any material, including but not limited to poly-dimethyl-siloxane (PDMS) and derivatives thereof. In one non-limiting embodiment, the stamp is a piece of PDMS formed into a cuboid, which may have dimensions ranging from about 1 micrometer to 1 meter. For this example, the cuboid is 1 cm×1 cm×0.5 cm (length, width, thickness). One 1 cm×1 cm surface of the cuboid is designated as the stamping face. By using a photolithography mask, or a stencil mask, a pattern of vertical holes (channels) is etched from the stamping face through to the opposing face of the stamp. This may be done with an oxygen reactive ion etch. These holes are the micro-fluidic channels, and may be about 0.1-10 micrometers in diameter. They may be spaced apart by about 1-50 micrometers. Another piece of PDMS may be formed into a reservoir shape (e.g. a 1 cm×1 cm×0.5 cm cuboid with a smaller cuboid (about 0.8 cm×0.8 cm×0.3 cm) cut out from one surface). This shape may be formed by pouring the PDMS into a mold, curing it, and removing it from the mold. This additional piece of PDMS may then be placed into contact with the first piece of PDMS and bonded (this may be done via ultraviolet ozone exposure or oxygen plasma exposure of the PDMS prior to contacting the two pieces) such that the two pieces form the shape shown in FIG. 6, step A. Then, one or more holes may be punctured into the top of the reservoir so that a fluidic pipe can be fitted for pumping water into the stamp. In another non-limiting embodiment, the stamp is constructed as described above, except that the first piece of PDMS is formed to have micro-fluidic channels by means of molding. PDMS molding is a well known art. First, a mold is created that is the inverse of the desired shape. In this case, that is an array of vertical posts on a base with four walls. This mold is then filled with PDMS by pouring in the PDMS, allowing it to cure (which may be at elevated temperature), and then removing the PDMS. In another non-limiting embodiment, the stamping surface is also patterned with an array of shallow-etched surface channels. In embodiments, these channels may be about 100-10000 nm wide, and 100-10000 nm etched-into the PDMS. They may form a linear array or a checkerboard grid. The purpose of the channels is to help distribute a liquid from the vertical micro-fluidic channels around the surface of the stamp. In addition, these channels serve to allow an exit for the air that must be displaced to push the liquid to the surface of the stamp. An example of a liquid that may be used includes, but is not limited to, water (which will wet the surface of the stamp and decrease its adhesivity). In the case of a gas fluid, these surface channels may not be necessary. Examples of gasses that can lower the surface adhesion of PDMS are dimethyldichlorosilane (DDMS), perfluorooctyltrichlorosilane (FOTS), perfluorodecyltris(dimethylamino)silane (PF10TAS), and perfluorodecanoic acid (PFDA), and the like.

Figure 6:
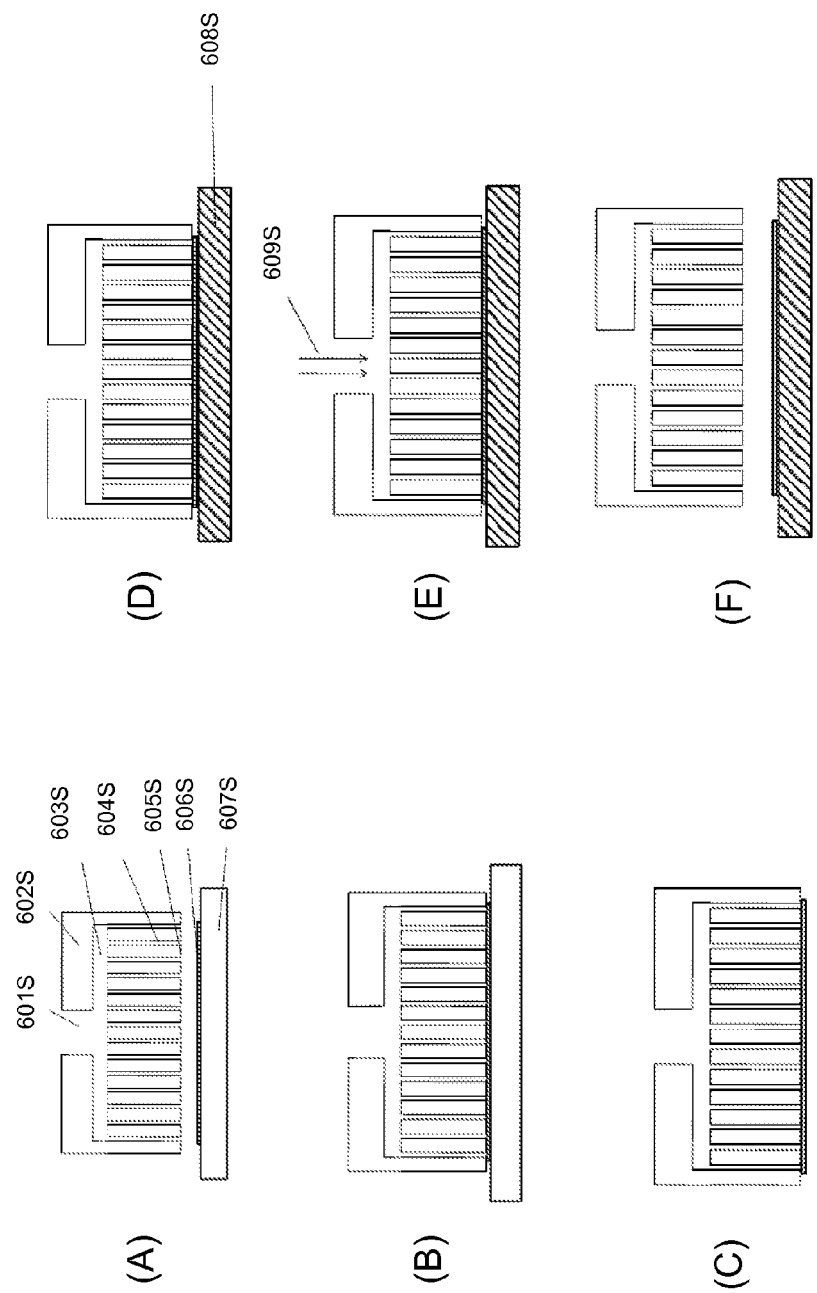
FIG. 6 depicts a method for controlled adhesion on an elastomeric stamp.

In embodiments, the stamp may be operated as shown in FIG. 6. First, it is pressed into contact with a substrate that has the target material or devices to be picked up. (FIG. 6A). The target material is picked up by Van der Waal's forces between itself and the stamp as is well known (FIG. 6B,C). Target material is placed in contact with the final substrate, and pressed into contact (FIG. 6D). The fluid (for example, water) is pumped to the stamp surface, to reduce adhesion (FIG. 6E). The stamp may be left in this state (of contact with water) for as long as necessary for the water to fully wet the stamp surface. Finally, the stamp is removed, leaving the target material behind on the final substrate (FIG. 6F). In FIG. 6A-F, the following labels are made for clarity: fluid inlet 601S; PDMS stamp 602S; fluid distribution reservoir 603S; micro-fluidic channels to stamp surface 604S; adhesive stamp surface 605S; devices to be picked up and transfer printed 6; initial substrate 607S; final substrate 608S; pump in water 609S so it reaches the end of the micro-fluidic channels to alter the surface adhesion of the transfer stamp and release the devices. Note that any surface channels on the stamp surface are not shown in the Figure, and the Figure is not drawn to scale.

Another example of configurations to enable stretchable circuitry are as described in the '125 application in connection with an extendable interconnect. (See FIG. 3 of the '125 application). The electrical component may be considered as one of a plurality of interconnected nodes, whose interconnections expand/extend as the underlying flexible substrate expands. In embodiments, flexible and stretchable electronics may be implemented in a great variety of ways, including configurations involving the substrate, the electrical components, the electrical interconnects, and the like, and involve electrical, mechanical, and chemical processes in their development and implementation.

As amply discussed herein, CMOS devices offer a variety sophisticated functionality including sensing, imaging, processing, logic, amplifiers, buffers, A/D converters, memory, clock and active matrix switching transistors. The electronic devices or the "device islands" of the stretchable/flexible circuitry of the present invention may be devices and are themselves capable of performing the functionality described herein, or portions thereof.

In embodiments, devices and device islands, devices are to be understood as "active" as described above.

In embodiments, the electronic devices are optionally laid out in a device island arrangement, as described herein. The functionality described herein with respect to circuitry 1000S and thus electronic devices may thus be present in an electronic device itself, spread across arrays of electronic devices and/or device components, or achieved via electronic communication and cooperation with other electronic devices and/or device components each electronic device (or electronic device and device component combination) having separate or additive, but complementary functions that will become apparent from this disclosure. In embodiments, such electronic communication could be wireless. Therefore, said devices may comprise a transducer, transmitter, or receiver capable of such wireless transmission.

Returning to FIG. 1, this figure schematically depicts the functionality of the circuitry 1000S (and thus the electronic devices, device components, or combinations thereof). Elements 1100-1700 and their sub elements and components including electronic devices, device components, or combinations thereof may be present in the circuitry 1000S individually or in any combination as applicable. Certain combinations will be discussed below; however, the below discussions merely depict exemplary embodiments of the present invention and thus they are therefore not to be considered limiting of its scope. It will be readily appreciated that the elements of circuitry 1000S, as generally described herein, could be arranged and designed in a wide variety of different configurations. Nonetheless, the invention will be described and explained with additional specificity and detail.

Circuitry 1000S comprises sensors (alternatively termed "sensor devices") 1100 to detect various parameters of the subject's body including, thermal parameters such as temperature, and infrared; optical parameters; electrochemical and biochemical parameters such as, pH, enzymatic activity, blood components including blood gas and blood glucose, ion concentrations, protein concentrations; electrical parameters such as resistance, conductivity, impedance, EKG, EEG, and EMG; sound, and pressure, tactile, surface characteristics, or other topographic features of the body. Thus, to achieve the detection of the above-mentioned parameters, sensors may include thermistors, thermocouples, silicon band gap temperature sensors, thin-film resistance temperature devices, LED emitters, optical sensors including photodetectors, electrodes, piezoelectric sensors, ultrasonic including ultrasound emitters and receivers; ion sensitive field effect transistors, and microneedles. Exemplary embodiments using one or more of the above sensors, or detecting and/or measuring one or more of the above parameters will be discussed below.

The separation distance between sensors (e.g., sensor device islands) can be any that is manufacturable, a useful range may be, but is not limited to, 10 μm-10000 μm. In embodiments, sensors 1100 can be characterized as sensor circuits. Individual sensors may be coupled to a differential amplifier, and/or a buffer and/or an analog to digital converter. The resulting sensor circuits may be formed on the same, or different, devices than the sensors themselves. The circuits may be laid out in an active matrix fashion such that the readings from multiple sensors 1100 can be switched into and processed by one or a few amplifier/logic circuits. Signals from the array of sensors 1100 can be processed using multiplexing techniques, including those described in published international patent application WO2009/114689 filed Mar. 12, 2009 the entirety of which is hereby incorporated herein by reference. Multiplexor component circuitry may be located on or within the circuitry 1000S on the substrate 200, or at a location that avoids interference with the operation of the device such as for example at the base of a catheter guide wire (which is relevant in embodiments where the substrate is a catheter balloon; although other areas that avoid interference with operation will be apparent.)

Circuitry 1000S comprises processing facility 1200 (alternatively referred to herein as "processor", "processing", and the terms mentioned immediately below) which may include a signal processor, digital processor, embedded processor, microcontroller, microprocessor, ASIC, or the like that may directly or indirectly facilitate execution of program code or program instructions stored thereon or accessible thereto. In addition, the processing facility 1200 may enable execution of multiple programs, threads, and codes. The threads may be executed simultaneously to enhance the performance of the processing facility 1200 and to facilitate simultaneous operations of the application. By way of implementation, methods, program codes, program instructions and the like described herein may be implemented in one or more thread. The thread may spawn other threads that may have assigned priorities associated with them; the processing facility 1200 may execute these threads based on priority or any other order based on instructions provided in the program code. The processing facility 1200 (and/or the circuitry 1000S in general) may include or be in electronic communication memory that stores methods, codes, instructions and programs as described herein and elsewhere. The processing facility 1200 may access a storage medium through an interface that may store methods, codes, and instructions to perform the methods and functionality described herein and elsewhere. Processing facility 1200 comprised in or is in electronic communication with the other elements of the circuitry 1000S including the electronic devices and/or device components. Off-board processing facility 1200A comprises all the functionality described above; however, is physically separate from circuitry 1000S yet in electronic communication thereto.

Data collection facility 1300 (and off-board data collection facility 1300A) are configured to each independently or both collect and store data generated by the circuitry 1000S and the elements thereof including imaging facility 1600 (discussed below), and therapeutic facility 1700 (discussed below). Data transmission facility 1500 includes a means of transmitting (RF and/or wired) the sensor information to processing facility 1200 or off-board processing facility 1200A. Each of the elements 1100-1700 are also configured to be in electronic communication with one another and need not necessarily communicate through the data transmission facility 1500. In embodiments, circuitry 1000S and/or data transmission facility 1500 is in electronic communication with output facility 300 which, in embodiments, can be in electronic communication with processing facility 1200A or a separate processing facility. The various outputs described herein, such as visual maps based on sensed parameters, should be understood to emanate from the output facility 300.

Circuitry 1000S may be connected or otherwise in electronic communication with external/separate devices and systems by physical connection, including the methods described above and by providing conductive pads on the circuitry 1000S in an accessible location or location that avoids interference with the operation of the device and interfacing anisotropic conductive film (ACF) connectors to the conductive pads. Also, the circuitry 1000S and/or associated devices 10105 may comprise a transducer, transmitter, transceiver, or receiver capable of wireless transmission and thus wireless communication with external/separate devices and systems. In addition, circuitry 1000S islands may be made to perform optical data communication down a waveguide, such as the one described below.

Power source 400 can supply power to circuitry 1000S in any number of ways, including externally optically, with a waveguide and having PV cells made in a stretchable/flexible format in addition to the rest of the circuitry. Alternately, thin film batteries may be used to power the circuitry 1000S, which could enable an apparatus to be left in the body and communicate with the operator. Alternately, RF communication circuits on the apparatus may not only be used to facilitate wirelessly communication between devices within the circuitry and/or to external/separate systems, but they may also receive RF power to power the circuits. Using such approaches, the need for external electrical interfaces may be eliminated.

Circuitry 1000S includes therapeutic facility 1700 in embodiments of the invention, include various elements to effect a desired therapy. In embodiments, circuitry can comprise heat or light activated drug-delivery polymers that when activated could release chemical agents, such as anti-inflammatory drugs, to local sites in the body. Therefore, in embodiments, light emitting electronics (such as LED) could be utilized to activate a drug delivery polymer.

Other therapies can be administered/effected by circuitry 1000S such as circuitry configured to deliver ablative therapy to cardiac tissue during deployment. Other exemplary embodiments of therapeutic facility 1700 will be described herein. Those, exemplary configurations and methods for the therapeutic facility are not to be considered limiting of scope as such should not be considered as uniquely and exclusively applying to the particular exemplary embodiments being described but rather to all embodiments utilizing a therapeutic facility 1700.

In embodiments of the invention, circuitry 1000S comprises imaging circuitry 1600. Imaging circuitry 1600 in embodiments comprises a packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). In embodiments, Imaging circuitry 16000 may be encapsulated with a polymer layer such as PDMS to prevent contact stress induced damage. Imaging circuitry 1600 can comprise an array of photodetectors on the substrate 200 positioned in close proximity to the site of interest within the subject's body 2000 can provide high spatial resolution imaging without the need for a lens-based focusing due to the proximity of the photodetectors to the tissue. Imaging circuitry 1600 comprise a light source comprising or connected to an optical fiber or an LED to provide illumination to the photodetectors for imaging the tissue of interest.

Thus, the above configuration, designs, and techniques enables the circuitry to be in direct contact with and in some cases conform to the tissues in the body. Such conformal contact with tissues enhances the capabilities of the medical devices, methods, and systems disclosed herein.

Exemplary configurations for the circuitry 1000S including sensor 1100, processing 1200 and 1200A, output 300, and therapeutic facility 1700 methods, configurations as well as fabrication techniques will be described below and referred to in the following discussion with reference 1000B (and subsequently 1000N, 1000T, and 1000E). However, it should be understood that any embodiment of circuitry (and therefore its electronic devices, components, and other functional elements) described herein in shall apply to any of the exemplary embodiments. The exemplary configurations and techniques are not to be considered limiting of scope. It will be readily appreciated that the circuitry elements, configurations, and fabrication techniques of the present invention, as generally described herein, could be utilized, arranged or otherwise implemented in a wide variety of different ways. Also, and by way of clarification, the circuitry configurations and functional elements as well as the fabrication techniques described for this (and all exemplary embodiments) described herein shall be considered to apply to each or any of the embodiments disclosed herein and as such should not be considered as uniquely and exclusively applying to the particular exemplary embodiments being described.

Figure 7:
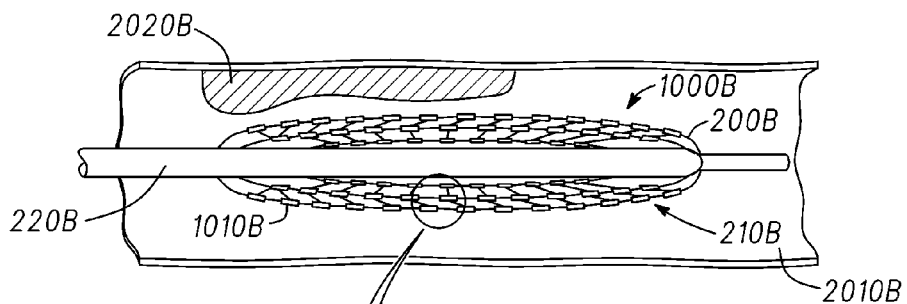
FIG. 7 depicts an embodiment of the invention wherein stretchable circuitry is applied to a balloon catheter, in which the balloon catheter is deflated.

FIG. 7 shows an embodiment of the invention wherein circuitry 1000B is stretchable and on an expandable/stretchable substrate 200B which in this embodiment is an inflatable body. In some embodiments (such as the one shown in FIG. 7) the inflatable body is a balloon on a catheter 220B. The skilled artisan will appreciate that the balloon and catheter together are referred to as a "balloon catheter" 210B, which is a type of catheter with an inflatable balloon at its tip and which is used during a catheterization procedure for various medical procedures such as to enlarge a narrow opening or passage within the body. The deflated balloon catheter 210B is positioned, then inflated to perform the necessary procedure, and deflated again in order to be removed.

FIG. 7 shows the balloon catheter 210B in a relaxed or deflated state, which is inserted into a lumen 2010B, which in this embodiment is an artery. FIG. 7 also shows arterial plaque 2020B formed on the inner wall of the artery 2010B. The stretchable electronic circuitry 1000B is configured in the manner described above with reference to the various embodiments of stretchable circuitry 1000B and is thus applied to the surface of the substrate, i.e., inflatable body 200B according to the applicable techniques described above. In embodiments, the circuitry 1000B utilizes complementary metal-oxide semiconductor (CMOS) technology.

Figure 7A:
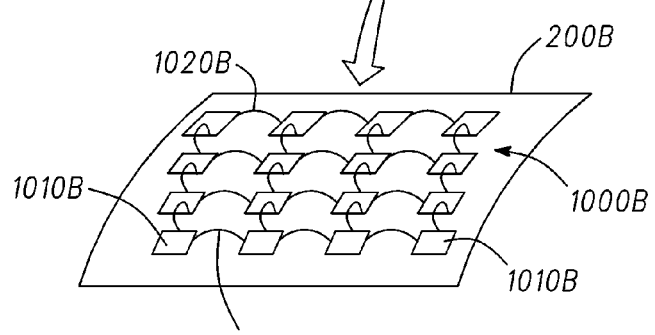
FIG. 7A is a expanded view of the circuitry shown in FIG. 7.

FIG. 7A shows a detailed view the circuitry 1000B while the device is in a deflated or unexpanded state. As mentioned above, the circuitry 1000B of the invention comprises at least one device, which is depicted in FIGS. 7 and 7A as discrete device 1010B. As described above, in embodiments the electronic device is in electronic communication with at least one other device 1010B. In embodiments, the devices are arranged in a "device island" arrangement as described herein and are themselves capable of performing the functionality of the circuitry described herein including the that which has been described for elements 1100-1700 in FIG. 1, the exemplary embodiments below, or portions thereof. Thus, in embodiments, such functionality of the devices 1010B (or any such electronic device herein) can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof.

In embodiments, in order to accommodate the devices 1010B, which may be rigid, to the demands of an expandable and stretchable substrate 200B such as a catheter balloon 210B, the devices 1010B are fabricated such that they are located in discrete and isolated "device islands" and are electrically interconnected with stretchable interconnects 1020B, or interconnects configured to accommodate an expandable or stretchable surface. As with all elements of the circuitry 1000B, the interconnects 1020B can be fabricated according to techniques described herein and thus may be configured differently than what is depicted and described with reference to this exemplary embodiment.

Figure 8:
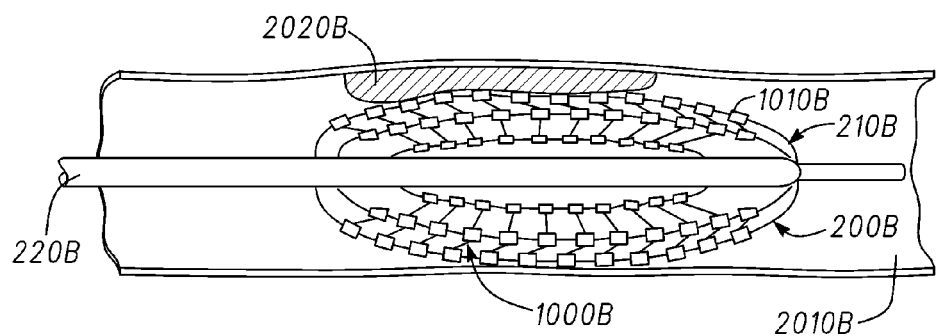
FIG. 8 depicts an embodiment of the invention wherein stretchable circuitry is applied to a balloon catheter, in which the balloon catheter is inflated.

In this exemplary embodiment, it can be seen that the interconnects 1020B are flexible and thus able to accommodate the stretching caused by the inflation of the balloon 210B (shown in FIG. 8). Thus, the entirety of the circuitry 1000B is expandable or stretchable. In the embodiment shown in FIG. 7A, the interconnects 1020B are buckled or non-coplanar when the substrate 200B is in a deflated state. When inflated (as shown in FIG. 8), the interconnects 1020B become either coplanar or non-buckled so as to accommodate the increased distance between the devices 1010B upon inflation. Such buckling, non-coplanar interconnects, as well as circuitry having similar properties, are described elsewhere herein and apply.

As mentioned above, in embodiments, the electronic communication between the devices and/or between said devices and separate (external, for example) devices could be wireless. Therefore, said circuitry 1000B and/or associated devices 1010B may comprise a transducer, transmitter, or receiver capable of such wireless transmission.

The specific fabrication method for such circuitry may depend on the specific circuit classes desired to incorporate into the device, and the specific characteristics of the circuitry, including those of the devices, the interconnects, etc., and include, but is not limited to, those disclosed with respect to this exemplary embodiment. A non-limiting example of the complete fabrication steps of an exemplary embodiment of the invention, i.e., a catheter balloon instrumented with temperature sensors, is described in the following paragraphs. It should be noted that while the embodiment described below refers to an inflatable system (specifically a catheter balloon), the skilled artisan will appreciate that such principals of operation will apply to situations where the substrate on which the circuitry is applied is otherwise stretchable or expandable but not inflatable, or where the substrate is inflatable but not necessary stretchable as described above with reference the FIG. 1 and the discussion of substrates.

In embodiments herein including but not limited to those described herein for balloon catheters, a neural bundle prosthesis, endoscopy, and tissue screening, the arrays of devices, which may include temperature sensors and associated differential amplifiers, buffers, A/D converters, logic, memory, clock and active matrix switching transistors are laid out in a "device island" arrangement. The device islands can be 50 μm×50 μm squares, most of which accommodate a single conventional sensor circuit, e.g., one a temperature sensor, connected to a buffer, that itself connected to an amplifier. The temperature sensor, which may be resistive, diode-based, etc., as described in greater detail below, supplies a signal that reflects temperature (or a temperature change), and the remaining sensor circuitry conditions the signal for subsequent processing.

In embodiments herein including but not limited to those described herein for balloon catheters, a neural bundle prosthesis, endoscopy, and tissue screening, devices accommodate active matrix switches and A/D converters for transforming an analog temperature signal into digital form, and some devices accommodate logic circuitry capable of reading in digital signals and processing them (e.g., to assign a value to the sensed temperature or temperature change). These circuits may output the temperature reading to another module or, and are capable of outputting data or storing it in on-board memory cells.

In embodiments herein including but not limited to those described herein for a balloon catheter, a neural bundle prosthesis, endoscopy, and tissue screening, the circuitry is arranged and designed such that preferably only about one, but not more than about 100 electrical interconnections are required between any two device islands. In embodiments, the circuitry is then fabricated on an SOI wafer (although it should be understood that standard wafers could be used) (1.2 μm thick top Si, 1 μm thick buried oxide) using standard CMOS fabrication technology, and the silicon space in between each island is etched away to isolate each island. The circuits are protected by a polyimide passivation layer, then a short HF etch step is applied to partially undercut the islands. The passivation layer is removed, and then a thin film of SiO2 is deposited and patterned (100 nm thick) by PECVD or other deposition technique combined with a liftoff procedure, such that the oxide layer covers most of the space between devices (a/k/a device islands) except for a region around each device island that is about 5 μm wide. Another polyimide layer is spun on and patterned into the shape of the interconnects. Typically one interconnect may extend from the center of one device to the center of another device. Alternately, two interconnects may extend from each corner of the device to two different device corners. Alternatively, one interconnect may extend from the center of one island edge to the center of another island edge. The interconnect bridges may be about 25 μm wide and may accommodate multiple electrical lines. The polyimide partially fills where the device island is undercut; this serves to stabilize the island later in the release process and to prevent its migration. VIAs are etched into the PI layer to allow metal wires, patterned in the next step, to contact the circuits and connect one island to another. (This step can be repeated to form additional sets of wires located above the first set). Another PI layer is spun on (covering the wires and everything else). The PI (both layers) is then isolated by etching with a deposited SiO2 hard mask, in O2 RIE. PI located outside the devices and bridges is etched, as well as PI covering areas that are meant to be externally electrically interfaced, and small areas leading to the underlying oxide. Etch holes may be formed if necessary and then transferred through the silicon or metal layers by wet and/or dry etching. The underlying buried oxide is etched away using HF etchant to free the devices, which remains attached to the handle substrate due to the first polyimide passivation layer which contacts the handle wafer near the border around the devices.

If the HF etch is not controllable enough and seeps under the PI isolation layer and thereby attack the CMOS devices, then prior to the first PI passivation of brief Argon sputtering can be done to remove any native oxide followed by amorphous silicon sputtering followed by the PI passivation and the rest of the processing. After rinsing, the devices are left to air dry.

Figure 9A:
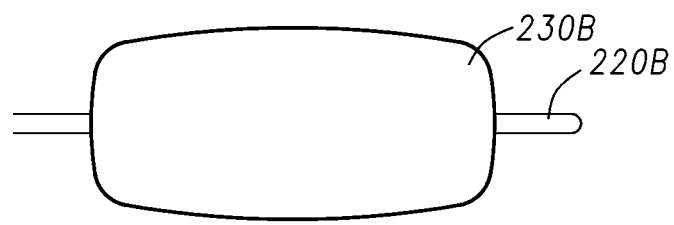
FIG. 9A shows a side view of a balloon with a PDMS layer wrapped around the surface of the balloon.
Figure 9B:
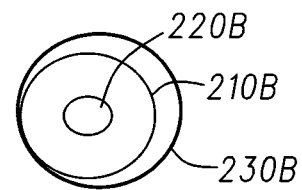
FIG. 9B is a cross-sectional view which shows the catheter, the surface of the balloon, and the thin PDMS layer applied to the balloon.

In connection with some embodiments, after drying, they are picked up with a PDMS stamp, and transfer printed onto either the surface of the substrate, which in this particular exemplary embodiment is an inflatable body such as a catheter balloon 210B, or a surface of the inflatable body coated with a thin PDMS layer, or a separate thin PDMS layer (that may later be wrapped around the inflatable body). FIG. 9A shows a side view of a balloon with the PDMS layer 230B wrapped around the surface of the balloon. FIG. 9B is a cross-sectional view which shows the catheter 220B, the surface of the balloon 210B, and the thin PDMS layer 230B applied to the balloon.

It is also possible for a thin PDMS mold to be made of half the (inflated) balloon shape (in embodiments involving an inflatable body), such that it can be stretched flat, and have circuits transferred onto it in the flat state, and then released to pop back into the half-balloon shape; this half-balloon can then be easily attached to the real balloon, and may even be glued. It is noted that in some cases where the circuits are on the outside of the balloon, the bridges (also referred to as interconnects and physical electrical connections herein) pop or buckle outward when the devices are compressed or the expendable/inflatable body is otherwise in a relaxed or deflated state. In the inflated state, the bridges 1020B should be fairly non-buckled and/or coplanar with the surface of the substrate 200B so that in the deflated state they can buckle to accommodate the significant compressive stress.

Alternately, this process can be repeated with a mold made in the deflated state of the balloon, and stretched beyond flat so that it is significantly expanded, such that after the circuits are transferred and the mold is released, they compress significantly. In this case, they should be compressed enough so that after transfer to the actual balloon, when it is fully expanded, the bridges are nearly flat or fully extended and almost non-buckled.

In embodiments where the circuitry 1000B is directly transferred to the balloon, the PDMS stamp should be made thin (~100-500 μm in thickness) and thereby compliant enough to conform to the shape of the balloon.

In embodiments where the circuitry 1000B is first transferred to a separate thin PDMS layer, the PDMS layer may be on a rigid substrate so that the transferring can be done easily. Then the PDMS layer can be peeled off the substrate and wrapped around the balloon 210B either in the inflated or deflated state, depending on whether the circuitry 1000B was transferred with any prestrain or not. It may be desirable to make the circuitry in a 1D array rather than a 2D array. In this way, the thin PDMS layer is a long, narrow ribbon that can be easily wrapped around the balloon 210B so as to cover the entire balloon 210B surface.

Figure 10A:
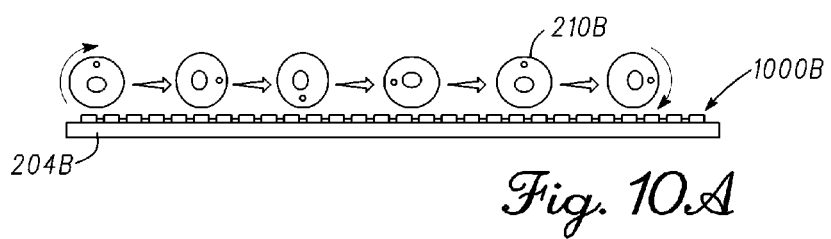
FIGS. 10A, B, and C depict a process for applying stretchable circuitry to the surface of a catheter balloon.
Figure 10B:
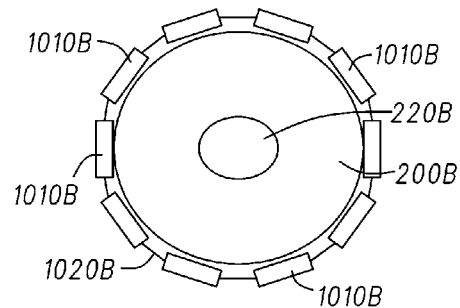
FIG. 10D is an embodiment of a pressure sensor utilized with embodiments of the invention.
FIG. 10E is a cross-sectional view of a tri-lumen catheter according to embodiments of the invention.
FIG. 10F schematically depicts a multiplexor according to an embodiment of the present invention.
Figure 10C:
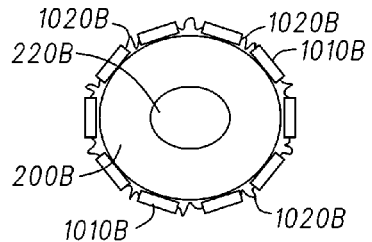

In embodiments, to apply the circuitry, the balloon 210B can be directly rolled along a planar array of circuitry 1000B on PDMS carrier substrate 204B as shown in FIG. 10A. The balloon can be subsequently deflated and/or re-inflated. Deflation can cause the interconnects in the circuitry to buckle and take on compression forces imposed by deflation as shown in FIG. 10C, while inflation causes the interconnects to be substantially coplanar with the substrate (as shown in FIG. 10B). This principle applied to inflatable, stretchable, and flexible embodiments herein. Further, it should be understood that the described stamping methodologies applied to the balloon catheter can be applied to stamp the electronic circuitry in all of the embodiments described herein.

In embodiments circuitry may be encapsulated (in embodiments, while in its compressed state) with another layer of PDMS, or a liquid layer of PDMS followed by an upper layer of solid PDMS to make a fluid encapsulation.

In embodiments where the circuitry is facing outwards on the balloon, it may be electrically externally interfaced at conductive pads that should be designed to be located at the base of the balloon. Anisotropic conductive film (ACF) connectors can be used to interface to these conductive pads, by pressing and heating the film onto the pads. The film can then run down the length of the catheter since it is so thin and flexible.

In embodiments where the circuitry is encapsulated or facing inwards, they may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable circuitry may be electrically interfaced to an ACF prior to the transfer or encapsulation process.

As described above, in embodiments the circuitry is powered externally optically, using the catheter tube as a waveguide and having PV cells made in a stretchable format in addition to the rest of the circuitry. In addition, LED islands may be made to perform optical data communication down the catheter waveguide. Alternately, thin film batteries may be used to power the circuitry. Alternately, RF communication circuits on the device may be used to wirelessly communicate outside of the body, and may also receive RF power to power the circuits.

In embodiments, the substrate is polymeric, e.g., polyimide or polydimethylsiloxane (PDMS). The single-crystal semiconductor devices themselves may be created on a silicon-on-insulator (SOI) carrier wafer in accordance with a circuit design implementing the desired functionality. Interconnect systems (as described herein) may also be created during this step to join smaller device islands. The processed single-crystal devices are removed from the SOI wafer (e.g., by etching) and are then placed in contact with an elastomeric stamp for transfer printing (via methods described herein) onto the desired flexible polymer substrate. In embodiments, the circuitry 1000B is transferred onto the stretchable substrate, which may be pre-stretched prior to transfer. In embodiments, the stretchable substrate serves as the catheter balloon 210B, and can be conformed to the shape of an inflated balloon by a mold. The balloon polymer can be stretched over large strains (greater than 300%) of its relaxed or native state without causing damage to the circuitry 1000B. As described herein, the circuitry can be encapsulated including with additional thin polymer layers to provide further protection from cracks or local contact stresses.

In an apparatus of the present invention involving but not limited to the exemplary embodiment of the balloon catheter presently being described, the substrate (in this embodiment, a catheter balloon 210B) is covered with stretchable circuitry 1000B having an array of devices 210B and may be inserted in a lumen 2010B of the subject's body. The devices may include temperature sensors. The temperature sensors may be, for example, silicon band gap temperature sensor, consisting of silicon diodes. The forward voltage of these silicon diodes are sensitive to changes in temperature. Alternatively, platinum thin-film resistance temperature devices (RTD), which measure temperature based on temperature-induced changes in electrical resistance or thermocouple circuits that sense temperature changes between different thermoelectric materials can be utilized. For thermal resistors, the normalized changes in resistance (R), temperature coefficients of resistors ($\alpha$), are related to the change in temperature (T) by $$\Delta R/R = \alpha T.$$

Platinum (500 Å) and an adhesion layer of chromium (150 Å) can be patterned and deposited on SOI wafers using thermal evaporation via e-beam to define individual RTD sensors. The RTD sensors can be integrated with CMOS based amplifiers, transducers, computation logic elements, and A/D circuitry on the same device islands as previously described.

Once the circuitry 1000B is transferred onto the inflatable body in this embodiment, a balloon catheter 210B, stretching and fatigue tests can be performed with a mechanical bending stage, capable of applying uneasily tensile or compressive strains in multiple directions or by repetitive inflation and deflation loading cycles. The mechanical bending stages can work in parallel with electrical probing stations (Agilent, 5155C) that are coupled to the circuit semiconductors. In embodiments, to evaluate the performance of the circuitry, multiple cycling of heating and cooling tests can be performed. The circuits can be heated to 160° C. for 5 min. and subsequently cooled down before and after each electrical measurement.

In this exemplary embodiment and in others where it is desirable to protect the circuitry from external damage, an encapsulating thin layer of polymer can be applied to the circuitry, including on the surface of the inflatable body after the circuitry is applied thereto according to the description below and other applicable encapsulation methods described herein. This encapsulating polymer layer may be extremely thin (<100 um) and photocurable in order to allow selective curing in regions where direct contact with sensors is not required. Thus, areas of the device that do require direct or conformal contact with the tissue of interest may be exposed. Such selective encapsulation is described below, but any technique for selective encapsulation described herein may apply. It should be noted all methods of selective encapsulation apply to any embodiment disclosed herein.

In embodiments, the RTD temperature sensors may be preferentially exposed for direct contact during photocuring. There are several polymers that may be used for preferential photocuring of the encapsulating layer, including but not limited to polyethylene glycol (PEG) with 2-hydroxy-2-methylpropiophenone photoinitiator. The photocurable PEG encapsulation cures once it is exposed to ultraviolet light. Photomasks designed using AUTOCAD can be printed to allow preferential curing of the surface of the inflatable body. These masks can be inserted as a filter into a UV light source stage coupled with a wide excitation UV filter. Exposure with an aligned mask enables polymerization in strategic regions of the inflatable body. Visual alignment during polymerization can be achieved with a CCD camera.

In embodiments, the substrate (in embodiments an inflatable body such as a catheter balloon 210B) is instrumented with an array of devices 1010B comprising sensors such as temperature sensors can be deployed such that the temperature sensors are positioned in direct contact and or conformal with the surface of plaque in the lumen upon inflation of the inflatable body.

An important advantage realized in this embodiment, and in other embodiments having the flexible and/or stretchable circuitry described herein is that the circuitry (and thus its devices such as sensors) can not only come into direct contact with the surface or tissue of interest (in this case, the plaque and inner surface of the lumen), but also achieve conformal contact with the contours and/or surface features of the surface or tissue so as to achieve greatly improved performance.

In embodiments, the separation distance between sensors can be any that is manufacturable, a useful range may be, but is not limited to, 10 μm-10000 μm. Individual sensors may be coupled to a differential amplifier, and/or a buffer and/or an analog to digital converter. These circuits may be formed on the same, or different, devices than the temperature sensors. The circuits may be laid out in an active matrix fashion such that the readings from multiple temperature sensors can be switched into and processed by one or a few amplifier/logic circuits. These sensor arrays record input signals that can then be channeled from the surface of the balloon to guide wires and a processor using metal electrodes deposited near the junction between the balloon surface and the catheter tubing. Alternatively, gold metal wires may be used to attach the balloon circuitry to the surface of the catheter guide wire using a wire bonder. Signals from the array of sensors can be processed using multiplexing techniques, including those described in published international patent application WO2009/114689 filed Mar. 12, 2009 the entirety of which is hereby incorporated herein by reference. Multiplexor component circuitry located in the base of the catheter guide wire can facilitate this type of data analysis/processing.

Such multiplexing techniques disclosed herein allow for the circuitry (or an operator) to select which active devices should be utilized, or what pattern of active devices should be functioning. Processing facility is configured to generate a user interface on output facility such that the operator may make said selections or adjustments. In some cases the identity or pattern of active devices being utilized is based upon whether (or the degree to which) the devices are in electrical or conformal contact with the tissue of interest. Thus, all embodiments herein are able to generate useful amounts of data even when all electronic devices are not in complete contact with the area of interest on the tissue, but may only be in partial contact.

The device operator may use optical guidance during an x-ray angiography to deploy the balloon catheter once the guide wire reaches the region of the plaque location. The deformable and stretchable nature of the catheter balloon allows temperature measurements at multiple contact points on non-uniform surface contours such as that of arterial lumen and deposited plaque (shown as 2020B in FIGS. 7 and 7A). (The conformal capabilities of the circuitry enable such abilities). Once deployed, the processing facilities described herein process the transmitted signals and produce a spatial temperature map of the plaque in the lumen. This data can be used by the device operator to detect temperature heterogeneity presence along the plaque and determine plaque type. Once plaque type is determined and surface contours are characterized, the balloon catheter can be deflated and removed.

In another embodiment of the invention, the stretchable circuitry 1000B comprises pressure sensor arrays. Such sensor arrays may be silicon-based and utilize piezo-resistive or capacitive sensing, or may be polymer based or optically based. In embodiments, a pressure sensor has a working range and size suitable to the application, and should be amenable to application as described herein and tolerant to the stretching forces it will experience.

Figure 10D:
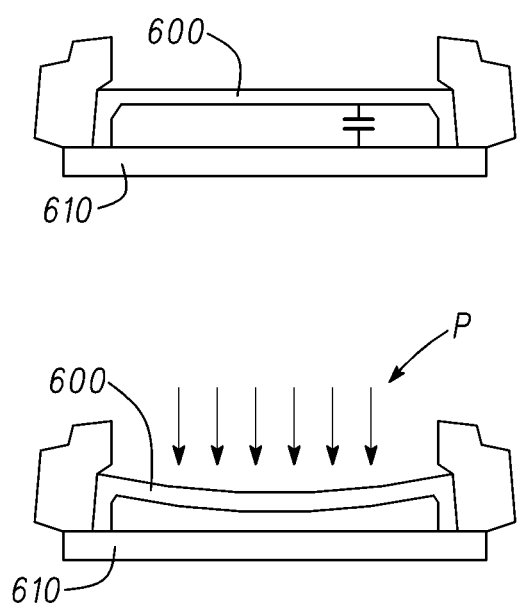

FIG. 10D shows one exemplary pressure/contact sensor which may be utilized with any embodiment described herein requiring a pressure sensor or contact sensor. The pressure sensor comprises a flexible and suspended diaphragm 600 of a flexible material such as thin single-crystal silicon, polysilicon, and/or silicon nitride thin film. The diaphragm 600 can be suspended directly above a base layer of doped silicon consisting of a metal electrode layer extracted from an SOI wafer. The polysilicon diaphragm layer may be formed as a suspended layer by first depositing an SiO2 layer on the silicon electrode 610. The polysilicon may then be deposited on the SiO2 layer, which in turn can be selectively etched. This etching step allows for the formation of a suspended and flexible polysilicon structure. In order to produce diaphragms with a controlled thickness, precise etch rates using HF must be used. This diaphragm with known thickness (2-10 μm thick), material modulus, and surface area and the underlying silicon electrode collectively form a parallel-plate capacitor. The sensor capacitance is a function of distance between the top polysilicon layer and the underlying silicon electrode. The capacitance recordings relate diaphragm deflection (caused by force P) to changes in capacitance.

In embodiments of the invention, the stretchable circuitry comprises an array of contact sensors. The contact sensors are designed to provide an on/off electrical resistance change in response to a pressure, such that when the applied pressure exceeds a predetermined threshold, the sensor provides an electrical signal indicating that it is in contact with, e.g., the arterial wall. One example of how to form a contact sensor is to make a simple mechanical-electrical switch, in which one conductor is mechanically pressed onto another conductor. The lower conductor, located on the surface balloon, consists of a metal wire that is non-continuous in one or more places to form an open circuit. Encapsulated around this open circuit is a diaphragm formed out of PDMS. The PDMS may be molded or etched into a diaphragm shape. The upper wall of the diaphragm is coated with a metal conductor, by standard means of photolithography patterning, electrochemical etching, etching, shadow evaporation, etc. The diaphragm is aligned and bonded to the surface of the balloon. The diaphragm is designed so that when a certain pressure is applied, it bends down to allow the upper conductor to contact and short-circuit the lower non-continuous conductor. This is done by control of the geometry (height and width) and materials of the diaphragm. In yet another non-limiting example, the diaphragm may be made with MEMS techniques, such as sacrificial silicon dioxide layers with a polysilicon bridge on top.

In embodiments of the invention, to measure relative pressure, each pressure sensor can be coupled with reference sensor unit, which has identical electrical characteristics except for a significantly lower pressure sensitivity. Difference in pressure measurements between the sensor and the reference unit enable compensation for many parasitic effects. The reference units may be created by leaving a passivation layer on the top surface of the polysilicon electrode. Having a reference unit along with a pressure sensor unit allows for differential pressure recordings. Once deployed, such sensor arrays can generate data that can be used by circuitry to determine, among other things, the presence and mechanical properties of the tissue such as the presence and properties of an arterial lumen and plaque therein. In embodiments where the substrate is a balloon, such data may also be used to estimate the diameter of the balloon and the lumen and provide feedback to the device operator to end balloon inflation at this point. This type of sensing can be combined with temperature sensor arrays to provide a thorough assessment of tissue mechanical and thermal properties during a single deployment attempt.

In embodiments, data generated by such pressure sensing also allows for creation of a tactile image map of the surface contours of materials such as arterial plaque. Further, this type of mechanical imaging in balloon catheter embodiments can indicate whether a stent has been successfully deployed when the balloon is inflated.

In embodiments of the invention including a therapeutic facility 1700, plaque type is initially determined with data generated by temperature sensors and immediately afterwards, drug-delivery polymers and circuitry embedded in the balloon polymer are activated to cause local cooling and/or release of chemical agents, such as anti-inflammatory drugs, to local sites on the plaque where inflammation is present. In embodiments, therapeutic facility 1700 comprises light emitting electronics (such as LED) could be utilized to activate a drug delivery polymer.

In embodiments of the invention, circuitry comprises imaging circuitry (referred to in connection with FIG. 1 as 1600). Imaging circuitry comprises packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). In embodiments on an inflatable body such as a catheter balloon, all of the circuitry may be encapsulated with a polymer layer such as PDMS to prevent contact stress induced damage of circuitry on the inflatable body, since there is no requirement for direct contact of the lumen with photosensor arrays. An array of photodetectors on the inflatable body positioned in close proximity to the plaque site within a the arterial lumen can provide data used by processing facilities to create high spatial resolution images without the need for a lens-based focusing due to the proximity of the photodetectors to the lumen. The catheter guide wire may comprise a light source, such as an optical fiber or an LED to provide illumination to the photodetectors for imaging the plaque and lumen surface.

In embodiments of the invention, the substrate is covered with ultrasound emitters and receivers to generate data used to produce a lateral deep-tissue image of the plaque and arterial lumen.

In embodiments of the invention, substrate is covered with stimulating and recording electrodes used for measuring plaque conductivity. Since vulnerable plaque is significantly less conductive than stable plaque and arterial tissue, this form of sensor array can help determine the plaque type based on measured conductivity of the plaque. Once the inflatable body is deployed, the electrodes are positioned in direct contact and/or conformal with the plaque deposits and electrical conductivity is measured. Again, this device can be combined with other sensor array types embedded in the stretchable inflatable body to provide multiple sensing and therapeutic functionalities in parallel.

Data collected by sensors at the site of the plaque can be interpreted against a baseline established by deploying the same inflatable body (or a second inflatable body on the same catheter) at a different location, which is free of plaque, in the lumen.

In embodiments of the invention, the array of devices includes temperature detectors, pressure sensors, and photodetectors collectively fabricated in a flexible and stretchable polymer-based balloon catheter substrate. These active device components can be designed using 0.6 µm design feature resolution or smaller. They may be integrated on the devices that are pieces of single crystalline silicon (50×50 µm2; 1.2 µm thick). Once the balloon is inserted in the arterial lumen, the device operator navigates the guide wire leading the balloon to the plaque location. The deployment of the balloon can stop blood flow intermittently. The guide wire is preferably fitted with an optical fiber or LED; the close contact of the imaging arrays to the lumen avoids the need for optical lens arrays, since light from the optical source may pass through the interconnect gap regions between the arrays, scatter through the lumen/plaque, and reach the photodetectors directly.

In this embodiment, the pressure sensor array detects when the inflatable body initially contacts the plaque and generates data used to spatially map the entire region of contact to ensure successful deployment. Circuitry continuously record data generated by the sensors and spatially maps temperature as a way to detect where in the arterial plaque there may be inflammation and macrophage deposits. The device operator may examine the data and decide whether to take immediate action through drug-delivery measures, stent deployment, or further tests on the plaque. The device operator may also utilize light imaging to visualize the plaque. Having integrated pressure sensors and imaging sensor arrays on the balloon, in addition to temperature sensors, allows for creation of a detailed tactile, thermal and visual map of the regions where the balloon contacts the plaque. This type of distributed mechanical sensing and imaging with an array of pressure sensors and photodetectors ensures that the stent and/or balloon contact the entire surface of the plaque.

In embodiments, the lumen may be a pulmonary vein. In such embodiments, the circuitry 1000B comprises devices having sensors that generate data related to the electrical activity of the pulmonary vein which in turn can be used processing facility to generate maps of the circumferential electrical activity of the pulmonary veins. In other embodiments, the sensor may include active electrodes. Such embodiments may generate data for mapping electrical activity of the pulmonary vein. Further, embodiments may also include a pressure sensor and temperature sensor for heterogeneous sensing on a balloon to be deployed in the pulmonary vein for mapping electrical activity. Such embodiments described for the pulmonary vein may apply to any lumen. While in other embodiments, the sensor may include active electrodes for generating data used for mapping electrical activity of the septal wall, atrial wall or surfaces, and/or ventricular surfaces.

Other embodiments may include active electrodes configured to generate data to map electrical activity while the inflatable body is inflated allowing concurrent mapping and ablation. In embodiments, ablation may be effected cryogenically, via laser or via RF energy.

In other embodiments, a contact pressure sensor device generates data used by processing device maps force per unit area applied to the ostium of the pulmonary vein which can be used for occlusion of the inflatable body, i.e., balloon, during mapping and ablation.

The inflatable body herein may be inflated with fluid of specified temperature. Data related to the temperature of the fluid may be generated by circuitry and thus used to tune the heat output of the electronics, or to calibrate the sensors.

Embodiments, of the balloon catheter can be deployed with a stent that may be fitted around the active sensing and imaging regions of the balloon.

Figure 10E:
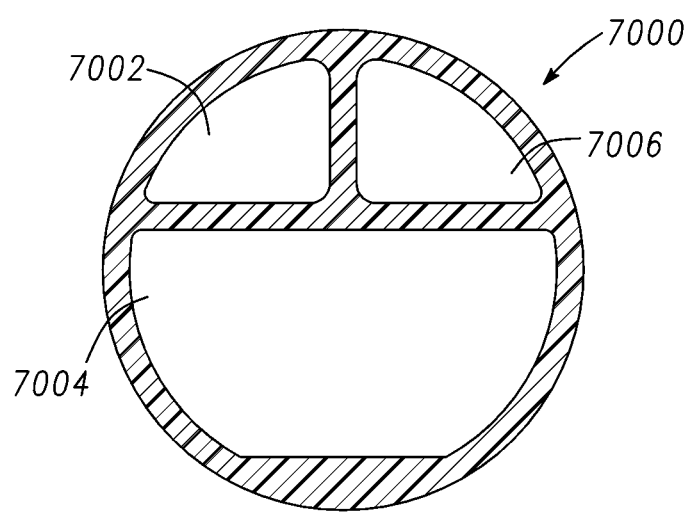

Embodiments utilizing a catheter may utilize the inventive catheter described herein. FIG. 10E shows a catheter 7000 comprising three lumens: guide wire lumen 7002 (houses the guide wire); fluid injection lumen 7006 (channel for fluid which will be used to inflate balloon and or control temperature of the electrodes or active devices on the balloon surface); and the circuitry lumen 7004 (houses the flexible PCB and wiring which will be connected to the DAQ). In the assembly of the catheter system, the flexible PCB is wired for connection to the DAQ and also electrically connected to the stretchable electrode array. This unit is then threaded into the circuitry lumen, of the tri-lumen extrusion as illustrated in with the DAQ-bound wires entering first and exiting through the proximal end of the catheter for connection to the DAQ.

Figure 10F:
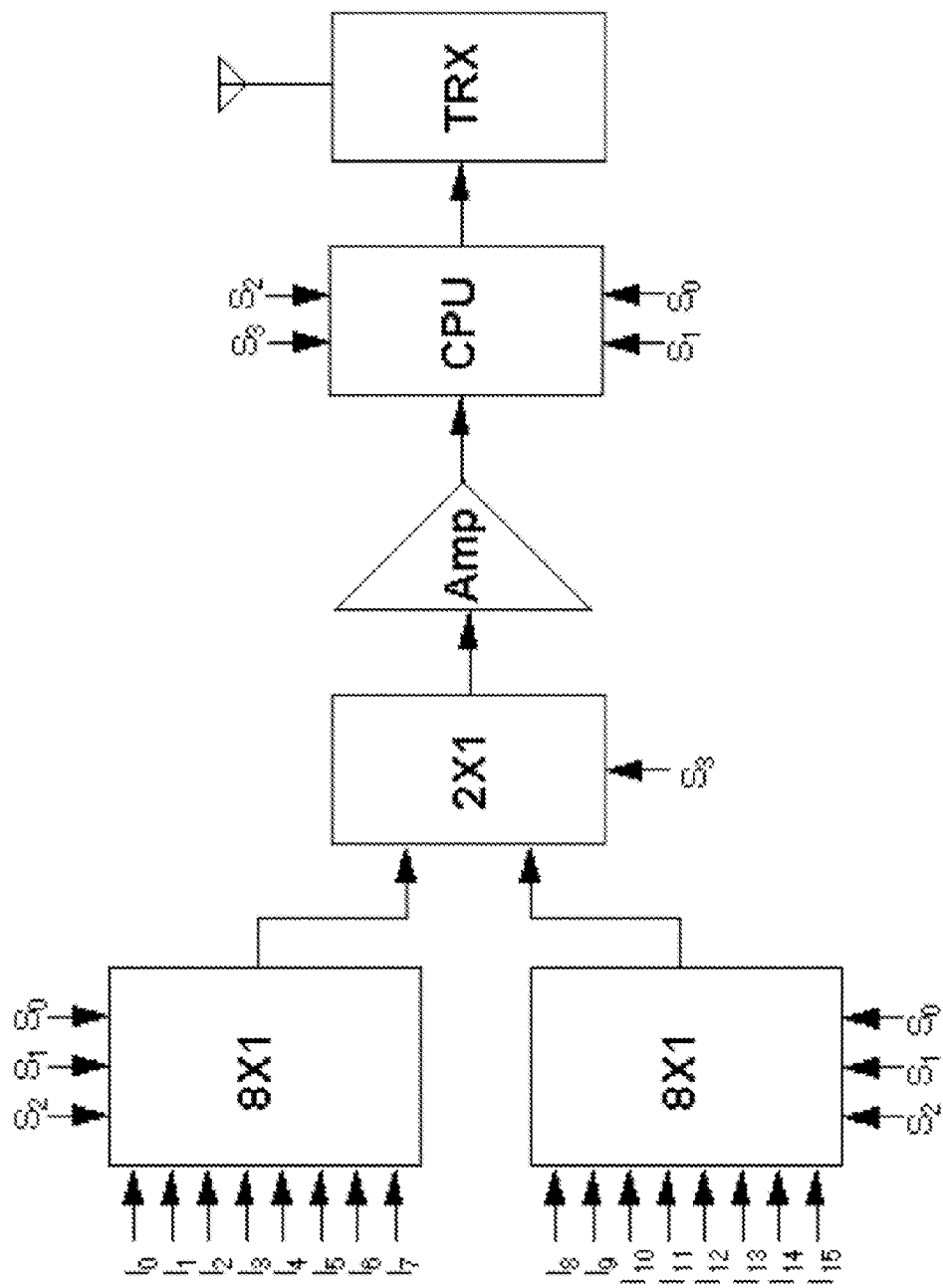

An embodiment of the multiplexer is described in connection with the balloon catheter exemplary embodiment; although it should be understood to apply to other embodiments. FIG. 10F shows a Wireless catheter statistical multiplexer that concentrates 16 (but could be other numbers) asynchronous channels over a single radio link. In FIG. 10E, I0-I15 are the balloon catheter electrodes. 3 cross point switches are used for multiplexing. After the mux, an X time's amp is employed. This is feed into the A/D of the CPU and then transmitted wirelessly. Two wires are needed for power and ground (3-5V @ 5-7.5 mA).

The asynchronous ports can be individually set for speeds to 57.6 Kbps. Hardware (CTS/Busy high or low) or software (Xon/Xoff even, odd, mark, space or transparent) flow control is also set on a port by port basis.

The Wireless catheter statistical multiplexer composite is a wireless link that runs at 57.6 Kbps. It transmits on the license-free ISM or MedRadio band. The link radio modules are easily configured using a terminal or PC connected to the network management port or port one. The range is 4-6 feet or up to 1000 feet with optional external repeater, not shown.

The network management port includes local and remote configuration commands. The Show Configuration Commands allow the system manager to view the configuration settings of both the local and remote multiplexers. Network management features include port and composite loopbacks, capture of a remote or local port, send a test message to an individual local or remote port, set multiplexer ID for node identification and a built-in "data line monitor" which allows the monitoring of the transmit or receive lines at the local multiplexer. A unique feature of the multiplexer is the Copy Command. This command allows a trainer at the host site to "copy" any local or remote port to view exactly what the user is entering.

Such multiplexing techniques allow for the circuitry (or an operator) to select which active devices should be utilized, or what pattern of active devices should be functioning. In some cases the identity or pattern of active devices being utilized is based upon whether (or the degree to which) the devices are in electrical or conformal contact with the tissue of interest. Thus, all embodiments herein are able to generate useful amounts of data even when all electronic devices are not in complete contact with the area of interest on the tissue, but may only be in partial contact.

Referring back to FIG. 1, another embodiment of the present invention involves a substrate 200 (denoted as 200N with reference to certain embodiments below) which is, or which comprises, a prosthetic device which can be inserted by means of a small opening, between severed ends of a nerve bundle. The external surface of the prosthetic device is provided with circuitry according to the disclosure herein wherein the circuitry comprises microelectrodes coupled with amplification and stimulating circuitry.

The prosthetic device can be stretched, inflated or otherwise expanded to conform to the shape of the nerve bundles. This expansion may facilitate the orientation of microelectrodes, strategically positioned on the device, in such a manner as to bridge gaps in nerve bundles. Moreover, circuitry (and in embodiments therapeutic facility 1700) may selectively create connections between a plurality of nerves with the help of onboard logic components or by manual input from an operator utilizing an external device interfaced to the circuitry in the manners herein described. The execution of these actions may occur without movement of electrodes or further physical intervention.

The benefits of this particular embodiment include the ability to electrically reconnect many individual nerves without the need to manipulate them directly, reduce risk of aggravation to nerve damage by using a minimally invasive procedure and its ability subsequently "rewire" the connections one or more times without further surgical procedure. Additionally, this embodiment has the advantage of employing signal amplification and conditioning to adapt the input and output of each "reconnection" to the characteristics and function of a specific nerve fiber.

In this embodiment, circuitry is fabricated according to the methods described above. It should be noted that like other embodiments described herein, devices can be laid out in a device "island" arrangement. The devices are ~50 µm×50 µm2 squares, most of which accommodate one or more components connected to a buffer and also to an amplifier. Some devices accommodate active matrix switches and A/D converters, and some islands accommodate logic circuitry capable of reading in digital signals and processing them, and are capable of outputting data or storing data in memory cells. Circuitry may also contain device components which comprise metal contact pads. The circuits on devices are configured and designed such that preferably only about one, but not more than about 100 electrical interconnections are required between any two device islands or devices.

In embodiments, substrate comprises an elastomeric vessel (which is also referred to herein as an "inflatable body"). In certain embodiments such substrate is in the shape of a disk, said vessel covered with flexible and/or stretchable circuits described herein and having a multitude of electrodes. The disk can be deformed to enable its passage through a small opening in a "deflated" configuration and subsequent deployment in the gap between severed or damaged nerve bundles. Inflation with a viscous fluid is preferable, but it should be clear that a variety of gases, fluids or gels may be employed. According to the methods described herein, the flexible and/or stretchable circuitry is sealed with the miniature electrodes exposed so as to enable them to interact with the surrounding tissue. Each electrode can serve as either a sensing electrode or a stimulating electrode, and is connected to either a sensing or stimulation amplifier depending on device configuration. Signals are routed from sensing electrodes through signal processing circuitry to stimulation electrodes. In this embodiment, any electrode can act as a stimulating or a sensing electrode, depending on the dynamic configuration in effect at the time. Such electrodes may generate data while in electrical contact and/or direct physical contact. "Electrical contact" in meant to encompass situations where the electrodes are generating data regarding a tissue of interest while not necessarily being in direct physical contact. It should be noted that, "functional contact" or "sensing contact" is similarly meant to encompass situations where the sensing devices are generating data regarding a tissue of interest while not necessarily being in direct physical contact.

Figure 11:
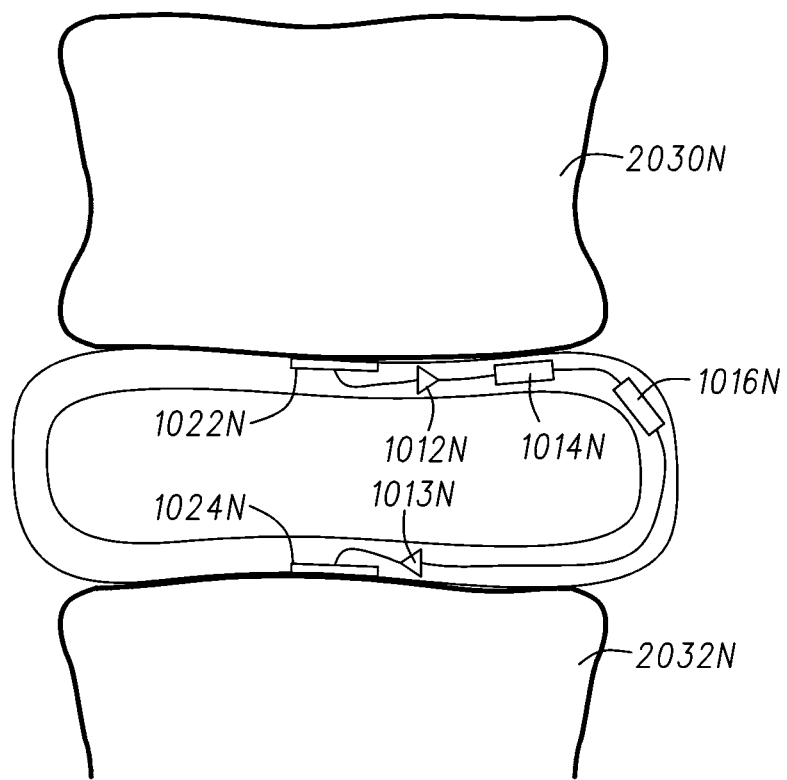
FIG. 11 is a schematic depiction of an embodiment of the invention involving a neural prosthesis.
Figure 12:
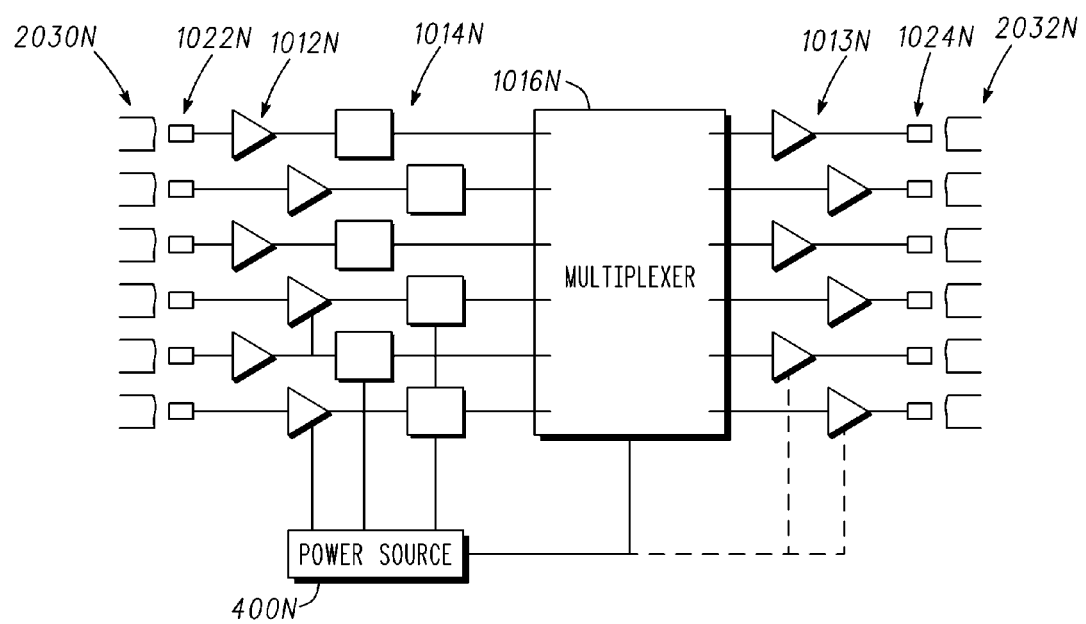
FIG. 12 is a circuit diagram for an embodiment of the invention.

FIG. 11 shows the path of a single nerve pulse in an exemplary embodiment of the invention. Electrode 1022N is in contact with nerve ending 2030N at a given location on the surface of the device. Electrical activity affects the current or potential at the electrode and is amplified by the sensing amplifier 1012N and then optionally undergoes further signal conditioning by block 1014N. From there, the electrical signal flows to the multiplexer 1016N which is configured to match nerve-signal sources and destinations in a way most beneficial to clinically desirable outcomes. The multiplexer 1016N dispatches the signal to the appropriate location on the other side of the device, where it is again amplified by the stimulation amplifier 1013N and finally effects nerve activity of nerve ending 2032 through electrode 1024N. FIG. 12 shows a circuit diagram showing multiple channels for the embodiment just described, Preferred embodiments contain thousands of such paths, enabling the interconnection of many nerves across a nerve gap in a flexible/configurable manner. Notably, the connection between two ends is not determined by the position of the device or at the time of implantation, it can be altered during the procedure or at any time thereafter by altering the dimensions of the invention. Among the reasons for altering the routing of the nerve signals would be observations about mappings of the various nerves, progress of the patient's recovery or effects of neuro-plasticity, or shifts in the relative positions of electrode and tissue in the course of motion or physiological processes. One automated means of configuring the apparatus is as follows.

Figure 13:
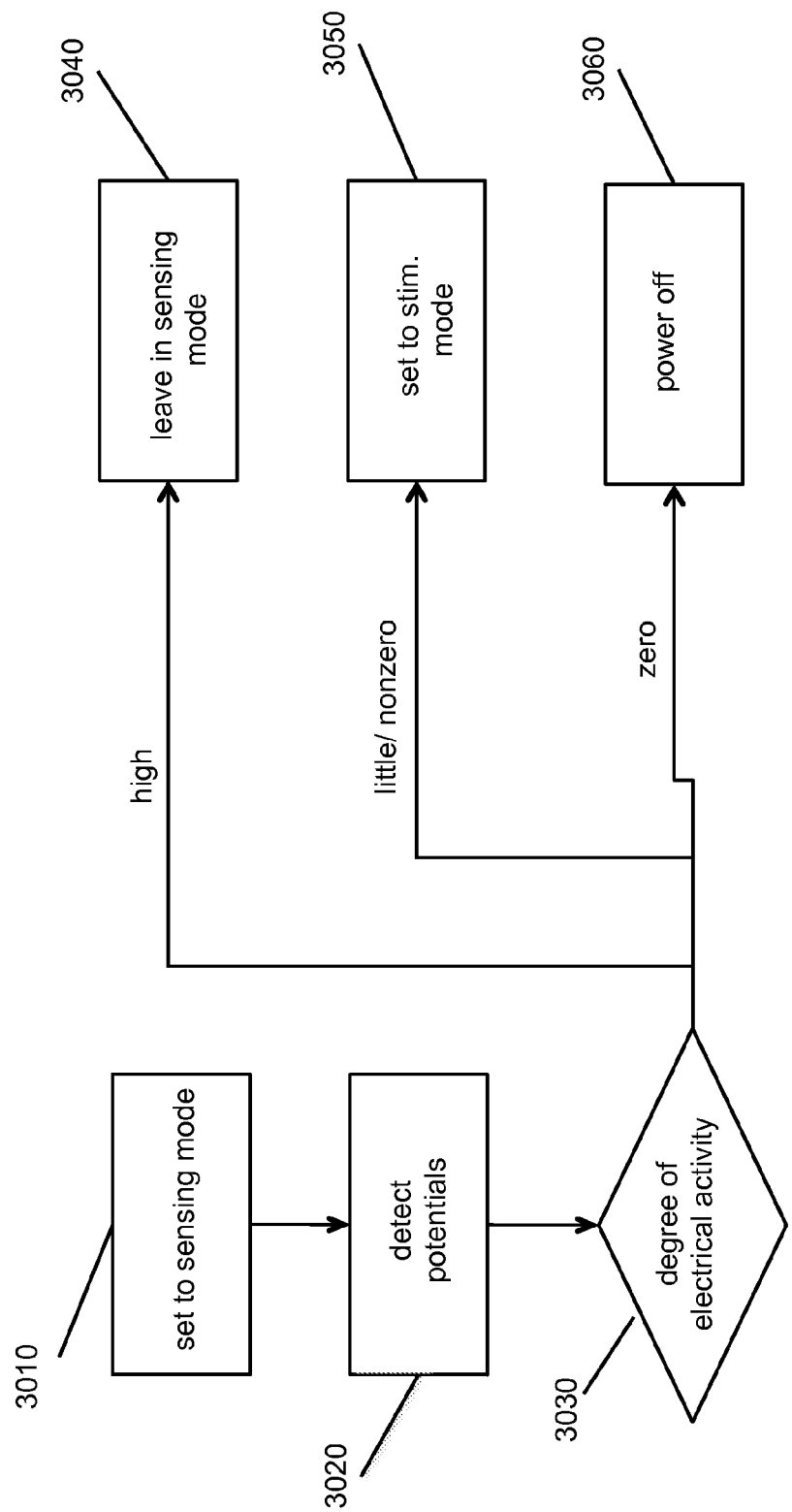
FIG. 13 depicts a process for operating an array of electronic devices according to an embodiment of the present invention.

As shown in FIG. 13, on initial deployment, all electrodes and associated amplifiers are set to be in sensing mode 3010. Electrodes then detect data of the potentials 3020. Electrodes are individually and collectivity affected by the activity of the nerves next to them. These are then amplified and processed (by any applicable processing facility described herein) to determine the presence or degree of electrical activity 3030, which is then used to configure the channels in the following manner: as shown in step, 3040 electrodes those regions with high electrical activity are left in sensing mode. Step 3050 shows that electrodes in regions with less, but non-zero, activity are switched to stimulation mode. In step 3060, electrodes in regions with no activity are turned off to conserve power and avoid interference. The full nature of the electrical signals, including their amplitude and frequency, are optionally utilized by this embodiment to deduce the original anatomical function of the nerve tissue it is contacting.

In embodiments, circuitry makes measurements of conductivity between electrodes. These measurements correlate with the electrical activity of physiological structures and hence can be used by circuitry or external processing facility 1200A to create a contour map of conductivity. In embodiments, such map can be used to enhance the configurations of the electrodes and multiplexing strategy.

As mentioned elsewhere herein, sensors can also include temperature or pH sensors or orientation sensors, and the measurements obtained from them used to improve the connections.

In other embodiments, the device does not simply provide one-to-one correspondence of electrodes. Stimulation of a given output electrode can be based on signals from more than one sensor and/or more than one input (sensing) electrode, or the stimulation of many electrodes based in signal from just one input electrode.

After initial configuration, the disclosed invention can be reconfigured one or more times thereafter, by establishing a wireless control link to the device from outside of the body (in the manners described herein) and using additional information to make decisions about the best configuration. For example, the clinician can communicate with the patient, asking him or her to attempt to move certain muscles, or to report absence or presence of certain sensations. Since as mentioned above, the substrate is biocompatible, the reconfigurations can be done after a surgical incision has successfully healed and without anesthesia or further trauma to the patient, enabling the connections between nerves to be slowly optimized for maximum benefit over a period of time. The benefit of the present invention is that these adjustments do not require any physical or surgical manipulation, thus avoiding further risks and suffering to the patient. Furthermore, subsequent configurations can be integrated into a comprehensive rehabilitation program.

The circuitry is distributed throughout substrate, which provides a high density of electrodes while allowing the invention to be realized in a variety of sizes and shapes most advantageous to a specific anatomical location. The flexible/stretchable nature of the circuitry enables it to achieve—and maintain—close contact with irregular surfaces of transected nerve fibers, providing a significant advantage over electrode systems that have to be individually positioned or require nerves to be flat planar surfaces that are not usually found in nature. In addition to making initial contact possible without either explicit surgical placement (which would be impractical for thousands of individual nerves) or perfectly flat surfaces, the present invention has the benefit of maintaining contact (electrical or physical) with a large number of nerves despite physical movement, physiological processes (such as inflammation or scarring), or the passage of time, since a near-uniform pressure is applied to all of the electrodes by the fluid filling the apparatus.

Figure 14:
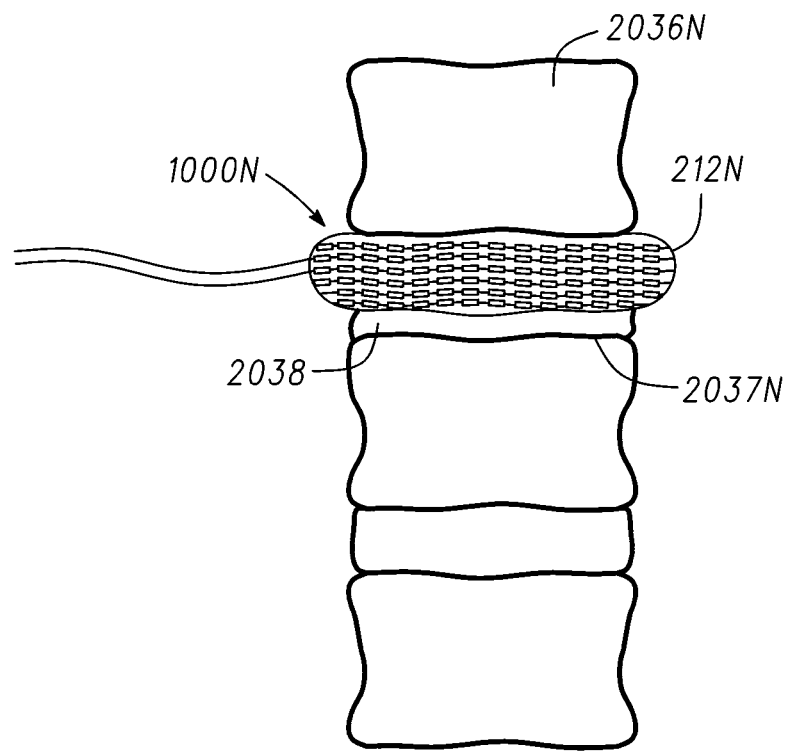
FIG. 14 depicts an embodiment of the invention involving a neural prosthesis.

FIG. 14 shows the device implanted in the spine of a subject having neural damage. 2036N and 2037N are vertebrate of a spine. Cartilaginous disc 2038N disc is also shown. Inflatable disk 212N having circuitry 1000N is shown being inserted into the area of damage. Once in place, disk 212N is inflated thus contacting the nerves as described above.

Figure 15:
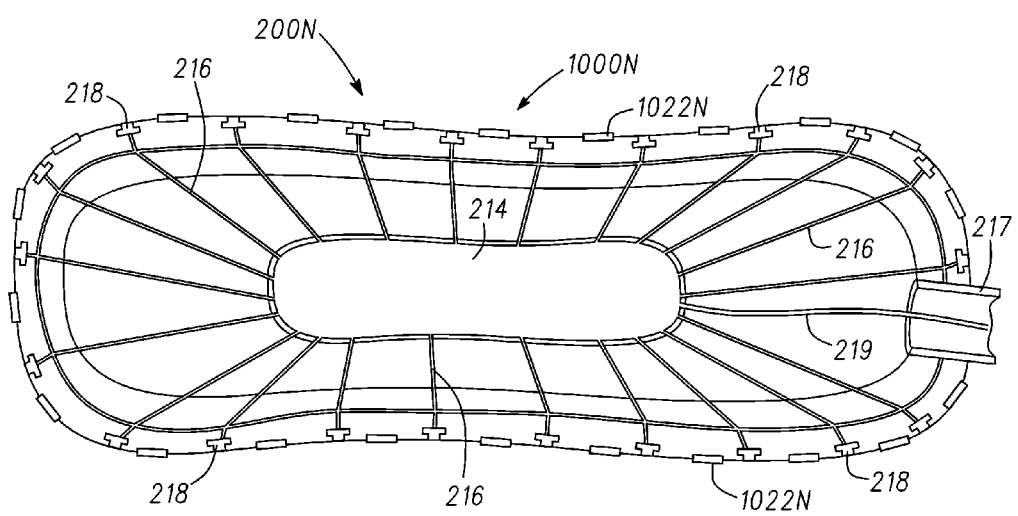
FIG. 15 depicts an embodiment of the invention having a reservoir for holding and delivering a therapeutic agent, along with valves controlled by the circuitry to deliver said therapeutic agent.

Other embodiments could include a therapeutic facility (such as 1700 described in FIG. 1) invention would also incorporate drug delivery capabilities alongside electrode arrays. FIG. 15 shows such an embodiment. Circuitry 1000N comprising electrodes 1022N, for example, is provided on the outside surface of disk 200N, which may or may not be inflatable. A drug reservoir 214N is provided, which communicates with the surface of the disc 200N by way of channels 216N. At the end of the channels 216N are valves 218N which in embodiments are MEMS valves, which are connected to and controlled by circuitry 1000N which comprises the therapeutic facility 1700. Refill line 219N is connected to the reservoir which allows for the reservoir 214N to be refilled in embodiments. One benefit of such a capability is to deliver drugs to reduce rejection or scar formation at the interface between the tissue and the apparatus. The release of a drug can be controlled by means of the MEMS valve 218N and delivered only in areas where processing facility 1300 has determined, by being so configured, that previous measurements (such as temperature or conductivity) have indicated that it may be of greatest benefit. Other embodiments include individual cavities containing the drug, which when consumed necessitate the replacement of the device if further drug therapy is desired.

In another embodiment of the invention, electrodes on substantially flat substrates, in embodiments, sheets that comprise stretchable and/or flexible electronics may deliver stimulation to the brain, patch of exterior skin, neural bundles, internal organs, and the like. Higher density electrodes (such as <1 cm spacing) may be enabled by reducing wiring complexity, including communications facilities with each electrode or to groups of electrodes, by including amplification and multiplexing capabilities within array of electrodes, and the like.

Other embodiments of the invention, involve endoscopic imaging devices having improved design efficiencies in terms of power and volume. Embodiments of the present invention incorporate conformal, curvilinear electronic components for the purpose of volume reduction, imaging enhancement, and increased functionality.

It will be appreciated that the approach of the embodiment described below may be applied to conventional tubular endoscopy devices and capsule endoscopy devices, as well as any device utilizing the herein described curved focal plane arrays of photodetectors that are comprised in a CMOS imager. It should be noted that such curved focal plane arrays can be utilized in conjunction with any embodiment described herein and that all other embodiments described herein including those related to the circuitry including and the elements thereof are intended to be utilized as applicable in the endoscopy embodiment described below. Curved silicon optical sensor arrays have significant advantages over conventional planar arrays. These advantages include a reduced number of optical elements, reduced aberrations including astigmatism and coma, and increased off-axis brightness and sharpness.

In embodiments of the invention, an endoscopy device is fitted with a curvilinear array of sensors and/or transducers, e.g., on the exterior surface thereof, thereby reducing the required volume of the device. This approach is particularly advantageous in reducing the overall size of an endoscopy device, allowing integration of additional diagnostic and therapeutic and/or sensing functionality including any described herein an the following examples, ultrasound, pressure sensing, temperature sensing, pH, chemical sensing, targeted drug delivery, electrocautery, biopsy, laser, and heating), and increasing the allowable battery size. Increasing the power storage of a capsule endoscopy device can lead to improvements in image quality, image compression, transmission rate, number of images captured, and the intensity of illumination produced by the LEDs.

In embodiments of the invention, a capsule endoscopy device and its internal circuitry are both made flexible and/or stretchable from any of the materials described for substrates including other biocompatible materials apparent to those skilled in the art. Such a flexible/stretchable endoscopy device may have increased ease of motion along the GI tract and also increased viable volume. In other embodiments, the device may have a rigid capsule-like structure with electronics conformally fitted in the inner and/or outer shell of the capsule. The exposed surface—either a rigid ellipsoid shell or a flexible or stretchable layer—is fabricated from a material resistant to the harsh digestive environment that the endoscopy device will encounter, but which is also is biocompatible and harmless to the patient's internal anatomy. Other properties of biocompatibility of the outer surface are described herein.

The stretchable electronic components of the endoscopy device have been described herein in connection with the discussion of circuitry in all embodiments. In embodiments, circuitry comprises sensing and imaging arrays for monitoring features that are inside of bodily cavities and lumen such as the GI tract. As described above, the functionality may reside in circuitry comprising devices which may comprise device islands or vice versa. The islands house required circuitry and are interconnected mechanically and electronically via interconnects such as those described herein. The interconnects, in turn, preferentially absorb strain and thus channel destructive forces away from the device islands. They provide a mechanism by which the integrated circuits can stretch and flex when a force is applied. The device islands and interconnects may be integrated into the casing or encapsulating shell of the endoscopy device by transfer printing, as described below. Encapsulation of electronic devices and system/device interconnect integration can be performed at any of a number of stages in this process.

As with other embodiments described herein, the circuitry used in the electronic devices may comprise standard IC sensors, transducers, interconnects and computation/logic elements. In embodiments, electronic devices are typically made on a silicon-on-insulator (SOI) wafer in accordance with a circuit design implementing the desired functionality. Semiconductor devices may be processed on suitable carrier wafers which provide a top layer of ultrathin semiconductor supported by an easily removed layer (e.g. PMMA). These wafers are used to fabricate flex/stretch ICs by standard processes, with particular island and interconnect placement being tailored to the requirements of a particular application. "Ultrathin" refers to devices of thin geometries that exhibit extreme levels of bendability. They are typically less than 10 µm in thickness.

The above discussions of fabrication of circuitry applies to endoscopy embodiments. However, the following discussion will describe a transfer step for embodiments related to endoscopy (but not necessarily limited thereto). In such embodiments, the circuitry is primarily used to enhance the imaging system of the device.

Imaging with a curved optical sensor array (instead of a planar array) is used in conjunction with a lens, illuminating LEDs, battery, computing unit, antenna and a radio transmitter. Wired telemetry is used for conventional tube endoscopy. A passive or active matrix focal plane array is fabricated using one of the stretchable processing techniques described above. The array includes single-crystal silicon photo-detectors and current-blocking p-n junction diodes. Images captured using the array are minimally processed by onboard computing and transmitted (wired or wireless) to an external receiver for further processing.

The focal plane array described below could be considered part of any imaging facility described above. The individual photo detectors may be networked via interconnect systems in accordance with the present invention. These devices are found on islands and are connected by interconnects such as those interconnects described herein. In embodiment, films of polyimide support certain regions and encapsulate the entire system. Such a focal plane array can thus be incorporated into the endoscopy device.

Figure 16:
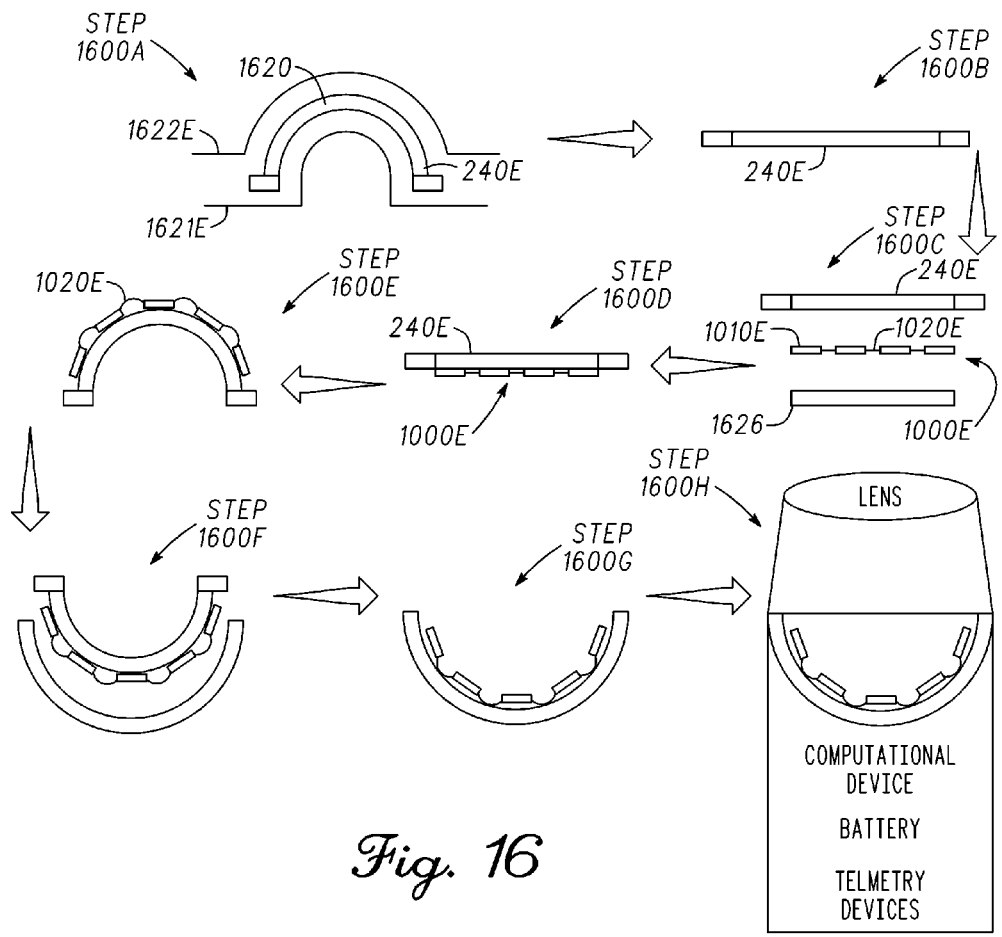
FIG. 16 depicts a process for assembling curvilinear circuitry according to an embodiment of the invention.

FIG. 16 illustrates the process of making a such focal plane array. The first step is fabricating the necessary circuitry 1000E, which in this embodiment is a focal plane array, is the creation of a suitable geometric transfer stamp to facilitate this process. In this embodiment, the circuitry is represented herein as 1000E (although it should be understood that is contemplated that this circuitry 1000E relates to and may be used with other circuitry embodiments described herein).

At Step 1600A, an appropriate stamp (also referred to as transfer element) 240E is created by casting and curing poly(dimethylsiloxane) (PDMS) in the gap between opposing convex and concave lenses with matching radii of curvature (1621E and 1622E respectively). The radius of curvature should reflect the optimal parabolic curvature useful for a non-coplanar imager. At step 1600B, the cured curved transfer element 240E (the removal of which from lenses stamping mechanism not shown) can be stretched using a specially designed mechanism which provides outward radial forces (in embodiments equal outward forces) along the rim of the stamp to create the planar pre-strained geometric transfer element. The transfer element should return to its initial size when relaxed. Transfer element 240E should also be large enough in its planar configuration to contact the entire area of electronic device islands on the donor substrate.

A component of the circuitry 1000E in this embodiment is the processed electronic devices joined by interconnects 1020E. At step 1600C, the circuitry 1000E is brought into contact with the planar transfer element 240E, which adheres to the former via sufficiently strong van der Waals interactions. The transfer element 240E is peeled back, thereby removing the focal plane array, i.e., circuitry 1000E, from its handle wafer 1626, shown at 1600D. After the focal plane array 1000E is removed from the handle wafer, the tension in the stamp is released and the contacting layers, i.e., the focal plane array and the stamp, both take initial geometric form of the stamp (shown at 1600E). The focal plane array 1000E compresses and the networked interconnects 1020E of the array buckle to accommodate the strain. The buckled focal plane array 1000E is then transferred to its final substrate (shown in steps 1600F-H) which has a matching radius of curvature and is also in communication with the battery, antenna and a radio transmitter via electrical contacts. This transfer occurs by contacting both surfaces and is aided by the use of a photocurable adhesive. The adhesive provides sufficient attraction such that when the PDMS stamp is removed, it releases the curvilinear array of photodetectors onto the imaging system port. The curved focal plane array is then connected to the rest of the imaging electronic components via electrode contact pads on the outer perimeter of the array.

Figure 16A:
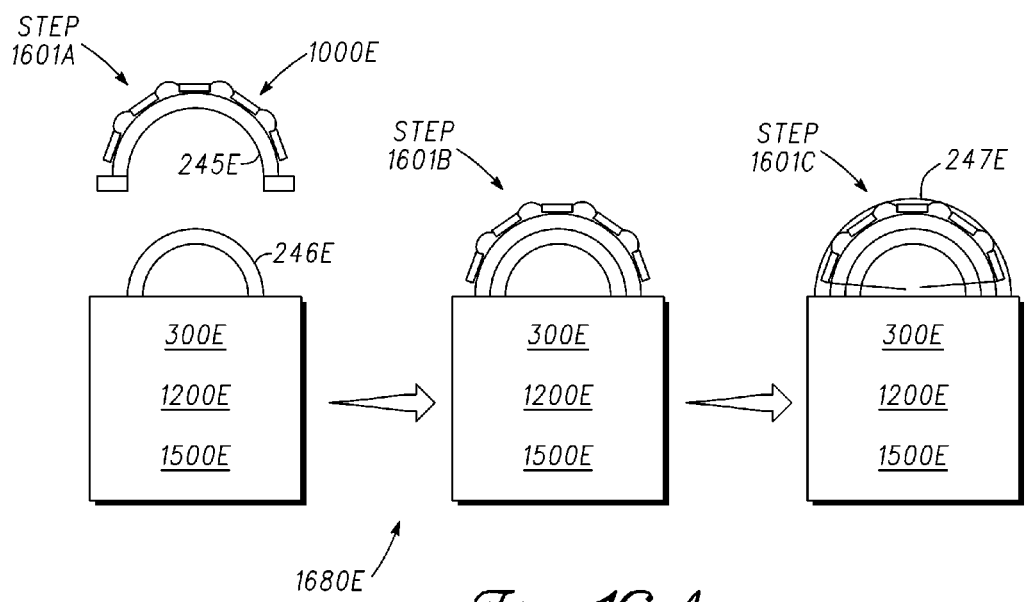
FIGS. 16A and B depicts the process for applying a curvilinear array of circuitry to an endoscopic device according to an embodiment of the invention.

In another embodiment shown in FIG. 16A, and endoscopy device 1680E comprising power 300E in the form of a battery, processing facility 1200E, and data transmission facility 1500E is shown. Step 1601A shows convex focal plane array 1000E that is adhered to the outer shell of the endoscopy device 1680E by, for example, a geometric transfer stamp 245E. After lifting the focal plane array off the handle wafer with the planar pre-strained PDMS (as described in connection with previous FIG. 16), it can be relaxed and directly deposited onto the distal end of the endoscopy device 1680E, which is provided with a receiving substrate 246E having, for example, a photocurable adhesive. After deposition onto the endoscopy device 1680E (status shown as 1601B), electrical contacts are made from the array 1000E to the internal circuitry of the endoscopy device 1680E. At 1601C, all of the exposed circuitry can be sealed with a suitable polymer and/or metal layer (e.g. parylene, polyurethane, platinum, gold) 247E.

Micro-lens arrays may be required for such optical array systems. However, with proper illumination and negligible distance between the optical array and the surface being imaged (e.g. near field imaging), this requirement may be nullified.

In yet another embodiment, a focal plane array, also referred to as circuitry 1000E (as described above) is conformally wrapped around an endoscopy device such that it points in an outward radial direction from the long axis of the device. This is achieved by completing the same planar stretchable processing steps mentioned above and transferring the circuit with a different specialized polymeric stamp. The transfer stamp may take the form of a planar rectangular strip. Each polymeric strip is pre-strained by thermal expansion (heat to around 160° C.) or by applying uniform radial strain. This pre-strained polymer is then positioned in direct contact with the processed focal array. The elastomer is subsequently peeled back to release the array from its handle wafer. The stamp is then relaxed via cooling to room temperature or gradual release of the mechanically induced strain. Release of this strain causes the elastomer to return to its initial shape, which in turn forces the device islands of the array to draw closer. In embodiments, the interconnects are forced to buckle, enabling stretching and bending characteristics. In embodiments, the area upon which the array is meant to adhere is pre-treated with a photo-curable adhesive. Alternatively, a layer of PDMS may be used to enhance adhesion.

Figure 16B:
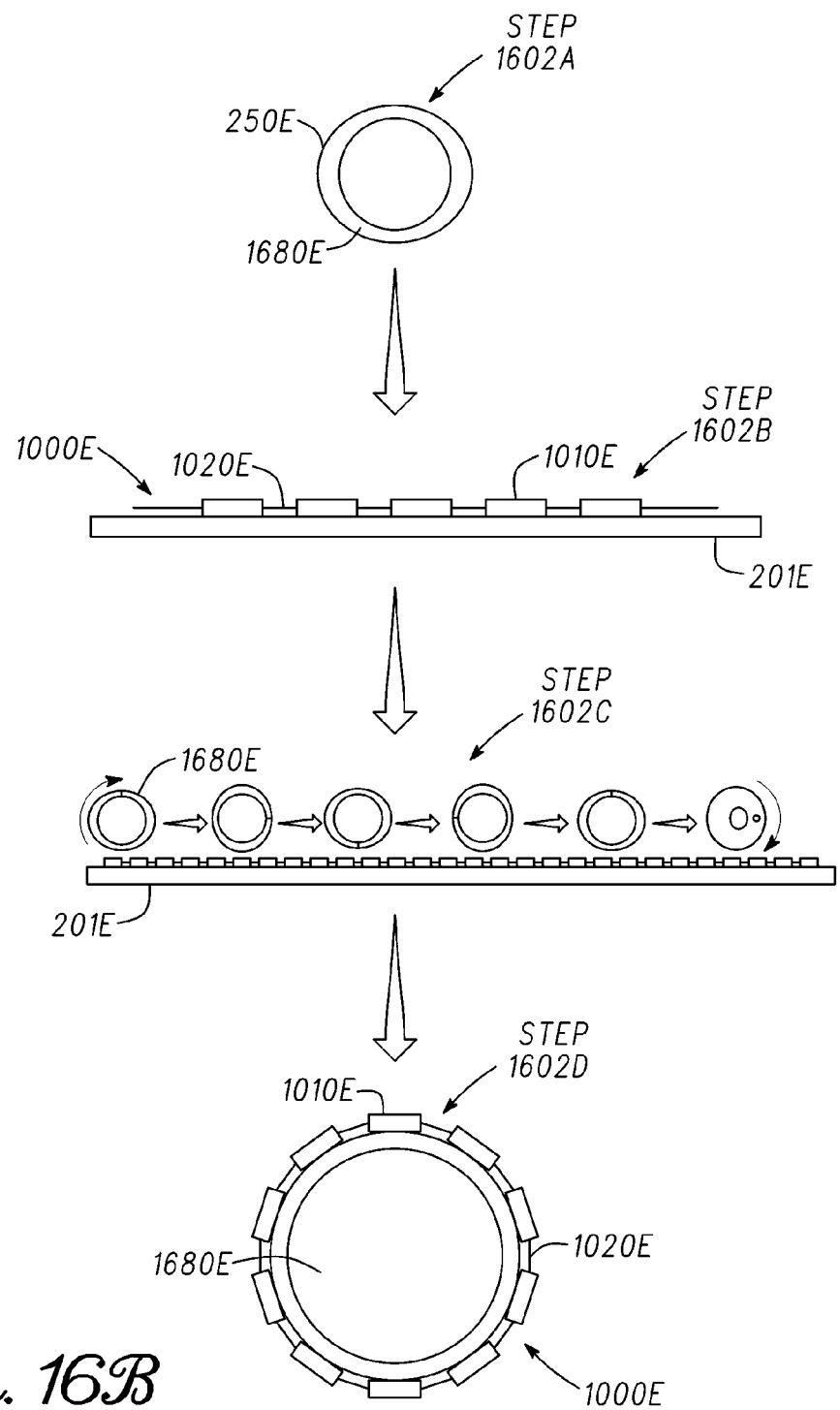

FIG. 16B details an embodiment of the process for transferring circuitry to the endoscopy device. The transfer is achieved by stamping the planar array of device islands and interconnects onto a curvilinear surface such as an endoscopic device 1680E. 1602A shows the endoscopy device having a thin PDMS shell or adhesive outer layer 250E. 1602B shows the circuitry 1000E on a carrier substrate 201E. 1602C shows the step of rotating the endoscopic device 1680E around a single revolution over the substrate 201E containing planar array of device islands, the array of photodetectors and interconnects will preferentially adhere to the surface of the endoscopy device 1680E in a curvilinear manner as shown in Step 1602D.

In another embodiment, micro-lens arrays may be required for optimal focusing and image quality. However, with proper illumination and negligible distance between the optical array and the surface being imaged, this requirement may be nullified. In the case where micro-lens arrays are required, they may be created directly as the encapsulating layer of the photodetector arrays during stretchable processing. They may also be stamped on after the endoscopic devices are made. This optical array is then encapsulated and electronically integrated with the rest of the endoscopic device in the following manner: electronic devices which have been processed for stretching, can be picked up with a planar pre-strained PDMS stamp. The pre-strained PDMS stamp is then relaxed and brought into contact with the acceptor substrate for transfer printing. This acceptor surface may be the surface of the endoscopy device, said surface coated with a thin PDMS layer, or a separate thin appropriately shaped PDMS layer that may later be wrapped around the endoscope. In the case where the devices are facing outwards on the endoscopy device substrate, they may be encapsulated (while in their compressed state) with another layer of PDMS, or a liquid layer of PDMS followed by an upper layer of solid PDMS to make a fluid encapsulation. Other materials/methods may also be applied. In the case where the devices are facing outwards on the endoscopy device substrate, they may be electrically externally interfaced at conductive pads that should be designed to be located at a convenient location. Anisotropic conductive film (ACF) connectors can be used to interface to these conductive pads, by pressing and heating the film onto the pads.

In the case where the devices are fully encapsulated or facing inwards, they may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable electronics may be electrically interfaced to an ACF prior to the transfer or encapsulation process.

Figure 17:
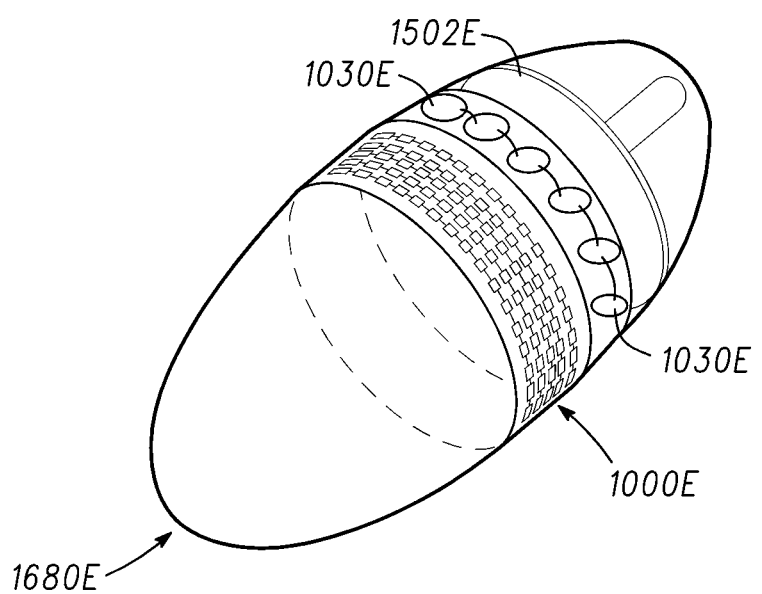
FIG. 17 depicts an embodiment of an endoscopic device according to the present invention.

In embodiments, circuitry 1000E may include a flexible LED array on the outer surface of the endoscopy device 1680E, as shown in FIG. 17. Such an array provides illumination required for optical image capture. A representative process for creating a flexible LED system is as follows:

LEDs are made from quantum well (QW) structures on a GaAs substrate. In between the GaAs substrate and the QW structure is an AlAs sacrificial layer. The QW structure is etched with reactive ion etching (RIE) to down to the sacrificial layer to form isolated square islands which may be in the range of, for example, 10-1000 µm on an edge. A partial release/undercut of the islands with HF etching is performed. Photoresist is spun onto the substrate and patterned to form squares around the corners of the islands, to serve as anchors. A full HF release etch is performed to free the islands from the GaAs bulk substrate; the photoresist anchors prevent the islands from floating away during etch, rinse and dry steps. An elastomeric stamp (for example PDMS) is used to pick up the islands and transfer them to another substrate. The transfer may be done in multiple steps, picking up a fraction of the GaAs islands at a time, to rearrange them geometrically. The substrate onto which the islands are transferred for further processing may be a layer of PET (polyethylene plastic) on a glass substrate that can be later peeled off, or a layer of polyimide on top of a PMMA (polymethylmethacrylate) sacrificial layer, or a layer of PDMS etc. Parts of the LED islands are then patterned and wet etched so that the bottom n-type contact is exposed; this may be done with, for example, a H3PO4+H2O2 combination. Parts of the islands are unetched so that the upper p-type material can be contacted electrically as well. Next, a planarization layer of polyimide is spun on, patterned so that vias extend down to the p and n type contact regions of the device. Thin film wires are deposited and patterned such that the wires to the p-type regions run in one direction, and the wires to the n-type regions run in an orthogonal direction. One of the other wires should have a gap so as not to cross-circuit. This gap is bridged by spinning another planarization layer thereover and patterning it with vias to each side of the gap, and metal is patterned over the planarization layer to make the connection. Another passivation layer is spun on top, and the entire stack is etched so that the bridges and islands remain encapsulated with polymer but the intervening areas are completely etched away. This allows the bridges to be flexible. The PMMA sacrificial layer is undercut, or the PET layer is peeled off, and the entire sheet with circuits may be picked up again by PDMS stamp, and flipped over. The backside of the lower polyimide, or bottom of the circuits, is coated with Cr/SiO2; coating of the bridges is avoided by using a shadow mask evaporation procedure. The samples are subjected to a UV ozone treatment to impart dangling bonds to the SiO2, facilitating formation of covalent bonds with the next substrate to which the circuits are transferred. This final substrate may be thermally or mechanically pre-strained PDMS, such that after transfer, the strain is relaxed and the devices move closer together and the bridges pop up and buckle to accommodate the strain.

The stretchable LED array is transferred to the endoscopy device in a manner similar to that of the cylindrical optical sensor array. It is then encapsulated and integrated at the device level according to the methods described herein in connection with the micro-lens array. FIG. 17 shows an endoscopy device 1680E wherein circuitry 1000E comprises and array of photodetector and array of LED's (individually shown as 1030E. The LED array may utilize processing 1200E in the form of a logic device so that it only illuminates areas of interest during the operation and can be turned off when not in use as a power-saving mechanism. Device also includes a data transmission facility which includes RF antenna 1502 to wireless communicate with external devices.

In another embodiment of the present invention, the endoscopy device is equipped with an array of sensors which can be selected from those herein including those in connection with the discussion of 1100. Said sensors working in conjunction with circuitry 1000E to monitor pH, the presence of chemicals, and/or enzyme activity. IN embodiments, the data collected by this sensor array is processed by local computing devices and transmitted via RF antenna or wired telemetry to an external receiver for further analysis.

At least some of the sensors in the array may comprise an ion-sensitive field effect transistor (ISLET), which generate data relating to changes in ion concentration. The output signals are typically a voltage and/or current difference, the magnitude of which varies with the change of sensed ion (e.g. hydronium) and/or enzyme. Other types of chemical sensors may be also or alternatively be utilized.

Another embodiment of the present invention relates to a capsule endoscopy device with a plurality of electronic components conformally fitted to the inside and/or outside walls of the capsule shell in order to conserve space. Conformal components are created by first performing stretchable processing on suitable materials as described herein. The basic components of such an endoscopy device include a passive or active matrix focal plane array, lens, illuminating LEDs, battery and telemetry devices (antenna and a radio transmitter). Optional components may include sensors described herein including ultrasound transducers, pressure sensors (e.g. silicon-based devices utilizing piezo-resistive or capacitive sensing mechanism, polymer-based sensors, and/or optically based sensors that measure physical deflections), temperature sensors (e.g. silicon band-gap temperature sensors, Pt resistance temperature devices), Ph/enzymatic/chemical sensors (e.g. Islets, as discussed above), targeted drug delivery components, electrocautery devices, biopsy devices, lasers, and heating devices. Components that benefit from contact with the GI wall and fluids (e.g. chemical sensors, LED, optical arrays) are situated in such a manner as to communicate fluidly or optically with the outer environment. This may be accomplished, for example, by placing the devices conformally on the outer surface of the capsule or through the use of electrodes which relay information from the outer region to the inside of the capsule. The remaining components (e.g. battery, telemetry devices) are preferably located on the inside of the capsule.

Methods for creating stretchable focal plane arrays and incorporating them into a desired substrate are described above. The same methods used to process and transfer focal plane arrays (stretchable processing) may be employed for various single-crystal silicon based electronic devices (e.g. antenna, RF transmitter, ISFET), with circuits being laid out (e.g. using CAD tools) in a manner that accommodates mechanical deformation and stretching.

In embodiments where it is desired to incorporate heterogeneous integrated circuits (non-silicon based devices), a slightly different approach may be employed. When creating a device that requires heterogeneous integration (e.g. LEDs), circuits are typically created on different substrates. After stretchable processing, the electronic devices are combined onto the same substrate using stamping methods previously described. This substrate may be the final destination of the devices (product integration) or may instead be intermediate (i.e. A rigid, flexible or stretchable material which will be incorporated into the product at a later time). At this point interconnects may be required to keep all of the heterogeneous components in electrical communication. These may be provided using soft lithography or another low-impact, low-temperature-processing (<400° C.) method with accurate alignment (<5 μm). The integrated circuit is then appropriately encapsulated and system/device interconnect integration can be executed as described above in connection with the micro-lens array.

As mentioned above, materials for the substrate used in the embodiments herein may be biocompatible. Such is the case with substrates including outer coatings of endoscopy device. In addition to biocompatibility, any part of the device housing that comes between the imager array and the object being monitored is preferably transparent. Further, the material in the outer shell of the endoscopy device facilitates easy travel through the GI tract. Examples of suitable biocompatible materials are given above.

It is to be understood that the housing of the device described above may also be the substrate and vice verse. Therefore, the skilled artisan will appreciate that certain discussions related to the substrate's material may—in certain embodiments—be understood as to apply to said housing.

It has been described herein in connection with embodiments of the invention that substrate can be fitted with circuitry comprising an array sensors and that said sensors could comprise pressure sensors. Circuitry can also comprise processing 1200 and 1200A, data collection 1300, amplifiers 1400, and data transmission 1500, among other capabilities. Therefore, another embodiment will be described that facilitates a quantitative examination of tissue based on palpation. In embodiments, the device is configured for self examination. The device is particularly suited for breast self-examinations; however, it will be appreciated that notwithstanding the following disclosure of an exemplary embodiment, the device and methods disclosed in connection with this exemplary embodiment apply to examinations of a variety of tissues and areas of the body, and such examination need not only be based on palpation.

Such an apparatus comprises a conformable and stretchable polymer fitted with an array of pressure transducers which remain operative notwithstanding stretching and bending of the body. The polymer substrate may cover a portion or the entire surface of the tissue and is used to measure the mechanical stiffness of the tissue at multiple discrete points. Pressure transducers coupled with processing facility can measure the mechanical stiffness of the tissue in response to known strains exerted on the surface of the tissue during palpation. As with other embodiment of the invention, the electronic devices of the circuitry may apparatus may comprise multiplexors, data acquisition and microprocessor circuits, which are connected via electronics wiring to the sensory circuitry covering the polymer substrate. Detection of abnormally hard regions of the tissue begins by first pressing the array of pressure transducers to the surface of the body part, for example, a breast. In embodiments, the device is fitted over the entire surface area of the body part (for example the breast) and as such a profile of the body-part stiffness can be mapped with high spatial resolution.

Embodiments of the present invention determine the presence and spatial extent of abnormally stiff legions of biological tissue, discriminate between relative stiffness of healthy and cancerous tissue, and facilitate immediate and localized therapeutic measures if appropriate. Because the mechanical properties of breast tissue are intrinsically heterogeneous, the present invention may be used regularly over time to precisely map the healthy state of the examined tissue thereby enabling the detection of structural abnormalities and/or deviations over time.

Embodiments of the present invention involve an instrumented polymer membrane fitted with flexible and stretchable electronic sensor and imaging arrays for measuring the material, mechanical, and/or optical properties of biological tissue. The invention utilizes flexible and stretchable circuitry suited for measuring parameters such as temperature, pressure and electrical conductivity of biological tissues. More specifically, the breast region is one area of interest for such tissue interrogation. The electronic components may be arranged in islands, which house required circuitry and are interconnected mechanically and electronically via interconnects. The interconnects, in turn, preferentially absorb strain and therefore enable the sensor arrays to withstand extreme stretching and conform to non-uniform shapes of biological tissues. The device islands and interconnects may be integrated into the device by transfer printing, as described below. Encapsulation of electronic devices and system/device interconnect integration can be performed at a number of stages in this process.

As decried amply herein, the arrays of devices, which may include one or more electronic devices and/or device components described herein (e.g. pressure, light and radiation sensors, biological and/or chemical sensors, amplifiers, A/D and D/A converters, optical collectors, electro-mechanical transducers, piezo-electric actuators), connected to a buffer and also to an amplifier are laid out in a device "island" arrangement. The device islands are ~50 μm×50 μm2 squares, most of which. Some islands accommodate active matrix switches and A/D converters, and some islands accommodate logic circuitry capable of reading in digital signals and processing them, and are capable of outputting data or storing data in memory cells. The circuits on these islands are configured and designed such that preferably only about one, but not more than about 100 electrical interconnections are required between any two device islands. Circuitry is made and applied according the methods described above, including in the manner described for a device island arrangement of devices.

Figure 18:
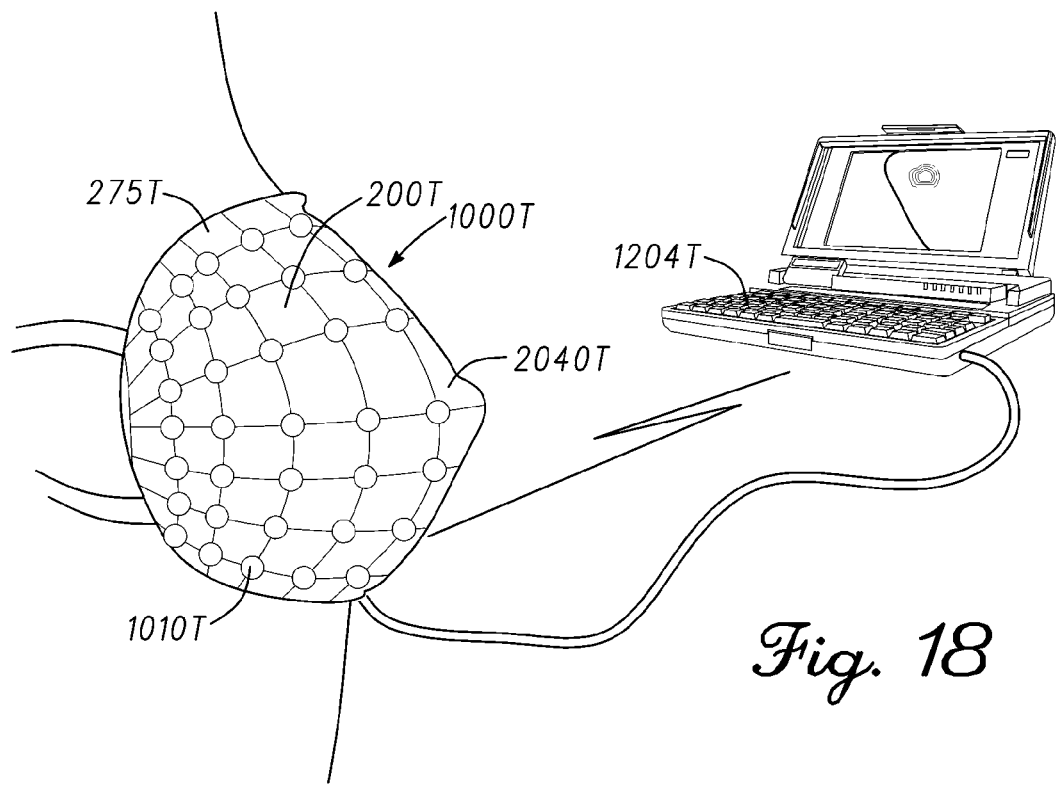
FIG. 18 depicts a tissue screening device according to an embodiment of the invention.

FIG. 18 shows an embodiment of the invention adapted for the human breast. In embodiments of the invention, a conformable polymeric membrane 200T in the shape of a single human breast 2040T. Applied to the membrane 200T is circuitry 1000T comprising sensor and/or imaging arrays based on, for example, complementary metal-oxide semiconductor (CMOS) technology. In embodiments, the array(s) 1000T are physically integrated into the surface of the polymeric breast-shaped membrane 200T such as (poly) dimethylsiloxane (PDMS). This stamping procedure may be done by a transfer printing process defined herein. As described herein, arrays 1000T can be made of CMOS devices, which offer a variety of sophisticated sensing, imaging, and therapeutic functions, including (but not limited to) pressure sensing, light imaging, and trans-dermal drug delivery. The device arrays 1000T are designed to withstand stretching and bending by the use of effective circuit layout and interconnect designs as described herein.

In embodiments, the tissue screener may be created in the form of a bra 275T or integrated into a bra.

Embodiments may include circuitry/array 1000T that comprises arrayed pressure sensors. As such electronic devices 1010T can include pressure sensor. Each pressure sensor island comprises a flexible diaphragm membrane, which can record changes in capacitance in response to deflection. The pressure sensors can be made of a series of piezoresistive strain gauges, and/or conductive polymers. Each electronic device may contain an amplifier and A/D transistors to provide local signal processing on each island. The sensor islands are encapsulated with a thin layer of polymer (~100 μm thick) to protect the interconnects and the circuitry. The surface containing the thin layer is positioned in direct contact with the breast tissue during the procedure. The surface opposite the sensors can be fitted with an additional polymer layer (300-500 μm thick) that forms as an enclosure with an air-filled gap. Inflating this air-filled space by a known amount (with a peristaltic pump) facilitates the application of known strains to the breast tissue. Therefore, breast tissue can be depressed by a fixed amount over its entire surface by inflating the air-filled space, and the pressure at each location is recorded with pressure sensors.

In another embodiment, each device 1010T includes on-off switch transistors that are coupled to said pressure sensors and activated once pressure is applied. Using this on-off mechanism, the device can determine which sensors have been pressed during sensing and communicate such to the user, via fro example, a graphical user interface on an external device, or visual means such as lighted areas were sensors have been either activated or not activated, or tactile indicators of actuation. One key advantage of using a sensor array with on-off feedback is that it alerts the user if any part of the sensor array has not been depressed in the case of manual force exertion onto the breast. Therefore, it eliminates the possibility of overlooking regions of the breast during a manual examination. Thus in embodiments, each electronic device can provide feedback if the pressure sensing mechanism was not properly activated during breast examination.

In another embodiment of the invention, the devices are anchored to the breasts with straps similar to those of a 275T.

Thus in use, the user can wear the apparatus like a bra. In embodiments, the device has a port (not shown) for connecting to an external processing facility 1200A, which in FIG. 18 is depicted as residing in a laptop computer 1204T. Wireless communication is also possible and depicted in the figure. The external device can provide power and also receives data during screening. In embodiments, processing facility 1204T, is in electronic communication with the circuitry and is configured to detect that the bra is worn and prompts the user to start the breast exam. The outer surface of the device on the side opposite to the breast can be covered with a thin encapsulating layer of polymer as described in previous embodiments. The space between this outer surface and the surface of the apparatus can be air-sealed and filled with air using a peristaltic air pump. Filling this space with air enables uniform pressure to be applied along the entire surface of the breast, which in turn provides control over how much strain is applied to the breast.

In another embodiment of the invention, the stretchable material 200T comprises circuitry 1000T having an array of ultrasound transducers (e.g. piezoelectric crystals). Each device 1010T comprises a receiver that senses acoustic reflections generated by a source emitter that sends acoustic waves through the tissue at megahertz frequencies. This embodiment can be combined with other sensors mentioned herein, including, pressure sensors to further locate and image abnormal regions of breast tissue. As with all embodiments herein, the sensors can be in electronic communication with the other facilities, electronic devices, components, and elements of the circuitry or external devices including processing facilities that receive the data from said sensors and process it according to the methods described herein, and further cause output devices to generate the output as described herein.

Circuitry 1000T could also comprise an array of infrared emitters and detectors (e.g. bolometer). The infrared wavelength is chosen to minimize the ratio of healthy tissue absorption to cancerous tissue absorption. The emitters illuminate the breast and the detectors image the radiation. This embodiment can be combined and integrated with any of the aforementioned sensing concepts for increased accuracy.

Circuitry 1000T could also comprise an array of stimulating and recording electrodes to produce a spatial map of electrical impedance of the tissue. The electrical conductivity and dielectric properties of cancerous tissue may differ from those of healthy tissue. To detect changes in electrical impedance induced by the presence of local cancer tissue, a known AC current can be injected at a known location, and voltage is recorded at a number of points defined by the array of recording electrodes. In this embodiment, the encapsulating layer of polymer covers everything except the contact regions of the electrodes. A photo-patternable polymer can be used to achieve this step.

Electrical impedance scanning provides data to enable a 3-D spatial map of complex impedance and permittivity over a range of frequencies, which can be used as a sensing tool to predict the presence of abnormal cancerous cells deep within breast tissue. This embodiment can be combined and integrated with any of the aforementioned methods and concepts for increased accuracy.

The data collected by the array of sensors can be stored for retrieval and/or transmitted to an external system for time-based tracking of tissue health.

In embodiments, the sensor data from the array 1000T of pressure transducers can amplified and converted to digital form at the level of each sensor and then transmitted to a multiplexor. Alternatively, the analog circuitry can be included at the level of each device 1010T and the digital processing circuits can be housed off of the polymer. Once the data is collected from each point and transmitted to a computer terminal, the user may prompted that the examination is complete. The user may examine the data herself and/or send it to her doctor for further review (as an example).

Thus, in embodiments it will be apparent that the circuitry of the device is in electronic communication with a processing facility configured to accept data from the device and cause output facility (previously discussed in connection with FIG. 1 as 300) to generate a graphical or otherwise visual presentation of data related to the examination. For example, tissue maps as described herein may be created from all sensor data disclosed herein and presented on output facility (as shown on 1204T). Textual and graphical data relating to the data generated by the circuitry may be presented to the user. The processing facility may be configured to cause historical data generated by the circuitry to be stored, aggregated, and presented in a variety of ways including daily, weekly, monthly, or any other useful interval readings, charts, reports, and the like.

Returning to the physical characteristics of the device itself, the device may be opaque such that the woman's breasts are not visible. This feature can be achieved by adding opaque (e.g., black) dye to the elastomer prior to curing. In this embodiment, the array of sensors remains in close contact with the breast without having to expose her bare breasts. Because of the biocompatibility of polymers like PDMS, this type of device can be fitted within a normal bra for convenience.

In one embodiment of the invention the electronics are integrated into an elastomeric material which contours a breast. This shape is reproducible in different sizes depending on the breast size of the intended user. The process of creating the breast shaped device begins with the creation of a first breast shaped mold. A second negatively shaped mold is then made to match the curvature of the first. An elastomeric material such as PDMS is poured between the two moulds to create a thin film (less than 2 mm). This layer is cured to create a solid breast shaped film of elastomeric material upon which the electronics will be stamped by the transfer printing process described above. In order to accomplish this printing step, the elastomeric material is stretched into a flat plane and placed in contact with the already "stretch processed" electronics. The electronics preferentially adhere to the surface of the elastomer either by Van der Waal forces or by chemical aided means. Subsequently, the elastomer with embedded electronics is relaxed and buckling occurs within the interconnects of the electronics array, enabling stretchability.

Further encapsulation and device integration may be required. This may be done by connecting (manually or by electronic automation) anisotropic conductive films (ACF) to bond pads which are designed to be in an easily accessible area on the stretchable electronic array (for example on its outer perimeter). This ACF connects the electronics embedded elastomer to a device which is responsible for supplying power, relaying information of other tasks that require electrical contact.

In accordance with one or more embodiments, the stretchable electronics are integrated directly onto a bra-like substrate. This may be achieved by coating a bra-like article with an elastomeric substrate (e.g. PDMS) and adhering the above described stretchable electronic array to the newly coated bra-like article.

Certain of the methods and systems described in connection with the invention described (hereinafter referred to as the "Subject Methods and Systems") may be deployed in part or in whole through a machine that executes computer software, program codes, and/or instructions on a processor integrated with or separate from the electronic circuitry described herein. Said certain methods and systems will be apparent to those skilled in the art, and nothing below is meant to limit that which has already been disclosed but rather to supplement it.

The active stretchable or flexible circuitry described herein may be considered the machine necessary to deploy the Subject Methods and System in full or in part, or a separately located machine may deploy the Subject Methods and Systems in whole or in part. Thus, "machine" as referred to herein may be applied to the circuitry described above, a separate processor, separate interface electronics or combinations thereof.

The Subject Methods and Systems invention may be implemented as a method on the machine, as a system or apparatus as part of or in relation to the machine, or as a computer program product embodied in a computer readable medium executing on one or more of the machines. In embodiments, the processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like. Nothing in this paragraph or the paragraphs below is meant to limit or contradict the description of the processing facility described herein and throughout.

A processor may include one or more cores that may enhance speed and performance of a multiprocessor. In embodiments, the process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, stand-alone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been described in connection with certain preferred embodiments, other embodiments would be understood by one of ordinary skill in the art and are encompassed herein.

All documents referenced herein are hereby incorporated by reference.

What is claimed is:

1. An apparatus comprising:
   an inflatable substrate;
   circuitry disposed on said substrate comprising an array of active devices, said circuitry including stretchable electrical interconnects that electrically interconnect the active devices of the array of active devices for the circuitry to remain functional upon inflation of the substrate, said array of active devices comprising sensing devices for detecting data indicative of a parameter associated with a tissue;
   a processing facility in electronic communication with said circuitry, receiving said data indicative of said parameter associated with said tissue; and
   an output facility in electronic communication with said processing facility, said processing facility configured to generate output data associated with said tissue and to cause said output facility to create said output data.

2. The apparatus of claim 1, wherein said substrate is stretchable.

3. The apparatus of claim 1, wherein said circuitry is in conformal contact with said tissue.

4. The apparatus of claim 1, wherein said circuitry is encapsulated with a thin polymer layer.

5. The apparatus of claim 1, wherein said circuitry is stretchable up to 300%.

6. The apparatus of claim 1, wherein said active devices are located discretely from one another.

7. The apparatus of claim 1, wherein said stretchable interconnects electrically connect said devices.

8. The apparatus of claim 1, wherein said sensing devices comprise temperature sensors.

9. The apparatus of claim 1, wherein said sensing devices comprise contact sensors.

10. The apparatus of claim 1, wherein said sensing devices comprise pressure sensors.

11. The apparatus of claim 1, wherein said sensing devices comprise ultrasound emitters and receivers.

12. The apparatus of claim 11, wherein said processing facility receives data generated by said sensing devices and produces an image of said tissue.

13. The apparatus of claim 1, wherein said sensing devices are configured to be in an active matrix.

14. The apparatus of claim 13, wherein said circuitry comprises at least one of an amplifier and a logic circuit to operate said sensing devices in said active matrix.

15. The apparatus of claim 1, further comprising a multiplexer.

16. The apparatus of claim 15, wherein said substrate is a balloon coupled to a catheter guide wire, and said multiplexer is located at a base of said catheter guide wire.

17. The apparatus of claim 1, wherein said processing facility is within said circuitry.

18. The apparatus of claim 1, wherein said processing facility is separate from said circuitry.

19. The apparatus of claim 1, wherein said output data related to said tissue is a map.

20. The apparatus of claim 19, wherein said map comprises a map of electrical activity of said tissue.

21. The apparatus of claim 1, wherein said output data comprises data related to temperature heterogeneity present in arterial plaque.

22. The apparatus of claim 1, wherein said output data comprises an indication of plaque type.

23. The apparatus of claim 1, wherein said circuitry comprises a therapeutic facility.

24. The apparatus of claim 23, wherein said therapeutic facility is configured to ablate said tissue.

25. The apparatus of claim 1, wherein said circuitry comprises light emitting electronics.

26. The apparatus of claim 1, wherein said circuitry comprises an array of photodetectors in communication with said processing facility.

27. The apparatus of claim 26, wherein said processing facility is configured to generate an image of said tissue as the output data and to cause said output facility to output the image.

28. The apparatus of claim 27, wherein said image is high resolution.

29. The apparatus of claim 26, wherein said circuitry is delivered via a catheter having a guide wire, and wherein said guide wire comprises a light source to provide light to said photodetectors.

30. The apparatus of claim 29, wherein said light source is an optical fiber.

31. The apparatus of claim 1, wherein said tissue is a pulmonary vein.

32. The apparatus of claim 1, wherein said tissue is a septal wall of a heart.

33. The apparatus of claim 1, wherein said tissue is an atrial surface of a heart.

34. The apparatus of claim 1, wherein said tissue is a ventricular surface of a heart.

35. The apparatus of claim 1, wherein said substrate comprises a reservoir in communication with a surface of said substrate.

36. The apparatus of claim 35, wherein said circuitry is configured to open valves on the substrate to release a drug contained within said reservoir.

37. The apparatus of claim 36, wherein said circuitry causes the valves to release said drug in a controlled manner.

38. An apparatus comprising:
an inflatable substrate;
circuitry disposed on said substrate comprising an array of active devices, said circuitry being configured to remain functional upon inflation of the substrate, said array of active devices comprising sensing devices for detecting data indicative of a parameter associated with a tissue, said sensing devices comprising ultrasound emitters and receivers;
a processing facility in electronic communication with said circuitry, receiving said data indicative of said parameter associated with said tissue; and
an output facility in electronic communication with said processing facility, said processing facility configured to generate output data associated with said tissue and to cause said output facility to create said output data.

39. The apparatus of claim 38, wherein said substrate is stretchable.

40. The apparatus of claim 38, wherein said circuitry is in conformal contact with said tissue.

41. The apparatus of claim 38, wherein said circuitry is encapsulated with a thin polymer layer.

42. The apparatus of claim 38, wherein said circuitry is stretchable up to 300%.

43. The apparatus of claim 38, wherein said active devices are located discretely from one another.

44. The apparatus of claim 38, wherein said circuitry comprises stretchable electrical interconnects.

45. The apparatus of claim 44, wherein said stretchable interconnects electrically connect said devices.

46. The apparatus of claim 38, wherein said sensing devices comprise temperature sensors.

47. The apparatus of claim 38, wherein said sensing devices comprise contact sensors.

48. The apparatus of claim 38, wherein said sensing devices comprise pressure sensors.

49. The apparatus of claim 38, wherein said processing facility receives data generated by said sensing devices and produces an image of said tissue.

50. The apparatus of claim 38, wherein said sensing devices are configured to be in an active matrix.

51. The apparatus of claim 50, wherein said circuitry comprises at least one of an amplifier and a logic circuit to operate said sensing devices in said active matrix.

52. The apparatus of claim 38, further comprising a multiplexer.

53. The apparatus of claim 52, wherein said substrate is a balloon coupled to a catheter guide wire, and said multiplexer is located at a base of said catheter guide wire.

54. The apparatus of claim 38, wherein said processing facility is within said circuitry.

55. The apparatus of claim 38, wherein said processing facility is separate from said circuitry.

56. The apparatus of claim 38, wherein said output data related to said tissue is a map.

57. The apparatus of claim 56, wherein said map comprises a map of electrical activity of said tissue.

58. The apparatus of claim 38, wherein said output data comprises data related to temperature heterogeneity present in arterial plaque.

59. The apparatus of claim 38, wherein said output data comprises an indication of plaque type.

60. The apparatus of claim 38, wherein said circuitry comprises a therapeutic facility.

61. The apparatus of claim 60, wherein said therapeutic facility is configured to ablate said tissue.

62. The apparatus of claim 38, wherein said circuitry comprises light emitting electronics.

63. The apparatus of claim 38, wherein said circuitry comprises an array of photodetectors in communication with said processing facility.

64. The apparatus of claim 63, wherein said processing facility is configured to generate an image of said tissue as the output data and to cause said output facility to output the image.

65. The apparatus of claim 64, wherein said image is high resolution.

66. The apparatus of claim 63, wherein said circuitry is delivered via a catheter having a guide wire, and wherein said guide wire comprises a light source to provide light to said photodetectors.

67. The apparatus of claim 66, wherein said light source is an optical fiber.

68. The apparatus of claim 38, wherein said tissue is a pulmonary vein.

69. The apparatus of claim 38, wherein said tissue is a septal wall of a heart.

70. The apparatus of claim 38, wherein said tissue is an atrial surface of a heart.

71. The apparatus of claim 38, wherein said tissue is a ventricular surface of a heart.

72. The apparatus of claim 38, wherein said substrate comprises a reservoir in communication with a surface of said substrate.

73. The apparatus of claim 72, wherein said circuitry is configured to open valves on the substrate to release a drug contained within said reservoir.

74. The apparatus of claim 73, wherein said circuitry causes the valves to release said drug in a controlled manner.

* * * * *